(12) United States Patent
Ando

(10) Patent No.: US 10,564,448 B2
(45) Date of Patent: Feb. 18, 2020

(54) DIFFRACTIVE MULTI-FOCAL OPHTHALMIC LENS AND METHOD FOR MANUFACTURING DIFFRACTIVE MULTI-FOCAL OPHTHALMIC LENS

(71) Applicant: MENICON CO., LTD., Nagoya-shi, Aichi (JP)

(72) Inventor: Ichiro Ando, Kasugai (JP)

(73) Assignee: MENICON CO., LTD., Nagoya (JP)

( * ) Notice: Subject to any disclaimer, the term of this patent is extended or adjusted under 35 U.S.C. 154(b) by 0 days.

(21) Appl. No.: 15/763,571

(22) PCT Filed: Oct. 1, 2015

(86) PCT No.: PCT/JP2015/077999
§ 371 (c)(1),
(2) Date: Mar. 27, 2018

(87) PCT Pub. No.: WO2017/056305
PCT Pub. Date: Apr. 6, 2017

(65) Prior Publication Data
US 2018/0275428 A1   Sep. 27, 2018

(51) Int. Cl.
*G02C 7/06* (2006.01)
*G02C 7/04* (2006.01)

(52) U.S. Cl.
CPC ............ *G02C 7/06* (2013.01); *G02C 7/044* (2013.01); *G02C 2202/20* (2013.01)

(58) Field of Classification Search
CPC .......... G02C 7/06; G02C 7/041; G02C 7/042; G02C 7/043; G02C 7/044; G02C 7/045; G02C 7/049; G02C 2202/20

USPC ............ 351/159.11, 159.15, 159.35, 159.44
See application file for complete search history.

(56) References Cited

U.S. PATENT DOCUMENTS

| | | | |
|---|---|---|---|
| 6,829,093 B1 | 12/2004 | Nakai | |
| 2007/0182921 A1 | 8/2007 | Zhang et al. | |
| 2009/0268155 A1 | 10/2009 | Weeber | |
| 2011/0270390 A1 | 11/2011 | Kobayashi et al. | |

(Continued)

FOREIGN PATENT DOCUMENTS

| | | |
|---|---|---|
| EP | 2378319 A1 | 10/2011 |
| JP | 2001-042112 A | 2/2001 |

(Continued)

OTHER PUBLICATIONS

Apr. 12, 2018 International Preliminary Report on Patentability issued in International Patent Application No. PCT/JP2015/077999.

(Continued)

*Primary Examiner* — Darryl J Collins
(74) *Attorney, Agent, or Firm* — Oliff PLC

(57) ABSTRACT

The present invention pertains to a diffractive multi-focal ophthalmic lens, and the purpose is to provide a novel structure and manufacturing method in which improvement in optical characteristics such as halo reduction is obtained. A diffractive multi-focal ophthalmic lens in which a plurality of focal points are set by a diffraction grating comprising a blaze shaped phase function in which a plurality of zone sequences are overlapped, wherein adopted is a structure expressed by a phase function in which an inclination of a blaze of a specific adjustment zone in a standard profile is reversed.

23 Claims, 32 Drawing Sheets

(56) References Cited

U.S. PATENT DOCUMENTS

| | | | |
|---|---|---|---|
| 2011/0292335 A1* | 12/2011 | Schwiegerling | A61F 2/1613 351/159.44 |
| 2012/0224138 A1 | 9/2012 | Cohen | |
| 2012/0283825 A1 | 11/2012 | Houbrechts et al. | |
| 2014/0347624 A1 | 11/2014 | Ando et al. | |
| 2017/0227789 A1 | 8/2017 | Ando et al. | |

FOREIGN PATENT DOCUMENTS

| | | |
|---|---|---|
| JP | 2009526275 A | 7/2009 |
| JP | 2010-158315 A | 7/2010 |
| JP | 2012-517625 A | 8/2012 |
| JP | 2013-517822 A | 5/2013 |
| JP | 2014-228660 A | 12/2014 |
| WO | 2010/079528 A1 | 7/2010 |
| WO | 2013/118176 A1 | 8/2013 |
| WO | 2013/118499 A1 | 8/2013 |
| WO | 2014/091528 A1 | 6/2014 |
| WO | 2016/021075 A1 | 2/2016 |

OTHER PUBLICATIONS

Dec. 22, 2015 Search Report issued in International Patent Application No. PCT/JP2015/077999.
Apr. 26, 2019 Extended European Search Report issued in European Patent Application No. 15905459.2.
Aug. 19, 2019 Office Action dated in Chinese Application No. 201580083458.0.
Aug. 29, 2019 Office Action dated in Japanese Application No. 2017-542651.

* cited by examiner

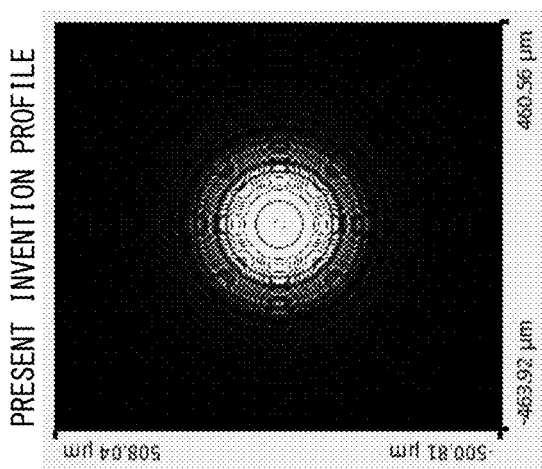
FIG.6C PRESENT INVENTION PROFILE
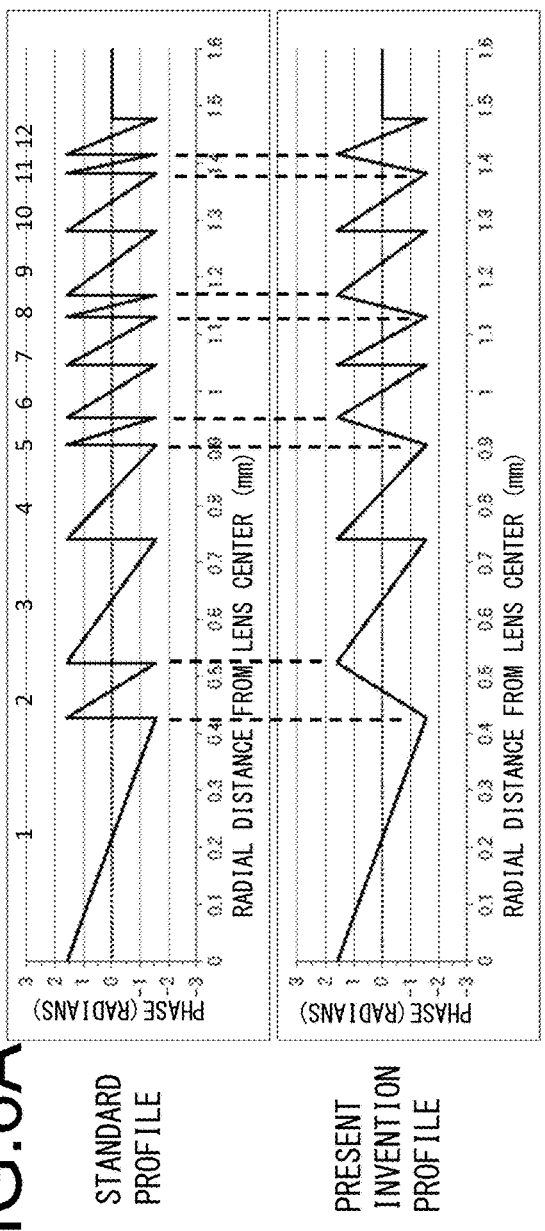
FIG.6A
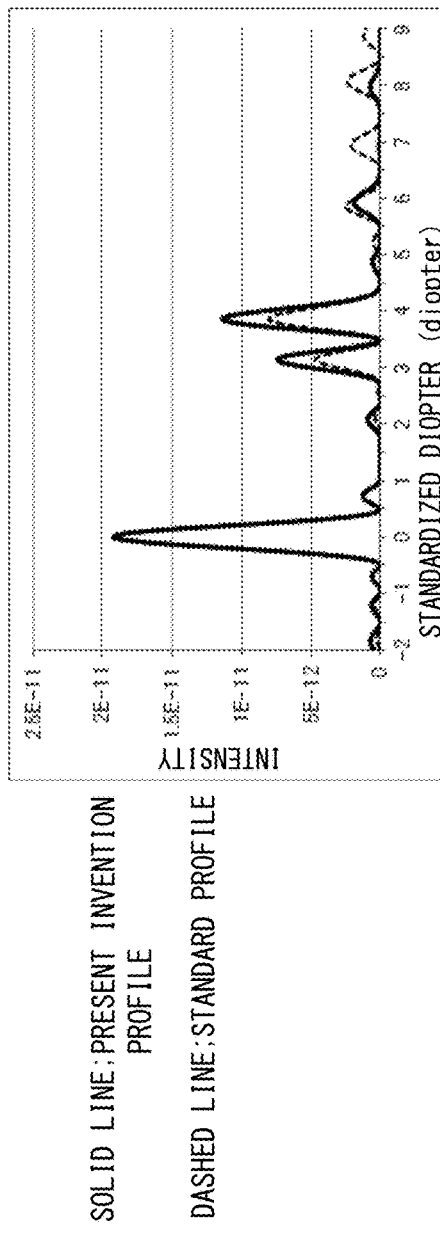
FIG.6B
INTENSITY DISTRIBUTION ON OPTICAL AXIS OF STANDARD PROFILE AND PRESENT INVENTION PROFILE
SOLID LINE: PRESENT INVENTION PROFILE
DASHED LINE: STANDARD PROFILE

COMPARATIVE EXAMPLE 1

EXAMPLE 1
+
COMPARATIVE
EXAMPLE 1
POINT SPREAD
FUNCTION
(PLOT DIAGRAM)

EXAMPLE 1
+
COMPARATIVE
EXAMPLE 1

EXAMPLE 1
+
COMPARATIVE
EXAMPLE 1
INTENSITY
DISTRIBUTION
ON OPTICAL AXIS

COMPARATIVE EXAMPLE 2

EXAMPLE 2

EXAMPLE 2
+
COMPARATIVE EXAMPLE 2

INTENSITY DISTRIBUTION ON OPTICAL AXIS

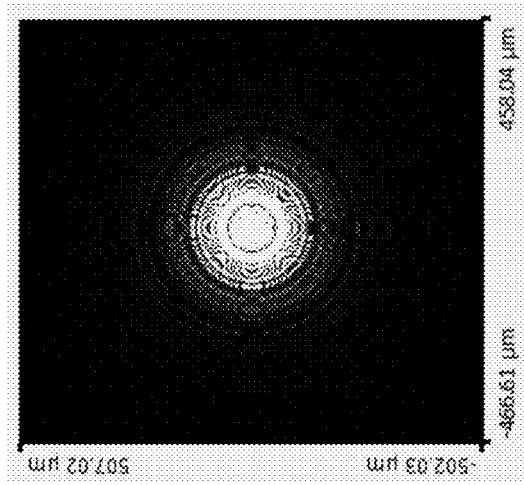
FIG. 9B EXAMPLE 2
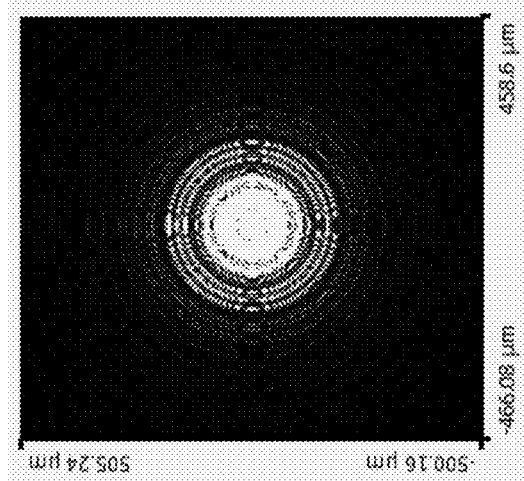
FIG. 9A COMPARATIVE EXAMPLE 2
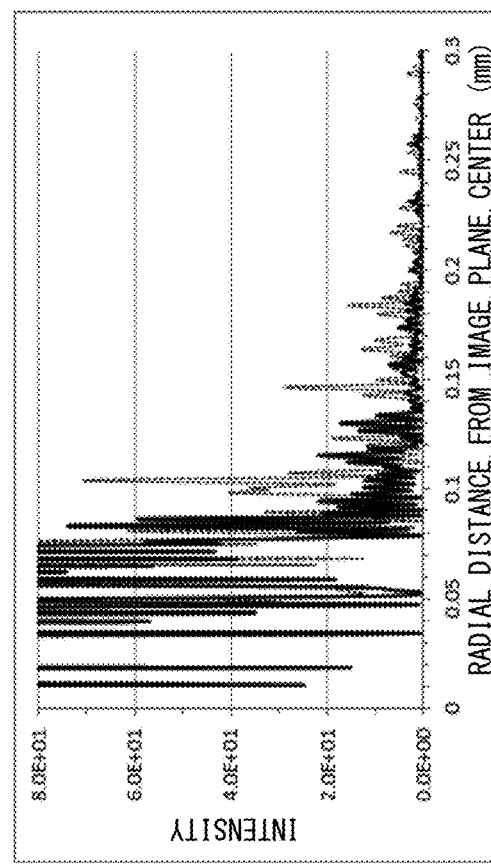
FIG. 9C
EXAMPLE 2
+
COMPARATIVE EXAMPLE 2
POINT SPREAD FUNCTION (PLOT DIAGRAM)

EXAMPLE 2-2

EXAMPLE 2-3

EXAMPLE 2-4

EXAMPLE 2-5

EXAMPLE 2-6

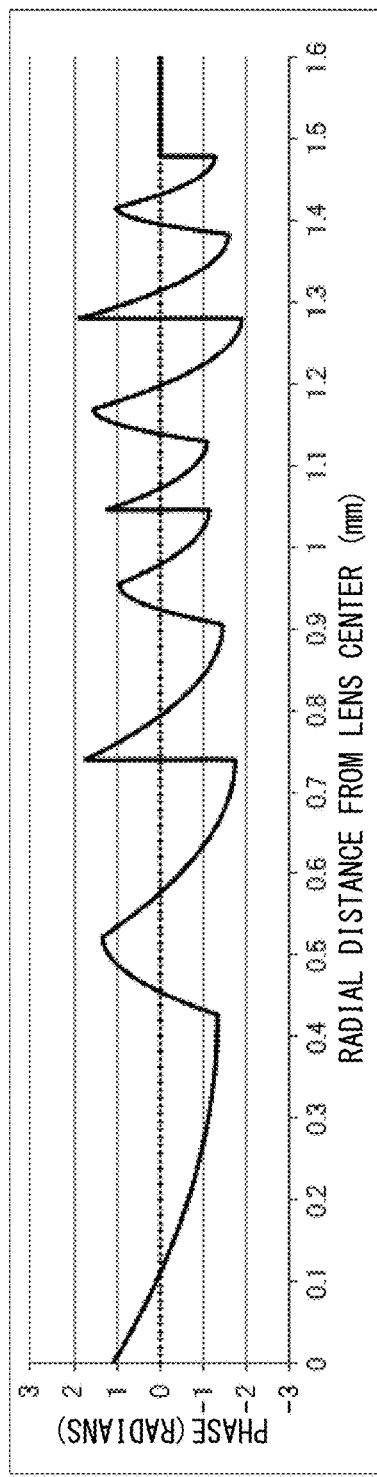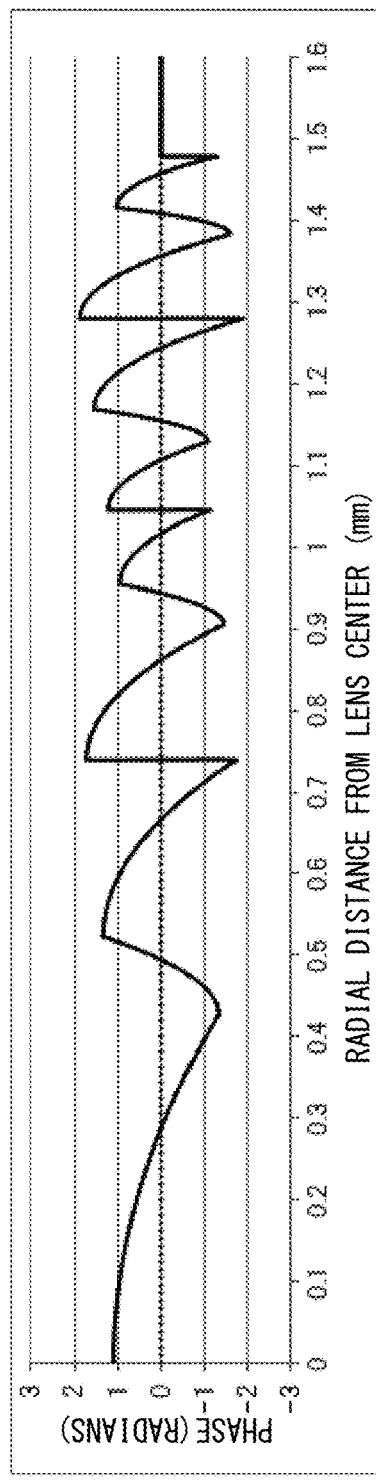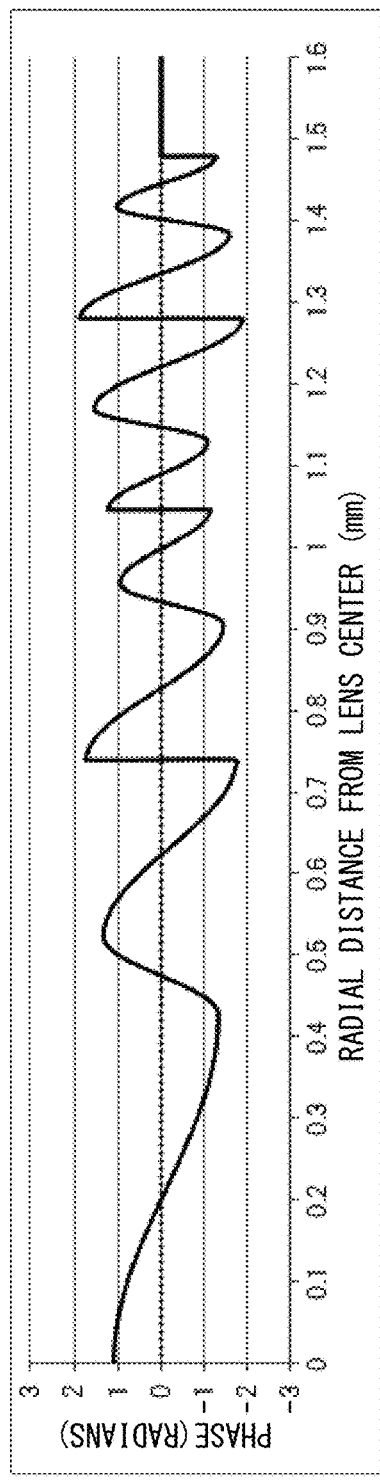
FIG.15A EXAMPLE 2-7
FIG.15B EXAMPLE 2-8
FIG.15C EXAMPLE 2-9

INTENSITY DISTRIBUTION
ON OPTICAL AXIS OF
ZONE NO. 3, 4, 9, 10
IN EXAMPLE 1 OR 2

INTENSITY DISTRIBUTION
ON OPTICAL AXIS OF
ZONE NO. 1, 6, 7, 12
IN EXAMPLE 1 OR 2

INTENSITY DISTRIBUTION
ON OPTICAL AXIS OF
ZONE NO. 2, 5, 8, 11
IN EXAMPLE 1 OR 2

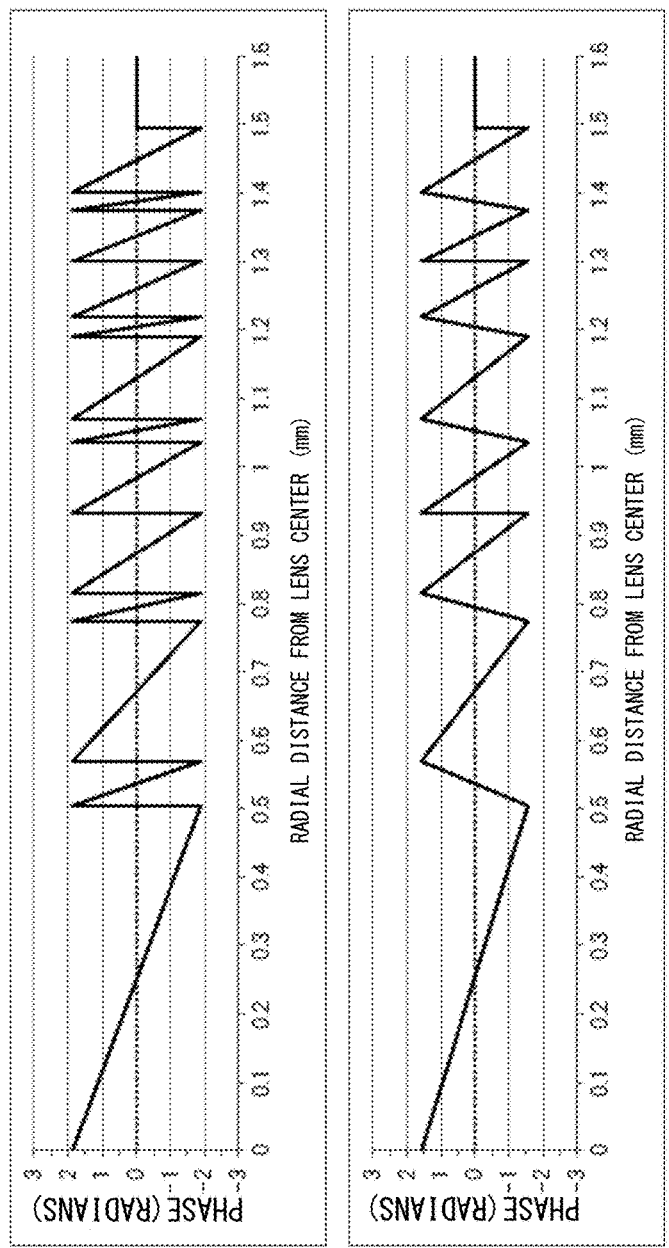
FIG.17A COMPARATIVE EXAMPLE 3
EXAMPLE 3
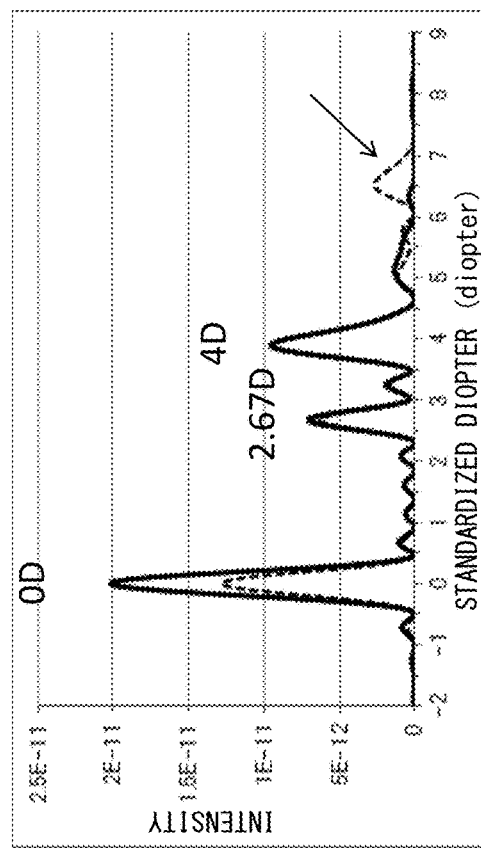
FIG.17B EXAMPLE 3 + COMPARATIVE EXAMPLE 3 INTENSITY DISTRIBUTION ON OPTICAL AXIS

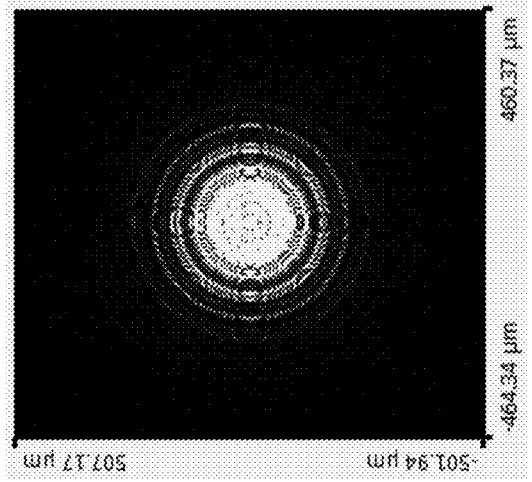
FIG.18A COMPARATIVE EXAMPLE 3
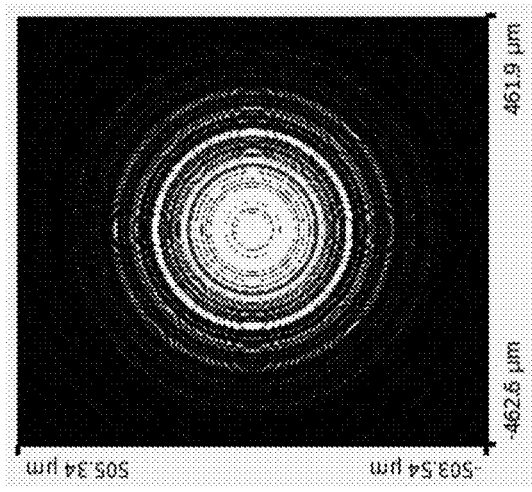
FIG.18B EXAMPLE 3
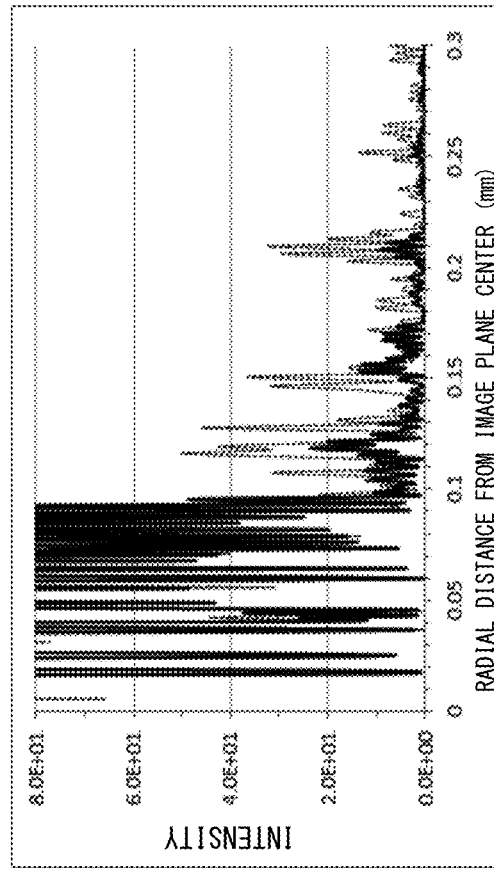
FIG.18C
EXAMPLE 3
+
COMPARATIVE EXAMPLE 3
POINT SPREAD FUNCTION (PLOT DIAGRAM)

COMPARATIVE EXAMPLE 4

EXAMPLE 4

EXAMPLE 4
+
COMPARATIVE EXAMPLE 4
INTENSITY DISTRIBUTION ON OPTICAL AXIS

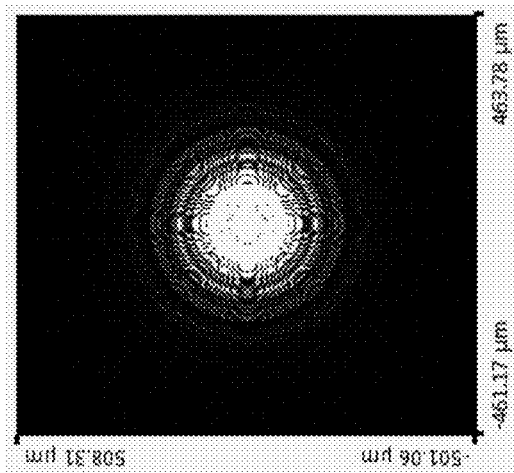
FIG.20B EXAMPLE 4
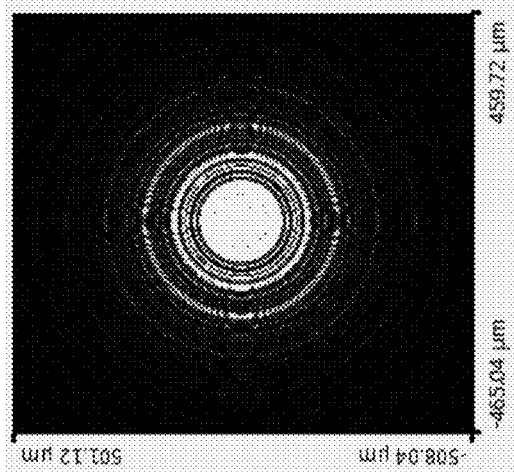
FIG.20A COMPARATIVE EXAMPLE 4
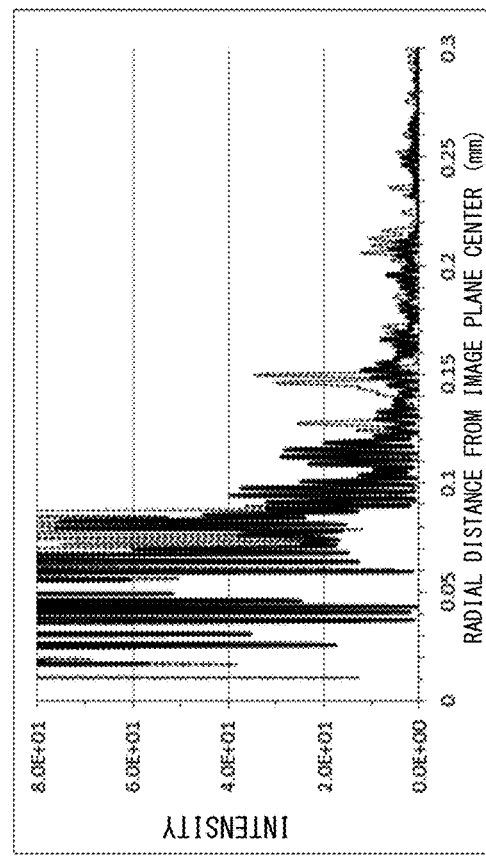
FIG.20C
EXAMPLE 4
+
COMPARATIVE EXAMPLE 4
POINT SPREAD FUNCTION (PLOT DIAGRAM)

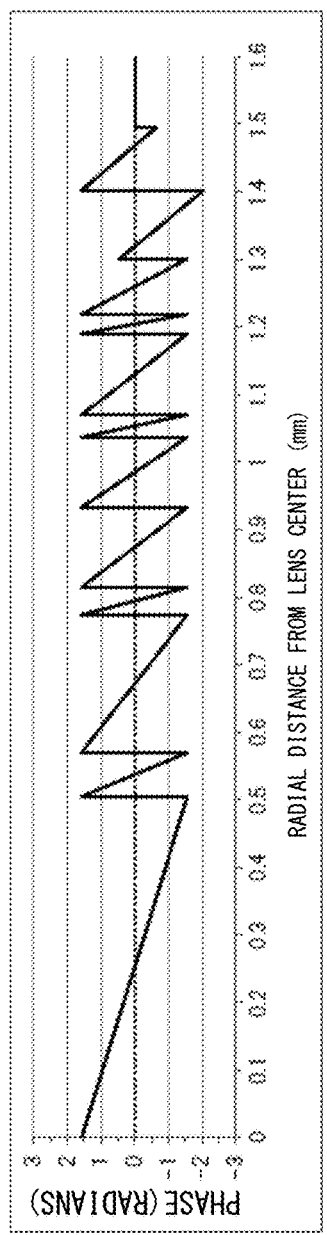
FIG.21A
COMPARATIVE EXAMPLE 5
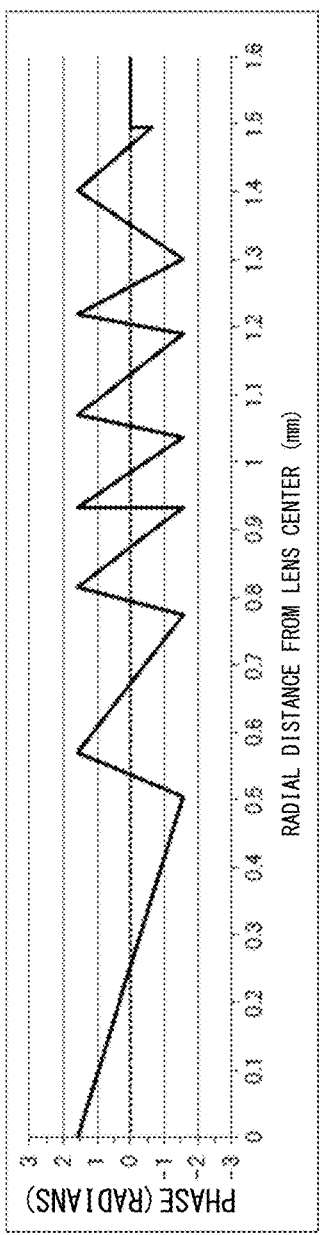
EXAMPLE 5
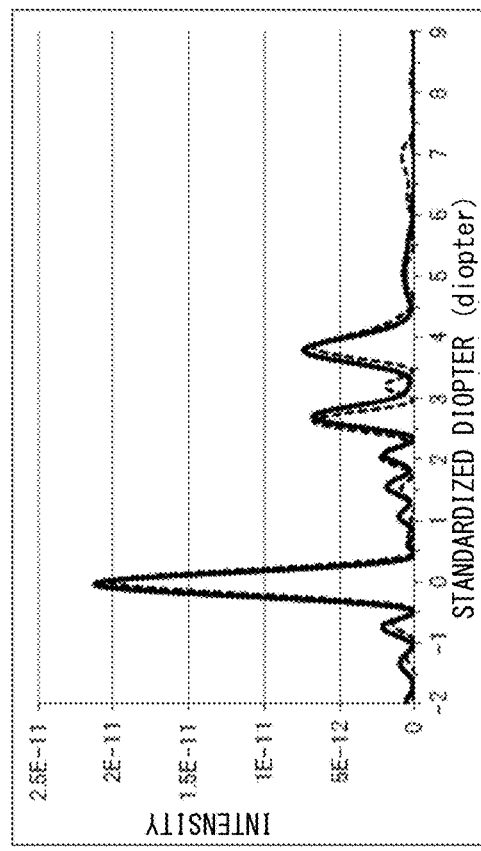
FIG.21B
EXAMPLE 5
+
COMPARATIVE EXAMPLE 5
INTENSITY DISTRIBUTION ON OPTICAL AXIS

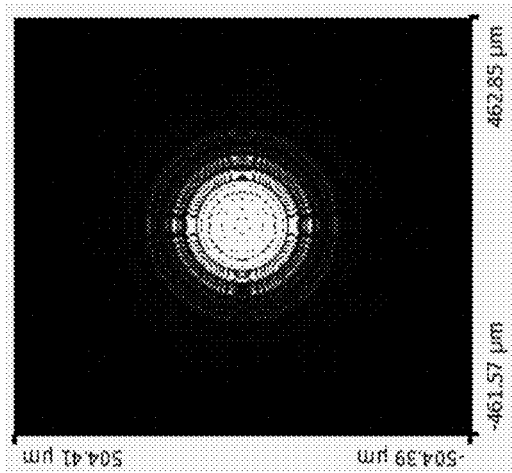
FIG.22B EXAMPLE 5
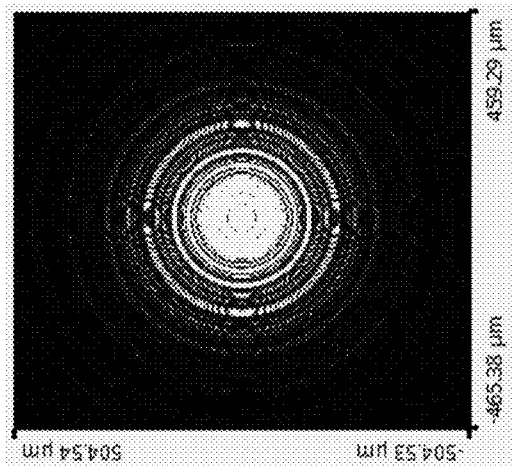
FIG.22A COMPARATIVE EXAMPLE 5
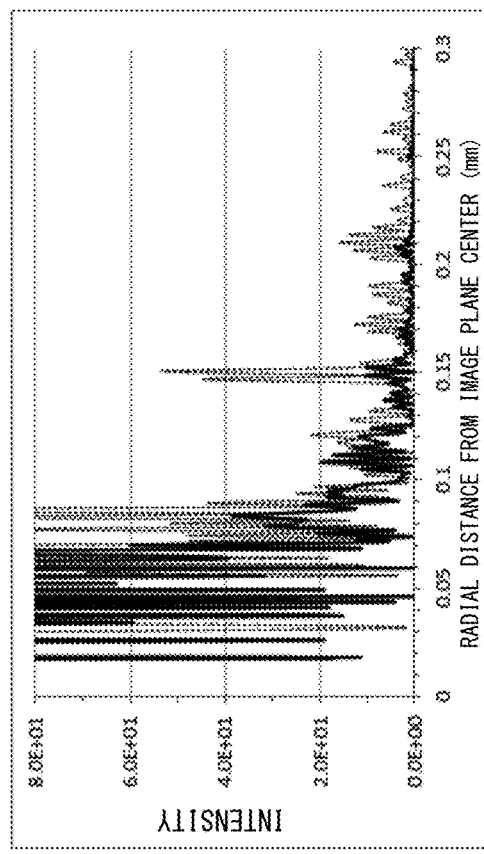
FIG.22C EXAMPLE 5 + COMPARATIVE EXAMPLE 5 POINT SPREAD FUNCTION (PLOT DIAGRAM)

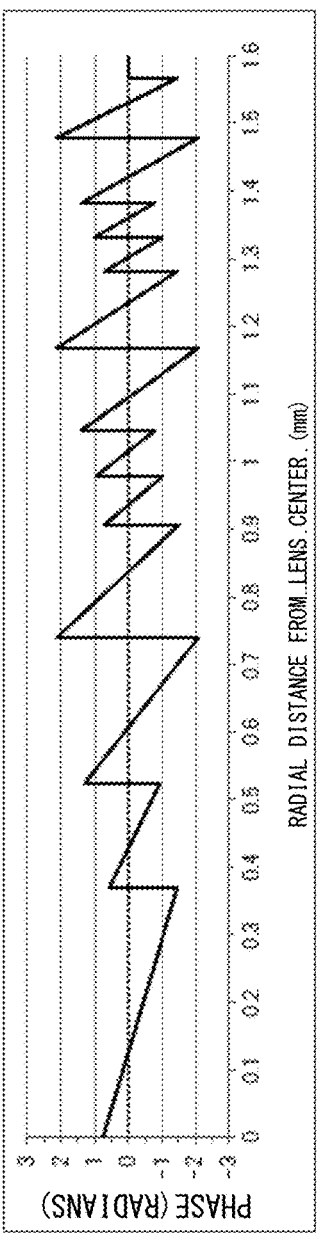
FIG.23A
COMPARATIVE EXAMPLE 6
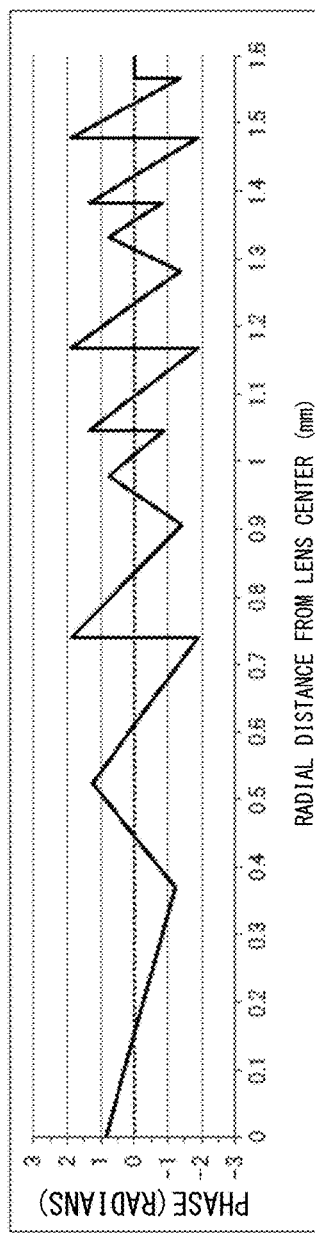
EXAMPLE 6
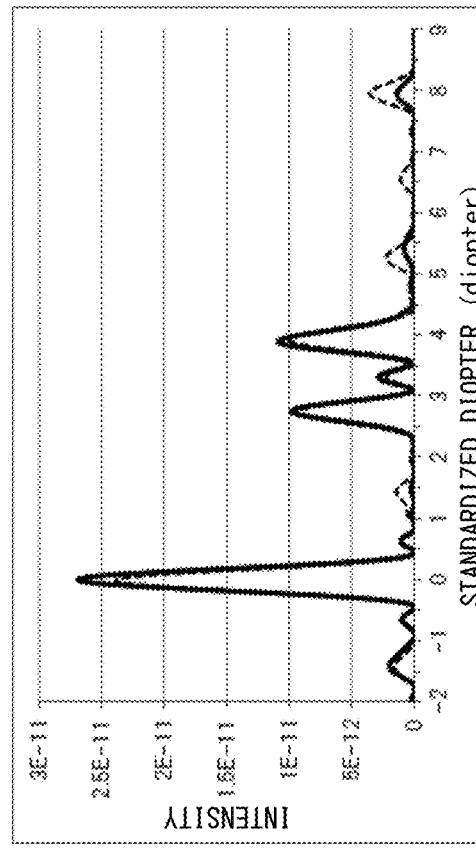
FIG.23B
EXAMPLE 6
+
COMPARATIVE
EXAMPLE 6
INTENSITY
DISTRIBUTION
ON OPTICAL AXIS

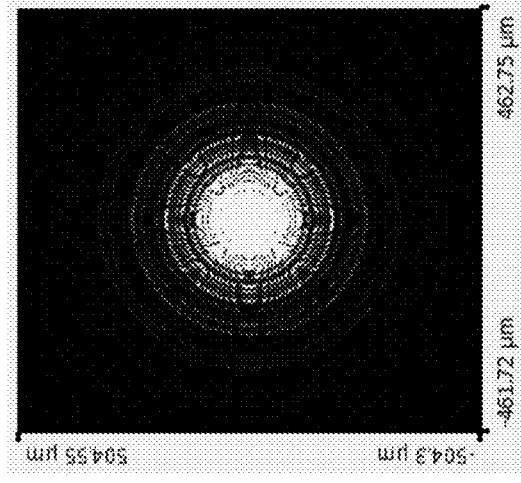
FIG.24B EXAMPLE 6
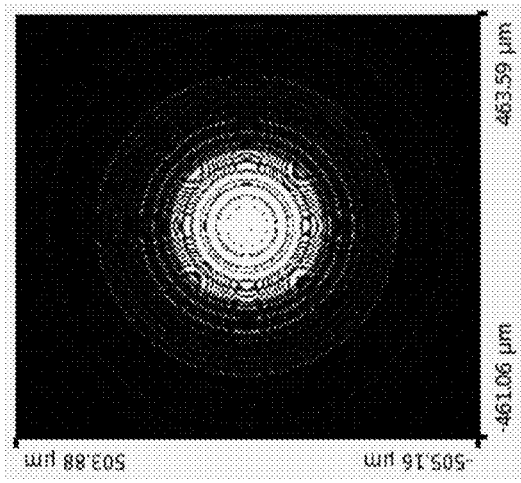
FIG.24A COMPARATIVE EXAMPLE 6
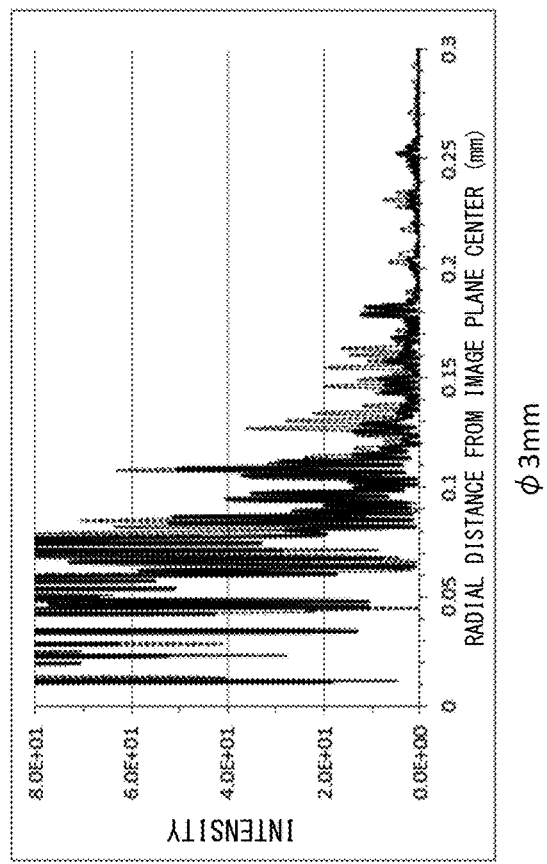
FIG.24C
EXAMPLE 6
+
COMPARATIVE
EXAMPLE 6
POINT SPREAD
FUNCTION
(PLOT DIAGRAM)

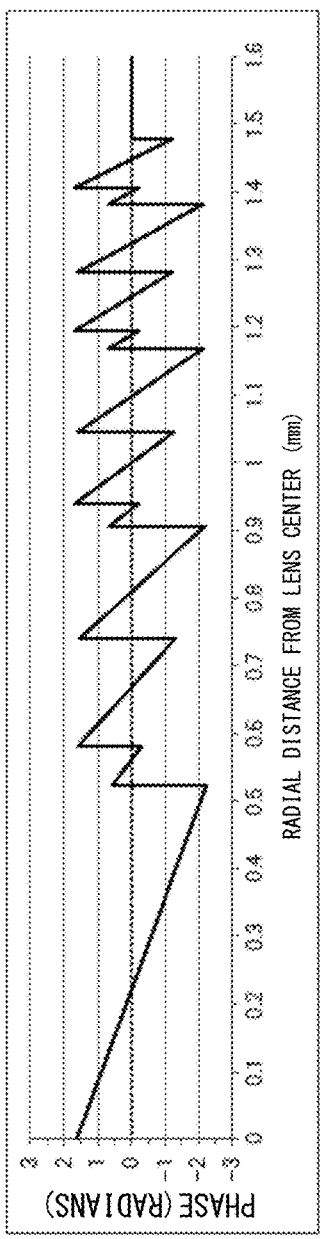
FIG.25A COMPARATIVE EXAMPLE 7
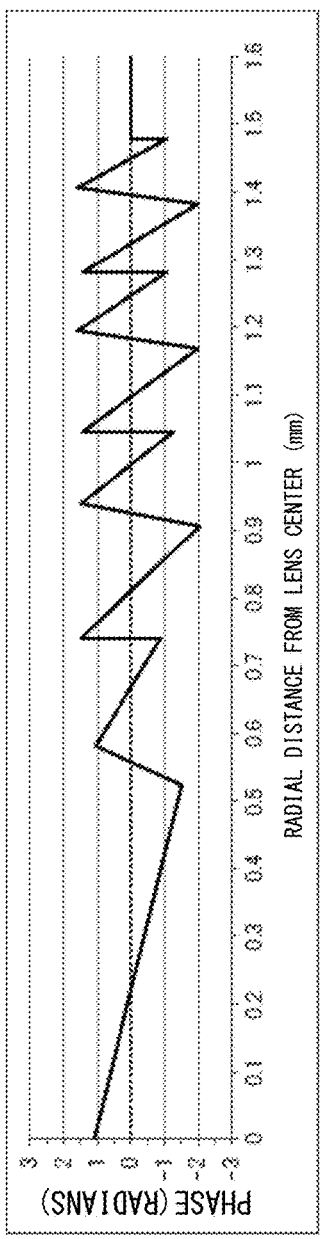
EXAMPLE 7
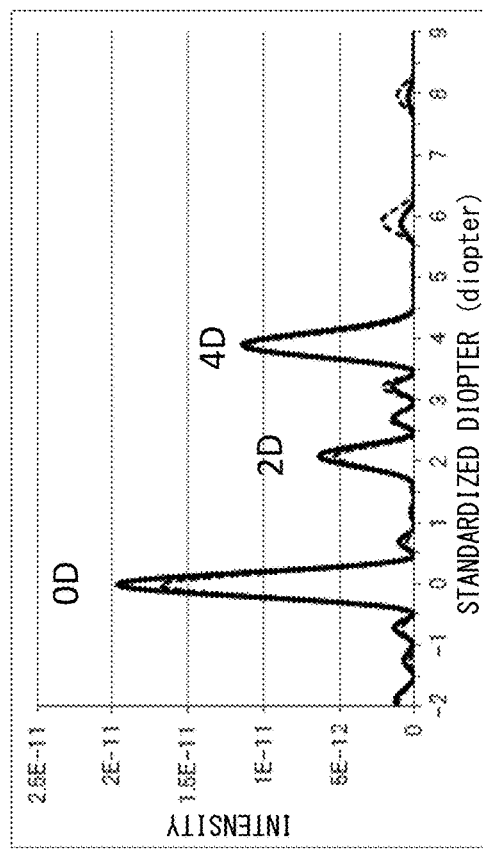
FIG.25B
EXAMPLE 7
+
COMPARATIVE
EXAMPLE 7
INTENSITY
DISTRIBUTION
ON OPTICAL AXIS

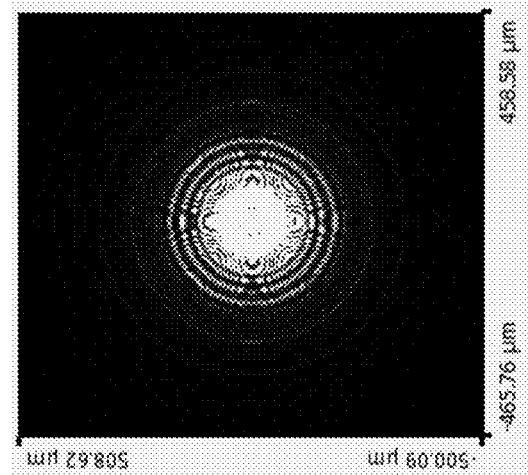
FIG.26B EXAMPLE 7
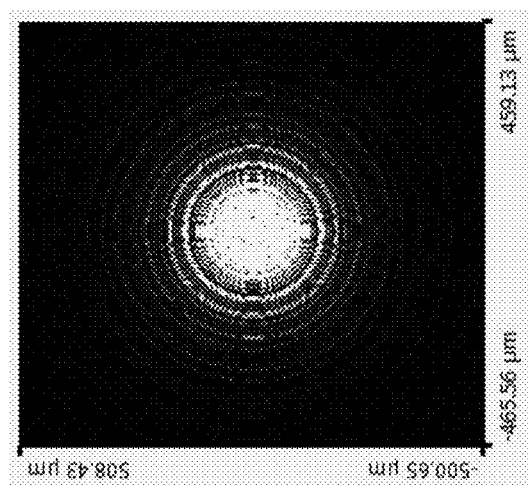
FIG.26A COMPARATIVE EXAMPLE 7
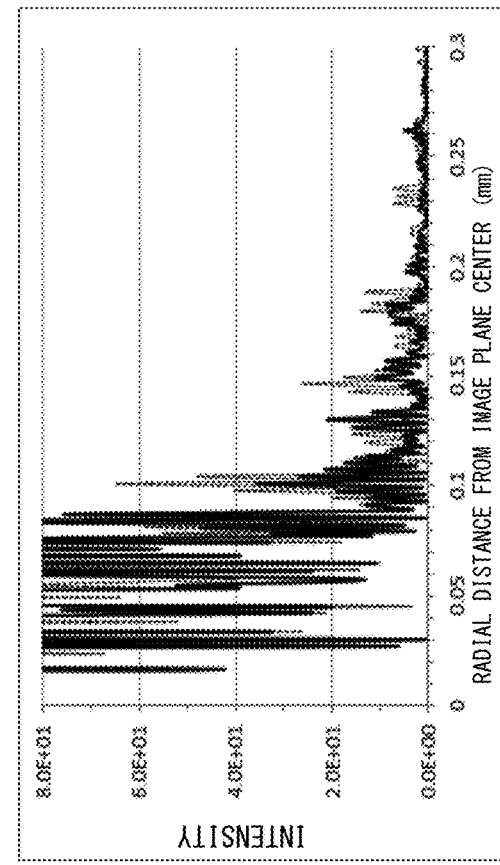
FIG.26C
EXAMPLE 7
+
COMPARATIVE
EXAMPLE 7
POINT SPREAD
FUNCTION
(PLOT DIAGRAM)

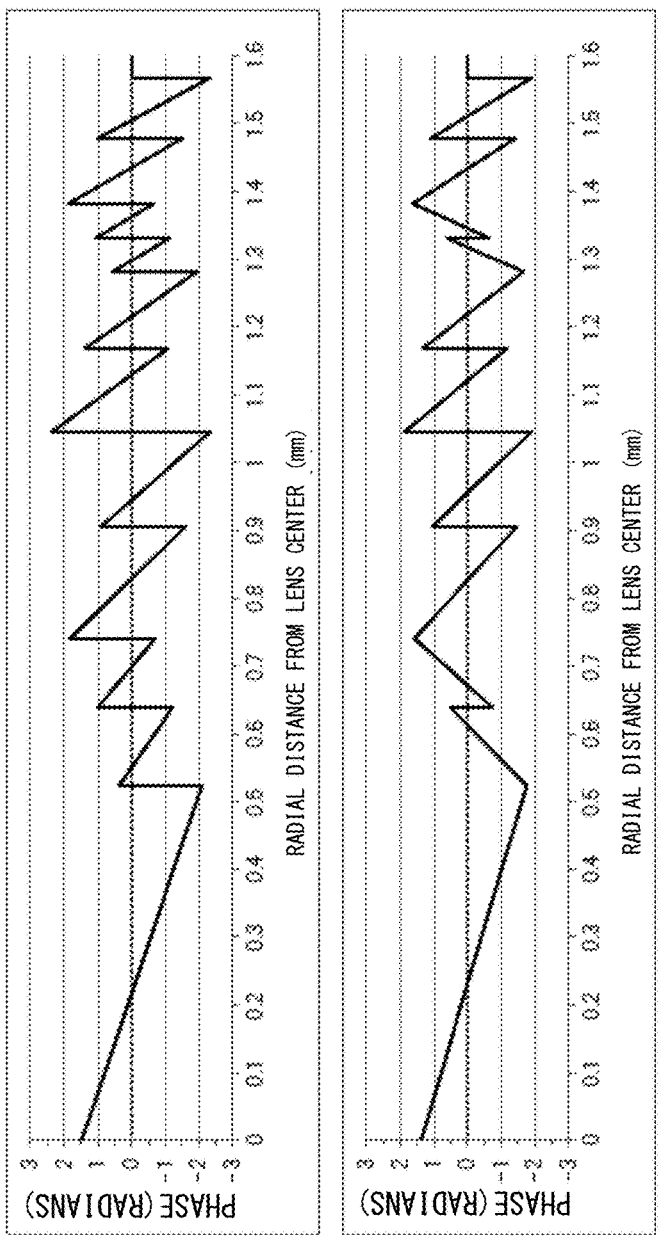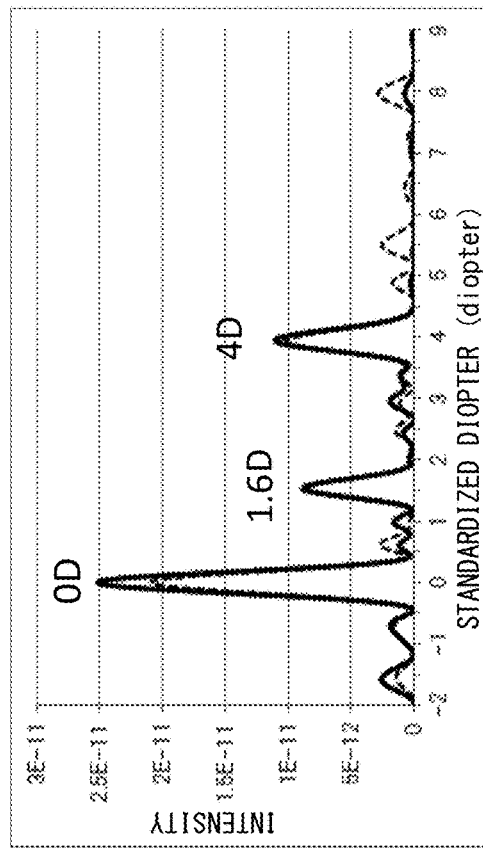
FIG.27A COMPARATIVE EXAMPLE 8
EXAMPLE 8
FIG.27B EXAMPLE 8 + COMPARATIVE EXAMPLE 8 INTENSITY DISTRIBUTION ON OPTICAL AXIS

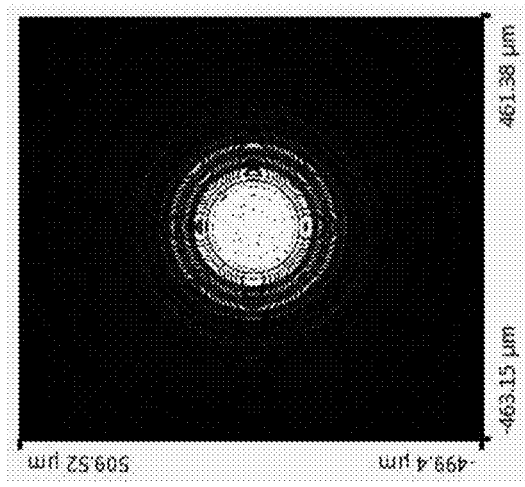
FIG. 28A COMPARATIVE EXAMPLE 8
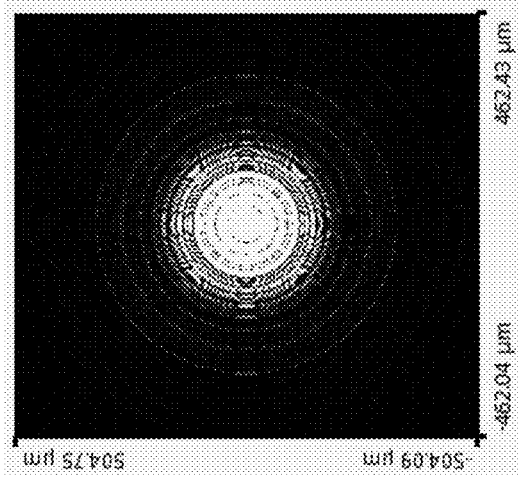
FIG. 28B EXAMPLE 8
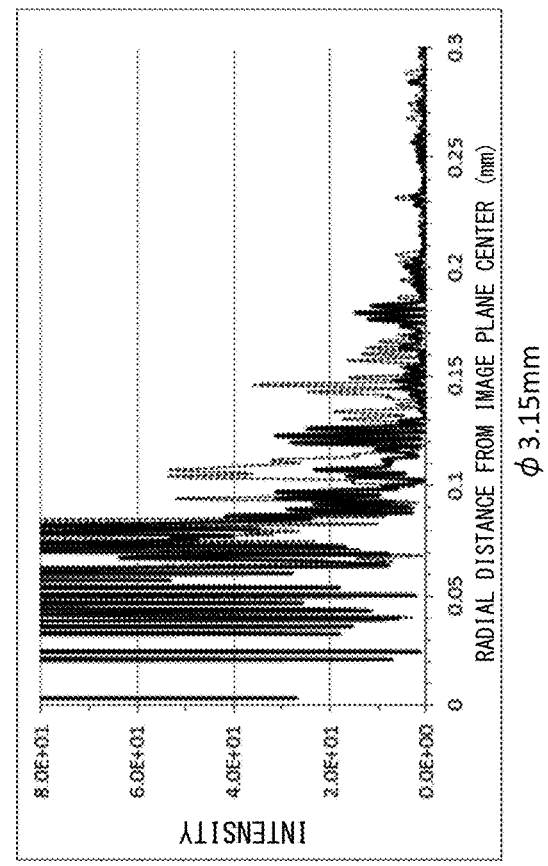
FIG. 28C
EXAMPLE 8
+
COMPARATIVE EXAMPLE 8
POINT SPREAD FUNCTION (PLOT DIAGRAM)

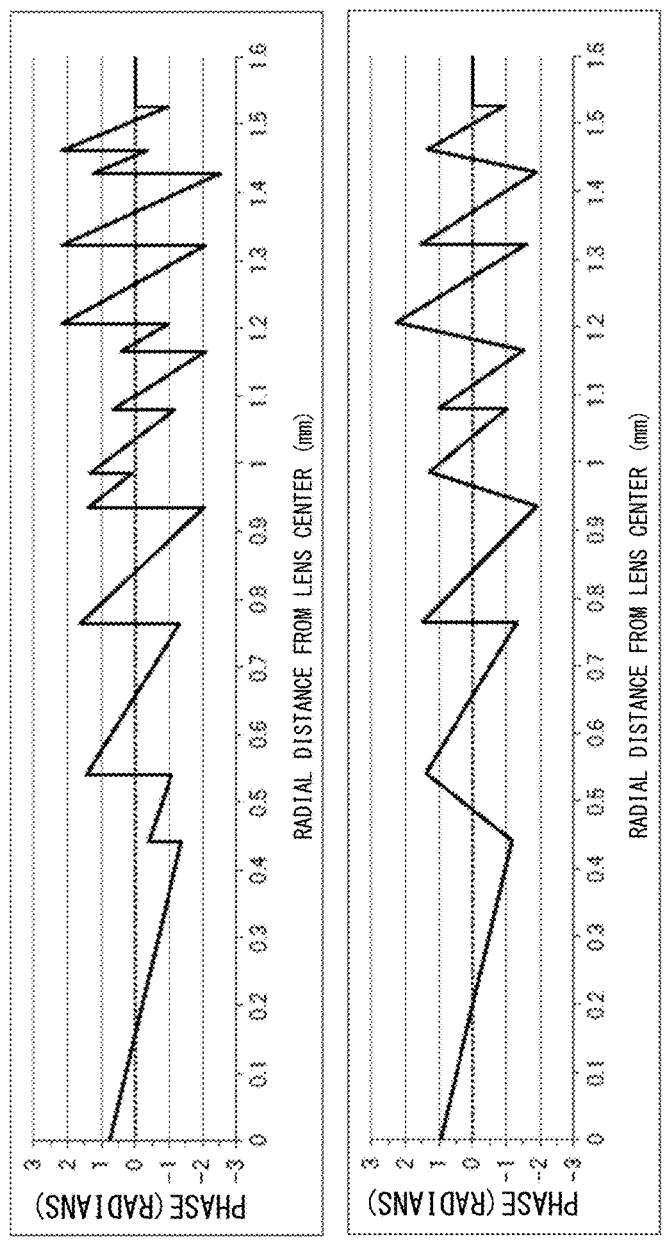
FIG.29A COMPARATIVE EXAMPLE 9
EXAMPLE 9
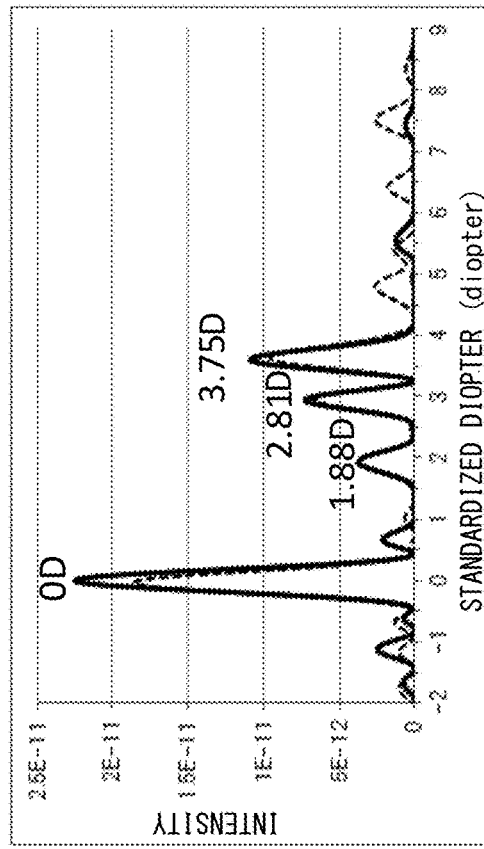
FIG.29B
EXAMPLE 9
+
COMPARATIVE EXAMPLE 9
INTENSITY DISTRIBUTION ON OPTICAL AXIS

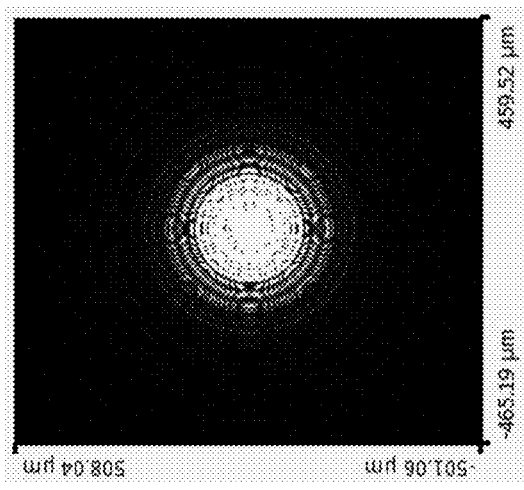
FIG. 30A COMPARATIVE EXAMPLE 9
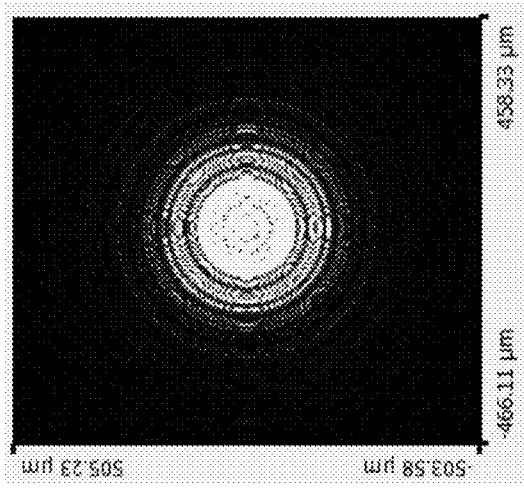
FIG. 30B EXAMPLE 9
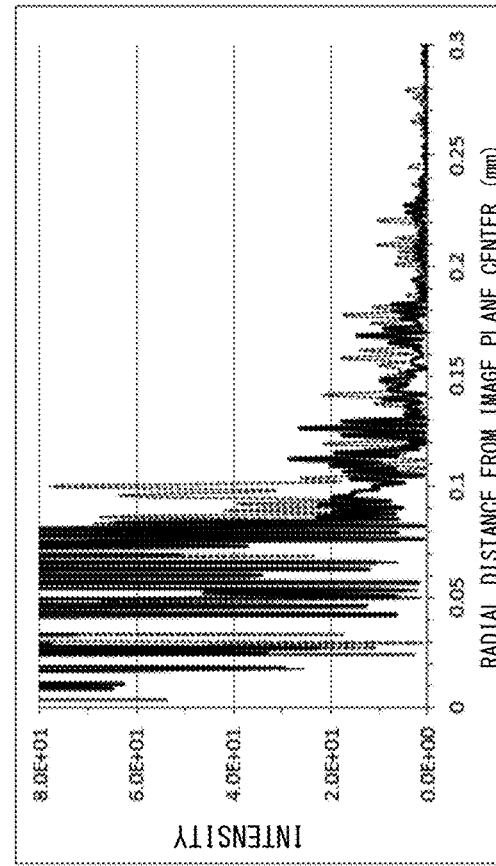
FIG. 30C
EXAMPLE 9
+
COMPARATIVE
EXAMPLE 9
POINT SPREAD
FUNCTION
(PLOT DIAGRAM)

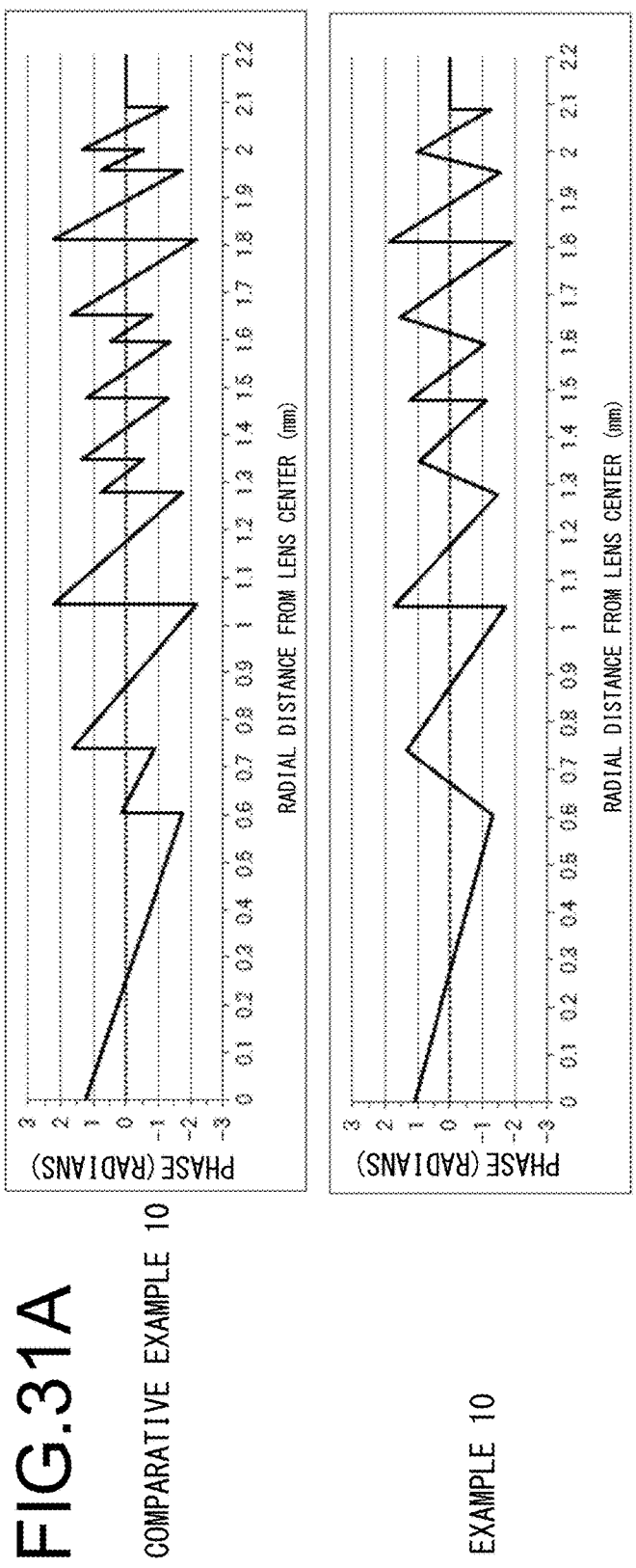
FIG.31A COMPARATIVE EXAMPLE 10
EXAMPLE 10
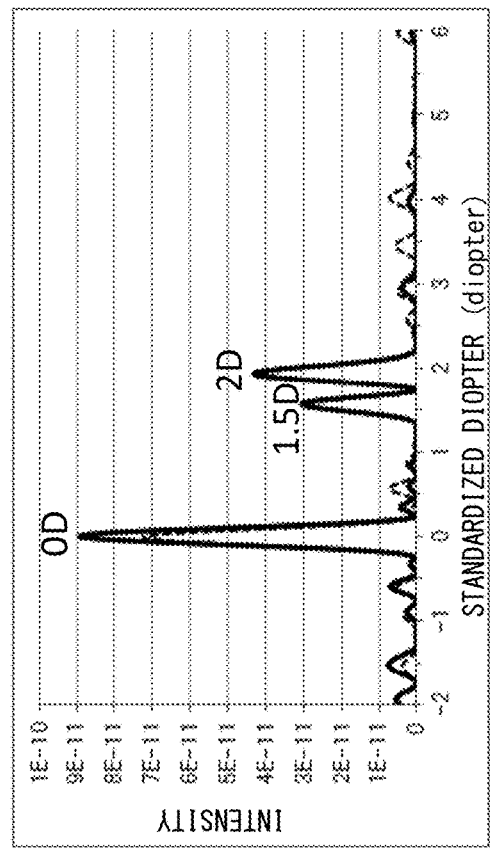
FIG.31B
EXAMPLE 10
+
COMPARATIVE
EXAMPLE 10
INTENSITY
DISTRIBUTION
ON OPTICAL AXIS

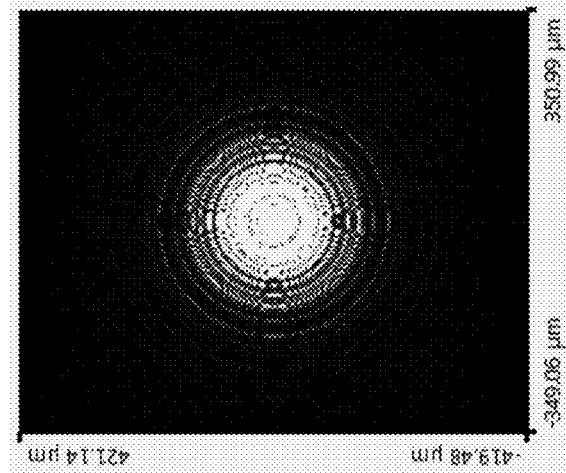
FIG.32B EXAMPLE 10
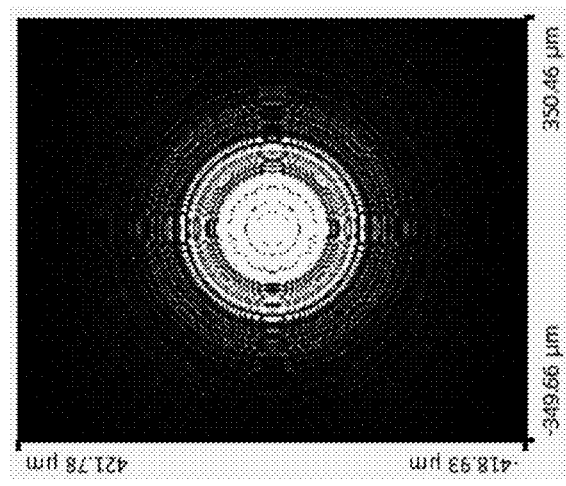
FIG.32A COMPARATIVE EXAMPLE 10
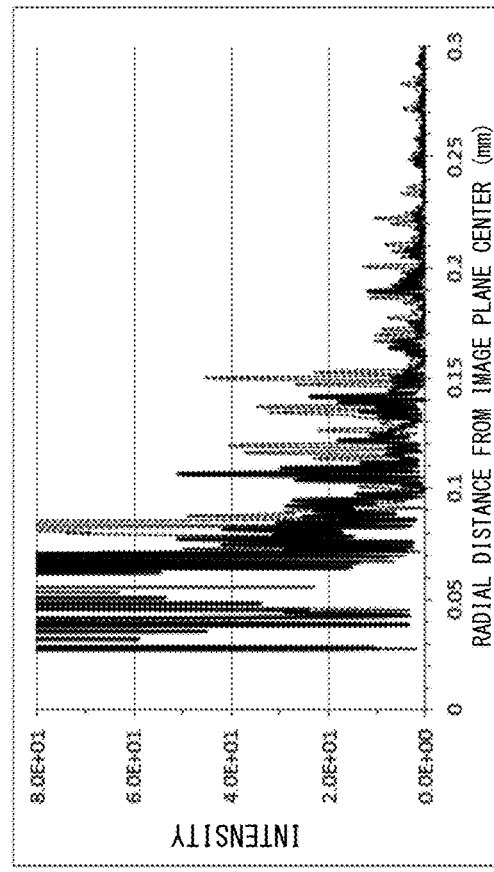
FIG.32C
EXAMPLE 10
+
COMPARATIVE
EXAMPLE 10
POINT SPREAD
FUNCTION
(PLOT DIAGRAM)

DIFFRACTIVE MULTI-FOCAL OPHTHALMIC LENS AND METHOD FOR MANUFACTURING DIFFRACTIVE MULTI-FOCAL OPHTHALMIC LENS

TECHNICAL FIELD

The present invention relates to an ophthalmic lens such as a contact lens, intraocular lens, etc., that is used for the human eye, and exhibits corrective action, etc. on the human eye optical system, and particularly relates to technology of a diffractive multi-focal ophthalmic lens for which a plurality of focal points are set.

BACKGROUND ART

Conventionally, as an optical element for correcting refractive abnormalities in the optical system of the human eye, or as a substitute optical element after removal of an crystalline lens, etc., an ophthalmic lens has been used. As specific ophthalmic lenses, in addition to eyeglasses lenses, there are contact lenses that are overlapped on the cornea, or ophthalmic lenses mounted directly in the human eye, such as an intraocular lens (IOL) used by being inserted intracapsularly in place of the intraocular crystalline lens, or a phakic intraocular lens (ICL) used by being inserted in the anterior chamber of the intraocular crystalline lens, etc., and these are widely used because they provide a wide field of view as well as reduce a sense of discomfort of vision.

However, in recent years, there is an increase in people continuing to use contact lenses when they have reached the age of having presbyopia. For people with presbyopia, their accommodation power decreases, so there is a symptom of having difficulty in focusing on nearby objects. Thus, multi-focal contact lenses which can also focus on nearby objects are needed for presbyopia patients. Also, for patients who have undergone cataract surgery, since the crystalline lens which is in charge of the accommodation function is removed, even if an intraocular lens is inserted as a substitute, the symptom of having difficulty in seeing close up remains. With the intraocular lens as well, it is necessary to have a multi-focal function having a plurality of focal points. In this way, the need for multi-focal ophthalmic lenses to reflect the aging society has increased even further in recent years.

As a method for realizing this multi-focal ophthalmic lens, known examples include a refractive multi-focal ophthalmic lens that forms a plurality of focal points based on the principle of refraction, and a diffractive multi-focal ophthalmic lens that forms a plurality of focal points based on the principle of diffraction. With the latter diffractive ophthalmic lens, provided are a plurality of diffractive structures which are formed in concentric circle form on the optical part of the lens, and a plurality of focal points are given by the mutual interference effect of light waves that pass through the plurality of diffractive structures (zones). Therefore, compared to a refractive lens that gives focal points using the refractive effect of light waves at the refracting surface comprising boundary surfaces with different refractive indexes, with the diffractive type multi-focal ophthalmic lens, there are advantages of being able to set a high lens power while inhibiting an increase in lens thickness, etc.

Generally, a diffractive multi-focal lens has a diffractive structure for which the diffractive zone pitches become gradually narrower toward the periphery from the lens center according to a rule called the Fresnel pitch, and multiple focal points are made by using the 0th order diffracted light and +1st order diffracted light generated from that structure. Normally, the 0th order diffracted light is used as the focal point for far vision, and +1st order diffracted light is used as the focal point for near vision. Using this diffracted light distribution, it is possible to make a bifocal lens having both far and near focal points.

Also, as in Japanese Unexamined Patent Publication No. JP-A-2010-158315 (Patent Document 1) disclosed by the present applicant, or in PCT Japanese Translation Patent Publication No. JP-A-2013-517822 (Patent Document 2), known are items for which the number of focal points are further increased, and as a result, it is possible to set focal points for intermediate vision in addition to those for far vision and for near vision.

Furthermore, in PCT Application No. PCT/JP2014/071113 (Patent Document 3), the present applicant proposed a diffractive multi-focal lens with improved degree of freedom of the focal point setting position for intermediate vision. The diffractive multi-focal lens of this earlier application is a diffractive multi-focal lens having a diffractive structure comprising a plurality of zones in a concentric circle form, characterized in that: the diffractive structure includes an overlapping region for which at least two zone profiles are overlapped on the same region in at least a portion thereof; and at the overlapping region, at least a portion of a first zone profile of the at least two zone profiles has a zone pitch expressed by Equation 1, and at least a portion of a second zone profile of the at least two zone profiles has a zone pitch expressed by Equation 2, and an addition power $P_1$ given by the first zone profile and an addition power $P_2$ given by the second zone profile are determined by a relational expression of Equation 3, where a and b are mutually different real numbers, and a value of a/b is a value that cannot be expressed by a natural number X or by 1/X.

$$r_n = \sqrt{r_1^2 + \frac{2\lambda(n-1)}{P_1}} \quad \text{Equation 1}$$

$\lambda$: Design wavelength
$r_n$: nth zone radius of the first zone profile
$r_1$: First zone radius of the first zone profile
$P_1$: Addition power of the first zone profile
n: Natural number $$r_m = \sqrt{r_1'^2 + \frac{2\lambda(m-1)}{P_2}} \quad \text{Equation 2}$$

$\lambda$: Design wavelength
$r_m$: mth zone radius of the second zone profile
$r_1'$: First zone radius of the second zone profile
$P_2$: Addition power of the second zone profile
m: Natural number $$P_2 = \frac{a}{b} \times P_1 \quad \text{Equation 3}$$

Also, with the diffractive multi-focal lens noted in Patent Document 3, for example in Equation 3, by setting a and b to be integers of zero or greater, an overlapped and synthesized profile has a repeated structure of periodic zones, and it is possible to more clearly realize the generation of at least three focal points over the entire area of the composite profile. Also, in this Equation 3, by setting a and b such that a/b>1/2, the focal point set at a position in the middle of far and near, can be set closer to the near focal point than the far focal point, and it is possible to set a focal point suitable for viewing a computer screen, for example.

However, with this kind of diffractive multi-focal lens, the existence of "halo" is pointed out as a problem particularly when used as an ophthalmic lens. "Halo" is a phenomenon of a band shaped or ring shaped light occurring around a light source when viewing a far light source at night, for example, and occurs particularly easily for point-shaped light sources such as a far street light or automobile headlight, bringing a decrease of visual acuity when using an ophthalmic lens at night.

In regards to the "halo" phenomenon, an explanation will be given with a specific example in the Embodiments for Carrying Out the Invention section described later, but as disclosed by the present inventor in Japanese Unexamined Patent Publication No. JP-A-2014-228660 (Patent Document 4) and International Publication No. WO2013/118176 (Patent Document 5), for example when focusing on the focal point for far vision, light from the far distance forms a main peak at the image plane center of the far focal point. Here, due to the fact that the lights intensified each other at other focal point positions, etc. also reach the image plane position of the far focal point, small peak groups caused by multi-order light exist around the main peak that forms the far focal point in the image plane of the far focal point, which conceivably cause halo. The intensity of this multi-order light is extremely small compared to the intensity of the main peak. However, when viewing an object in a dark environment or in a high contrast environment, this is thought to be recognized as a halo by being perceived by the retina with the high sensitivity of the human eye. Also, the problem of blurred vision having symptoms of vision as if being hazed when viewing an object or viewing an object in fog is also thought to be caused by the same mechanism as halo.

BACKGROUND ART DOCUMENTS

Patent Documents

Patent Document 1: JP-A-2010-158315

Patent Document 2: JP-A-2013-517822

Patent Document 3: PCT Application No. PCT/JP2014/071113

Patent Document 4: JP-A-2014-228660

Patent Document 5: WO2013/118176

SUMMARY OF THE INVENTION

Problem the Invention Attempts to Solve

It is an object of the present invention to provide a novel structure of, and a method for manufacturing, a diffractive multi-focal ophthalmic lens having effects such as improving halo.

Means for Solving the Problem

Definition of Phrases

Following, prior to explaining the present invention, phrases, etc., used with the present invention are defined as noted below.

Pupil Function

A pupil function is a lens characteristic function that describes the physical effect of a lens by which it is possible to change the state of light made incident on the lens, and in specific terms, is represented by the product of the amplitude function $A(r)$ and the exponential function of the phase function $\phi(r)$ as noted in Equation 4 below.

$$F(r)=A(r)e^{i\phi(r)} \qquad \text{Equation 4}$$

$F(r)$: Pupil function $A(r)$: Amplitude function $\phi(r)$: Phase function

Phase Function

A phase function is defined as the function that mathematically expresses the physical effect provided in a lens such as giving changes in the phase of incident light on a lens (position of wave peaks and valleys) using any method. The variable of the phase function is mainly expressed by position r in the radial direction from the center of the lens, and the phase of light made incident on the lens at the point of the position r undergoes a change by the phase function $\phi(r)$ and is emitted from the lens. In specific terms, this is represented by an r–φ coordinate system such as shown in FIG. 1. In this specification, phase is noted as φ, and the unit is radians. One wavelength of light is represented as $2\pi$ a radians, and a half wavelength as $\pi$ radians, for example. A distribution of phase in the overall area in which the phase function is provided expressed in the same coordinate system is called a phase profile, or is simply called a profile or zone profile. With an r axis of φ=0 as a reference line, this means that the light made incident at the point of φ=0 is emitted without changing the phase. Also, for this reference line, when a positive value is used for φ, this means that progress of the light is delayed by that phase amount, and when a negative value is used for φ, this means that progress of the light is advanced by that phase amount. In an actual ophthalmic lens, a refracting surface for which a diffractive structure is not given corresponds to this reference line (surface). Light undergoes a phase change based on this phase function and is emitted from the lens.

Amplitude Function

An amplitude function is the function expressed by $A(r)$ in Equation 4 noted above. In this specification, this is defined as a function that represents the change in the light transmission amount when passing through a lens. The variable of the amplitude function is represented as position r in the radial direction from the center of the lens, and represents the transmission rate of the lens at the point of position r. Also, the amplitude function is in a range of 0 or greater and 1 or less, which means that light is not transmitted at the point of $A(r)=0$, and that incident light is transmitted as it is without loss at the point of $A(r)=1$. In this specification, unless specifically noted otherwise, the amplitude function $A(r)$ is 1.

Zone

In this specification, a zone is used as the minimum unit in a diffractive structure or diffraction grating provided in a lens.

Zone Sequence

A zone sequence means a profile configured by a zone radius $r_n$ determined in Equation 5 below. In Equation 5, if any one of $r_1$, P, or λ is different, that is interpreted as a different, separate zone sequence. In this specification, the zone sequences are specified by a description noted as a zone sequence (1), a zone sequence (2), . . . etc.

$$r_n \sqrt{r_1^2 + \frac{2(n-1)\lambda}{P}} \qquad \text{Equation 5}$$

$r_n$: The nth zone radius of a certain zone sequence
$r_1$: The first zone radius of the zone sequence
n: Natural number
P: Addition power based on 1st order diffracted light of the zone sequence
λ: Design wavelength
  Blaze
  A Blaze is one mode that represents the diffraction grating configuration using phase function, and in addition to specifying each zone that configures the diffraction grating, the blaze specifies the phase change in light waves that pass through the each zone. For example, the blaze indicates the one in which the phase is changing in a roof-like shape. With the present invention, in FIGS. 2A-2D which show the phase on the plane orthogonal to the optical axis in cross section shape, the blaze is basically an item as shown in FIG. 2A for which there is linear change between the peaks (peak point or ridge line) and the valleys (bottom point or valley line) of a shed roof shape in one zone. However, the concept of the blaze shaped phase function of the present invention also includes an item as shown in FIG. 2B for which changes between the peaks and valleys occur in a parabolic curve, and an item as shown in FIG. 2C that appears as an irregular shape (square wave shape), etc. Moreover, as shown in FIG. 2D, an item for which the peaks and valleys are linked so that the change occurs as a part of a sine wave function, and an item for which the peaks and valleys are linked so that the change occurs within an interval with no extrema in a certain function, are also included in the concept of the blaze shaped phase function of the present invention because they function as a diffraction grating for the light waves and generate a plurality of focal points.
  In this specification, the peak and valley positions of the blaze for each zone of the diffraction grating is determined using the blaze inclination and the shift from the reference line (plane). Specifically, it is determined using the following constants. First, as shown in FIG. 2A, in the blaze of the ith zone (orbicular zone) in the radial direction from the center of the lens, basically, the absolute values of phase $\phi_{i-1}$ of the position of the inner diameter radius $r_{i-1}$ of the zone and phase $\phi_i$ of the position of the outer diameter radius $r_i$ are set to be equal relative to the reference surface (line), in other words, set to be $|\phi_i|=|\phi_{i-1}|$, and the inclination of the blaze is determined with the phase constant h determined by Equation 6.

$$h = \frac{\phi_{i-1} - \phi_i}{2\pi} \qquad \text{Equation 6}$$

Next, the phase shift τ is used to determine the shift in the φ direction of the blaze from the reference line (surface) with the inclination of the blaze maintained as it is. The mode of the blaze to which that shift is given is shown in FIG. 3. When the blaze is shifted upward (plus direction) from the reference line, τ is a positive value, and when it is shifted downward (minus direction) from the reference line, τ is a negative value. The unit of τ is radians. In this specification, where the typical phase notation of the inner diameter radius position and the outer diameter radius position of the zone based on this setting method are respectively $\phi_{i-1}'$ and $\phi_i'$, these are expressed by Equation 7 using the phase constant h and the phase shift τ.

$$\phi_{i-1}' = h \times \pi + \tau$$

$$\phi_i' = -h \times \pi + \tau \qquad \text{Equation 7}$$

In specific terms, when the phase constant h=0.5 and the phase shift τ is τ=0, $\phi_{i-1}'$ is determined as 1.5704 radians, and $\phi_i'$ is −1.5704 radians. If there is 1 radian of a phase shift in the positive direction, with τ=1, $\phi_{i-1}'$ is determined as 2.5704 radians, and $\phi_i'$ is −0.5704 radians. Also, when the phase constant is negative, for example when phase constant h is h=−0.5, and τ is τ=0, $\phi_{i-1}'$ is determined as −1.5704 radians, and $\phi_i'$ is 1.5704 radians. That is, this means that when the phase constant is of a positive sign, the blaze becomes a right downward inclination with the r-φ coordinate system, and when the phase constant is of a negative sign, it becomes a right upward inclination with that coordinate system. In the examples described later as well, the phases of the blaze peak and valley positions are noted using these phase constant and phase shift.
  Standard Profile
  As shown in FIG. 4, a standard profile comprises an overlapped structure of each zone of the plurality of zone sequences determined with Equation 5. Specifically, the plurality of zones configuring each of the zone sequences are arranged inside the same region configuring the diffraction grating in size sequence of the zone radius from the lens center toward the outer periphery. For example, FIG. 4 shows the zone arrangement of a standard profile comprising two zone sequences (1), (2).
  Present Invention Profile
  A present invention profile means the profile for which the blaze inclination of a specific zone is reversed according to the present invention with respect to the standard profile noted above. Specifically, the present invention profile is such that in the diffractive multi-focal ophthalmic lens of the structure according to the present invention, the optical characteristics of the diffraction grating are represented using a blaze shaped phase function. A "reversed inclination" of the present invention, specifically, an item for which the inclination of the blaze is reversed, is interpreted as being an item for which the blaze inclination sign (that is, the phase constant sign) is reversed, and does not require that the absolute value of the inclination be the same, and is not limited to being an item which is symmetrically reversed.
  Optical Axis
  An optical axis is a rotation symmetrical axis of the diffraction grating in the optical part of the lens, and in this specification, means the axis that goes through the lens center and extends into an object space and an image side space, with the lens geometrical center set to the optical center. The optical axis, which is the rotation symmetrical axis of the lens diffraction grating, can be offset in the radial direction from the lens geometrical center.
  0th Order Focal Point
  A 0th order focal point means the focal point position of 0th order diffracted light. Hereafter, +1st order focal point means the focal point position of +1st order diffracted light, +2nd order focal point means the focal point position of +2nd order diffracted light, and so forth.

Intensity Distribution on the Optical Axis

An intensity distribution on the optical axis is such that the intensity of the light after passing through the lens is plotted extending over the optical axis of the image side space.

Point Spread Function

A point spread function is the intensity distribution that forms on a certain image plane after light emitted from a point light source passes through a lens, and for which the intensity of the light with respect to the radial distance from the image plane center is plotted. In this specification, the image plane is a projection plane orthogonal to the optical axis.

Relief

As one practical and exemplary approach for realizing an ophthalmic lens using the phase function specified by the present invention profile, it is possible to realize a diffraction grating having a desired phase function by giving an actual form to the lens surface comprising a known lens material having a prescribed refractive index. Here, relief is the general term for a micro-uneven shaped structure formed on the lens surface obtained by reflecting the optical path length correlating to the phase determined by the phase profile and specifically converting to an actual form of a lens. A specific conversion formula for converting the blaze shaped phase to relief shape is determined in Equation 8 below, and it is possible to convert a step of the blaze phase to a relief step as an actual form.

$$\text{Relief step} = h \times \frac{\lambda}{n_s - n_m} \quad \text{Equation 8}$$

h: Phase constant
λ: Design wavelength
$n_s$: Refractive index of lens base material
$n_m$: Refractive index of medium covering the lens Here, with the circumstances noted in the Background Art section as the background, the present invention has the purpose of addressing the problems noted in the Problem the Invention Attempts to Solve section, and characteristic modes of the present invention are represented as noted below using the phrases described above.

First, the present invention which relates to a diffractive multi-focal ophthalmic lens provides a diffractive multi-focal ophthalmic lens of a novel structure according to any of the following first to fourth modes. Also, with the diffractive multi-focal ophthalmic lens of the present invention having a structure according to the first to fourth modes, as is also clear from the descriptions of each example described later, it is possible to suppress the peaks of multi-order light while ensuring the light intensity of the target focal point positions, thus exhibiting a halo reduction effect.

A first mode of the present invention provides a diffractive multi-focal ophthalmic lens for which a diffraction grating comprising a blaze shaped phase function is configured by a plurality of concentric zones for which a plurality of zone sequences with a zone radius given by Equation 9 are overlapped such that a plurality of focal points are set, the diffractive multi-focal ophthalmic lens characterized in that: at least one of the zones configuring the diffraction grating, the zone having a zone pitch Δr that satisfies Δr≤0.5×Δ$r_{max}$ with respect to a zone pitch Δ$r_{max}$ for a maximum pitch zone having a maximum zone pitch among the plurality of concentric zones, serves as an adjustment zone; and in the adjustment zone, a blaze shaped phase function for which an inclination is reversed with respect to an inclination of the blaze shaped phase function in the maximum pitch zone is set.

$$r_n = \sqrt{r_1^2 + \frac{2(n-1)\lambda}{P}} \quad \text{Equation 9}$$

$r_n$: nth zone radius of a certain zone sequence
$r_1$: 1st zone radius of the zone sequence
n: Natural number
P: Addition power based on 1st order diffracted light of the zone sequence
λ: Design wavelength A second mode of the present invention provides a diffractive multi-focal ophthalmic lens for which a diffraction grating comprising a blaze shaped phase function is configured by a plurality of concentric zones for which a plurality of zone sequences with a zone radius given by Equation 10 are overlapped such that a plurality of focal points are set, the diffractive multi-focal ophthalmic lens characterized in that: at least one of the zones configuring the diffraction grating, the zone having a zone area S that satisfies S≤0.5×$S_{max}$ with respect to a zone area $S_{max}$ for a maximum area zone having a maximum zone area among the plurality of concentric zones, serves as an adjustment zone; and in the adjustment zone, a blaze shaped phase function for which an inclination is reversed with respect to an inclination of the blaze shaped phase function in the maximum area zone is set.

$$r_n = \sqrt{r_1^2 + \frac{2(n-1)\lambda}{P}} \quad \text{Equation 10}$$

$r_n$: nth zone radius of a certain zone sequence
$r_1$: 1st zone radius of the zone sequence
n: Natural number
P: Addition power based on 1st order diffracted light of the zone sequence
λ: Design wavelength A third mode of the present invention provides a diffractive multi-focal ophthalmic lens for which a diffraction grating comprising a blaze shaped phase function is configured by a plurality of concentric zones for which a plurality of zone sequences with a zone radius given by Equation 11 are overlapped such that a plurality of focal points are set, the diffractive multi-focal ophthalmic lens characterized in that: at least one of the zones configuring the diffraction grating, the zone having a half-value width ΔD that satisfies ΔD≥2×Δ$D_{min}$ with respect to a half-value width Δ$D_{min}$ in a narrowest intensity distribution zone for which a half-value width of an intensity distribution on an optical axis of a light emitted from that zone is narrowest among the plurality of concentric zones, serves as an adjustment zone; and in the adjustment zone, a blaze shaped phase function for which an inclination is reversed with respect to an inclination of the blaze shaped phase function in the narrowest intensity distribution zone is set.

$$r_n = \sqrt{r_1^2 + \frac{2(n-1)\lambda}{P}} \quad \text{Equation 11}$$

$r_n$: nth zone radius of a certain zone sequence
$r_1$: 1st zone radius of the zone sequence
n: Natural number
P: Addition power based on 1st order diffracted light of the zone sequence
$\lambda$: Design wavelength A fourth mode of the present invention provides a diffractive multi-focal ophthalmic lens for which a diffraction grating comprising a blaze shaped phase function is configured by a plurality of concentric zones for which a plurality of zone sequences with a zone radius given by Equation 12 are overlapped such that a plurality of focal points are set, the diffractive multi-focal ophthalmic lens characterized in that at least one adjustment zone is provided, the adjustment zone being described in at least one of (A), (B), and (C) listed below:

(A) an adjustment zone defined by at least one of the zones configuring the diffraction grating, the zone having a zone pitch $\Delta r$ that satisfies $\Delta r \leq 0.5 \times \Delta r_{max}$ with respect to a zone pitch $\Delta r_{max}$ for a maximum pitch zone having a maximum zone pitch among the plurality of concentric zones, the adjustment zone being such that a blaze shaped phase function for which an inclination is reversed with respect to an inclination of the blaze shaped phase function in the maximum pitch zone is set;

(B) an adjustment zone defined by at least one of the zones configuring the diffraction grating, the zone having a zone area S that satisfies $S \leq 0.5 \times S_{max}$ with respect to a zone area $S_{max}$ for a maximum area zone having a maximum zone area among the plurality of concentric zones, the adjustment zone being such that a blaze shaped phase function for which an inclination is reversed with respect to an inclination of the blaze shaped phase function in the maximum area zone is set; and (C) an adjustment zone defined by at least one of the zones configuring the diffraction grating, the zone having a half-value width $\Delta D$ that satisfies $\Delta D \geq 2 \times \Delta D_{min}$ with respect to a half-value width $\Delta D_{min}$ in a narrowest intensity distribution zone for which a half-value width of an intensity distribution on an optical axis of a light emitted from that zone is narrowest among the plurality of concentric zones, the adjustment zone being such that a blaze shaped phase function for which an inclination is reversed with respect to an inclination of the blaze shaped phase function in the narrowest intensity distribution zone is set.

$$r_n = \sqrt{r_1^2 + \frac{2(n-1)\lambda}{P}} \quad \text{Equation 12}$$

$r_n$: nth zone radius of a certain zone sequence
$r_1$: 1st zone radius of the zone sequence
n: Natural number
P: Addition power based on 1st order diffracted light of the zone sequence
$\lambda$: Design wavelength Also, with the diffractive multi-focal ophthalmic lens of the aforementioned fourth mode, as shown in examples described later, it is preferable that the adjustment zone be selected and set according to the fifth to seventh modes hereafter. As a result, it is possible to more efficiently and appropriately perform selection of the adjustment zone when obtaining an effect such as halo reduction according to the present invention.

A fifth mode of the present invention provides the diffractive multi-focal ophthalmic lens according to the fourth mode, wherein in a diffraction grating region in which the diffraction grating is provided, the adjustment zone is positioned and set to a radially inner side of a radial center of the diffraction grating region, and the adjustment zone is the adjustment zone that satisfies conditions described in (B) of the fourth mode.

A sixth mode of the present invention provides the diffractive multi-focal ophthalmic lens according to the fourth or fifth mode, wherein in a diffraction grating region in which the diffraction grating is provided, the adjustment zone is positioned and set to a radially outer side of a radial center of the diffraction grating region, and the adjustment zone is the adjustment zone that satisfies conditions described in (A) of the fourth mode.

A seventh mode of the present invention provides the diffractive multi-focal ophthalmic lens according to any of the fourth to sixth modes, wherein in a diffraction grating region in which the diffraction grating is provided, the at least one adjustment zone is set to each of a radially inner side and a radially outer side of a radial center of the diffraction grating region, the adjustment zone set to the radially inner side is the adjustment zone that satisfies at least conditions described in (B) of the fourth mode, and the adjustment zone set to the radially outer side is the adjustment zone that satisfies at least conditions described in (A) of the fourth mode.

Also, with the diffractive multi-focal ophthalmic lens of each mode according to the present invention described above, as shown in the examples described later, the eighth to tenth modes hereafter can be suitably used in combination as necessary. As a result, for example, it is possible to obtain even more advantageously the effects of ensuring light intensity of the focal point position or suppressing multi-order light, or to make it easier to realize the diffraction grating provided with the target optical characteristics, etc.

An eighth mode of the present invention provides the diffractive multi-focal ophthalmic lens according to any of the first to seventh modes, wherein in a diffraction grating region in which the diffraction grating is provided, a total number of the adjustment zone is less than ½ a total number of the zones in the diffraction grating region.

A ninth mode of the present invention provides the diffractive multi-focal ophthalmic lens according to any of the first to eighth modes, wherein the phase function set in the adjustment zone is a blaze shaped phase function that does not form a valley point between the adjustment zone and a neighboring zone that neighbors the adjustment zone. The valley point that is not formed in the phase function according to this mode is the valley point between the adjustment zone and the neighboring zone that neighbors the adjustment zone at one side. For example, it is the valley point between each zone for which i=2, 5, 8, 11 in the standard profile of Examples 1, 2 described later and the neighboring zone at the right side thereof. Also, as shown in Examples 2-2, 2-3, 2-4, etc., for the blaze shaped phase function that does not form the valley point between the adjustment zone and the neighboring zone, in addition to a phase function that connects the valley part and the peak part between the neighboring zones that neighbor the adjustment zone at both sides, it is also possible to adopt a blaze shaped phase function for which the connecting positions do not match either the valley part or the peak part of the neighboring zones, or the connecting positions match only one of the valley part and the peak part, etc.

A tenth mode of the present invention provides the diffractive multi-focal ophthalmic lens according to any of the first to ninth modes, wherein the lens has optical characteristics in which an intensity of peak of a multi-order light caused by the diffraction grating is low with respect to that of a standard diffractive multi-focal lens having a standard profile for which the blaze shaped phase function for which the inclination is reversed in the adjustment zone is not set.

An eleventh mode of the present invention provides the diffractive multi-focal ophthalmic lens according to any of the first to tenth modes, wherein the diffraction grating comprising the blaze shaped phase function is set as a relief structure reflecting an optical path length correlating to a phase.

A twelfth mode of the present invention provides the diffractive multi-focal ophthalmic lens according to any of the first to eleventh modes, wherein one of the plurality of focal points serves as a focal point for far vision, and the focal point for far vision is given by a 0th order diffracted light of the diffraction grating comprising the blaze shaped phase function.

Furthermore, a thirteenth mode of the present invention provides a method for manufacturing a diffractive multi-focal ophthalmic lens comprising: a step of setting a diffraction grating for which a plurality of focal points are set, with a blaze shaped phase function, using a plurality of concentric zones for which a plurality of zone sequences with a zone radius given by Equation 13 are overlapped; a step of setting an adjustment zone, the adjustment zone being described in at least one of (A), (B), and (C) listed below; and a step of forming the diffraction grating provided with the plurality of zones including the adjustment zone in an optical material.

(A) an adjustment zone defined by at least one of the zones configuring the diffraction grating, the zone having a zone pitch $\Delta r$ that satisfies $\Delta r \leq 0.5 \times \Delta r_{max}$ with respect to a zone pitch $\Delta r_{max}$ for a maximum pitch zone having a maximum zone pitch among the plurality of concentric zones, the adjustment zone being such that a blaze shaped phase function for which an inclination is reversed with respect to an inclination of the blaze shaped phase function in the maximum pitch zone is set.

(B) an adjustment zone defined by at least one of the zones configuring the diffraction grating, the zone having a zone area S that satisfies $S \leq 0.5 \times S_{max}$ with respect to a zone area $S_{max}$ for a maximum area zone having a maximum zone area among the plurality of concentric zones, the adjustment zone being such that a blaze shaped phase function for which an inclination is reversed with respect to an inclination of the blaze shaped phase function in the maximum area zone is set.

(C) an adjustment zone defined by at least one of the zones configuring the diffraction grating, the zone having a half-value width $\Delta D$ that satisfies $\Delta D \geq 2 \times \Delta D_{min}$ with respect to a half-value width $\Delta D_{min}$ in a narrowest intensity distribution zone for which a half-value width of an intensity distribution on an optical axis of a light emitted from that zone is narrowest among the plurality of concentric zones, the adjustment zone being such that a blaze shaped phase function for which an inclination is reversed with respect to an inclination of the blaze shaped phase function in the narrowest intensity distribution zone is set.

$$r_n = \sqrt{r_1^2 + \frac{2(n-1)\lambda}{P}} \qquad \text{Equation 13}$$

$r_n$: nth zone radius of a certain zone sequence
$r_1$: 1st zone radius of the zone sequence
n: Natural number
P: Addition power based on 1st order diffracted light of the zone sequence
$\lambda$: Design wavelength According to the method of the present invention, it is possible to obtain a diffractive multi-focal ophthalmic lens having a novel structure according to any of the first to twelfth modes, for example, and of a novel structure which is able to suppress the peaks of multi-order light while ensuring the light intensity of the target focal point positions, thus reducing halo.

Effect of the Invention

As can be understood from the explanation described above and the examples described later, according to the present invention, it is possible to realize a diffractive multi-focal ophthalmic lens of a novel structure which is able to improve the quality of vision with halo suppressed compared to a diffractive multi-focal ophthalmic lens of a conventional structure.

BRIEF DESCRIPTION OF THE DRAWINGS

FIG. 5A is the standard profile, FIG. 5B is the intensity distribution on the optical axis of the standard profile shown in FIG. 5A, FIG. 5C is the point spread function in a 0th order focal point image plane of the standard profile shown in FIG. 5A, and FIG. 5D is a plot diagram of the point spread function in the image plane of the standard profile shown in FIG. 5A.

FIGS. 6A-6C are drawings for explaining the basic structure and characteristics of the diffractive multi-focal ophthalmic lens according to the present invention, where FIG. 6A is a drawing showing a comparison of the present invention profile with the standard profile noted in FIGS. 5A-5D, FIG. 6B is a drawing showing a comparison of the intensity distribution on the optical axis of the present invention profile shown in FIG. 6A with that of the standard profile, and FIG. 6C is the point spread function in the image plane of the present invention profile shown in FIG. 6A.

FIG. 7A is a drawing showing the present invention profile of Example 1 together with that of Comparative Example 1, FIG. 7B is a drawing showing the intensity distribution on the optical axis of Example 1 together with that of Comparative Example 1, FIG. 7C is a drawing of the point spread function in the image plane of Comparative Example 1 corresponding to FIG. 6C showing the point spread function of Example 1, and FIG. 7D shows a plot diagram of the point spread function in the image plane of Example 1 together with that of Comparative Example 1.

FIG. 8A is a drawing showing the present invention profile of Example 2 together with that of Comparative Example 2, and FIG. 8B shows the intensity distribution on the optical axis of Example 2 together with that of Comparative Example 2.

FIGS. 9A-9C are drawings for explaining the characteristics of the diffractive multi-focal ophthalmic lens as Example 2 of the present invention, where FIG. 9A is the point spread function in the image plane of Comparative Example 2, FIG. 9B is the point spread function in the image plane of Example 2, and FIG. 9C is a drawing showing a plot diagram of the point spread function in the image plane of Example 2 together with that of Comparative Example 2.

FIG. 10A is a drawing showing the present invention profile of Example 2-2, FIG. 10B is a drawing showing the intensity distribution on the optical axis of Example 2-2 together with that of Comparative Example 2, FIG. 10C is the point spread function in the image plane of Example 2-2, and FIG. 10D shows a plot diagram of the point spread function in the image plane of Example 2-2 together with that of Comparative Example 2.

FIG. 11A is a drawing showing the present invention profile of Example 2-3, FIG. 11B is a drawing showing the intensity distribution on the optical axis of Example 2-3 together with that of Comparative Example 2, FIG. 11C is the point spread function in the image plane of Example 2-3, and FIG. 11D shows a plot diagram of the point spread function in the image plane of Example 2-3 together with that of Comparative Example 2.

FIG. 12A is a drawing showing the present invention profile of Example 2-4, FIG. 12B is a drawing showing the intensity distribution on the optical axis of Example 2-4 together with that of Comparative Example 2, FIG. 12C is the point spread function in the image plane of Example 2-4, and FIG. 12D shows a plot diagram of the point spread function in the image plane of Example 2-4 together with that of Comparative Example 2.

FIG. 13A is a drawing showing the present invention profile of Example 2-5, and FIG. 13B is a drawing showing the intensity distribution on the optical axis of Example 2-5 together with that of Comparative Example 2.

FIG. 14A is a drawing showing the present invention profile of Example 2-6, and FIG. 14B is a drawing showing the intensity distribution on the optical axis of Example 2-6 together with that of Comparative Example 2.

FIGS. 15A-15C are drawings each showing an example of the structure of the diffractive multifocal lens as another example configured according to the present invention, where FIG. 15A is a drawing showing the present invention profile set in the diffractive multi-focal lens as Example 2-7 of the present invention, FIG. 15B is a drawing showing the present invention profile set in the diffractive multi-focal ophthalmic lens as Example 2-8 of the present invention, and FIG. 15C is a drawing showing the present invention profile set in the diffractive multi-focal ophthalmic lens as Example 2-9 of the present invention.

FIG. 16A shows the intensity distribution on the optical axis of zone numbers 3, 4, 9, and 10, FIG. 16B shows the intensity distribution on the optical axis of zone numbers 1, 6, 7, and 12, and FIG. 16C shows the intensity distribution on the optical axis of zone numbers 2, 5, 8, and 11.

FIGS. 17A and 17B are drawings for explaining the structure and characteristics of the diffractive multi-focal ophthalmic lens as Example 3 of the present invention, where FIG. 17A is a drawing showing the present invention profile of Example 3 together with that of Comparative Example 3, and FIG. 17B shows the intensity distribution on the optical axis of Example 3 together with that of Comparative Example 3.

FIGS. 18A-18C are drawings for explaining the characteristics of the diffractive multi-focal ophthalmic lens as Example 3 of the present invention, where FIG. 18A is the point spread function in the image plane of Comparative Example 3, FIG. 18B is the point spread function in the image plane of Example 3, and FIG. 18C is a drawing showing a plot diagram of the point spread function in the image plane of Example 3 together with that of Comparative Example 3.

FIG. 19A is a drawing showing the present invention profile of Example 4 together with that of Comparative Example 4, and FIG. 19B shows the intensity distribution on the optical axis of Example 4 together with that of Comparative Example 4.

FIGS. 20A-20C are drawings for explaining the characteristics of the diffractive multi-focal ophthalmic lens as Example 4 of the present invention, where FIG. 20A is the point spread function in the image plane of Comparative Example 4, FIG. 20B is the point spread function in the image plane of Example 4, and FIG. 20C is a drawing showing a plot diagram of the point spread function in the image plane of Example 4 together with that of Comparative Example 4.

FIGS. 21A and 21B are drawings for explaining the structure and characteristics of the diffractive multi-focal ophthalmic lens as Example 5 of the present invention, where FIG. 21A is a drawing showing the present invention profile of Example 5 together with that of Comparative Example 5, and FIG. 21B shows the intensity distribution on the optical axis of Example 5 together with that of Comparative Example 5.

FIGS. 22A-22C are drawings for explaining the characteristics of the diffractive multi-focal ophthalmic lens as Example 5 of the present invention, where FIG. 22A is the point spread function in the image plane of Comparative Example 5, FIG. 22B is the point spread function in the image plane of Example 5, and FIG. 22C is a drawing showing a plot diagram of the point spread function in the image plane of Example 5 together with that of Comparative Example 5.

FIGS. 23A and 23B are drawings for explaining the structure and characteristics of the diffractive multi-focal ophthalmic lens as Example 6 of the present invention, where FIG. 23A is a drawing showing the present invention profile of Example 6 together with that of Comparative Example 6, and FIG. 23B shows the intensity distribution on the optical axis of Example 6 together with that of Comparative Example 6.

FIGS. 24A-24C are drawings for explaining the characteristics of the diffractive multi-focal ophthalmic lens as Example 6 of the present invention, where FIG. 24A is the point spread function in the image plane of Comparative Example 6, FIG. 24B is the point spread function in the image plane of Example 6, and FIG. 24C is a drawing showing a plot diagram of the point spread function in the image plane of Example 6 together with that of Comparative Example 6.

FIGS. 25A and 25B are drawings for explaining the structure and characteristics of the diffractive multi-focal ophthalmic lens as Example 7 of the present invention, where FIG. 25A is a drawing showing the present invention profile of Example 7 together with that of Comparative Example 7, and FIG. 25B shows the intensity distribution on the optical axis of Example 7 together with that of Comparative Example 7.

FIGS. 26A-26C are drawings for explaining the characteristics of the diffractive multi-focal ophthalmic lens as Example 7 of the present invention, where FIG. 26A is the point spread function in the image plane of Comparative Example 7, FIG. 26B is the point spread function in the image plane of Example 7, and FIG. 26C is a drawing showing a plot diagram of the point spread function in the image plane of Example 7 together with that of Comparative Example 7.

FIGS. 27A and 27B are drawings for explaining the structure and characteristics of the diffractive multi-focal ophthalmic lens as Example 8 of the present invention, where FIG. 27A is a drawing showing the present invention profile of Example 8 together with that of Comparative Example 8, and FIG. 27B shows the intensity distribution on the optical axis of Example 8 together with that of Comparative Example 8.

FIGS. 28A-28C are drawings for explaining the characteristics of the diffractive multi-focal ophthalmic lens as Example 8 of the present invention, where FIG. 28A is the point spread function in the image plane of Comparative Example 8, FIG. 28B is the point spread function in the image plane of Example 8, and FIG. 28C is a drawing showing a plot diagram of the point spread function in the image plane of Example 8 together with that of Comparative Example 8.

FIGS. 29A and 29B are drawings for explaining the structure and characteristics of the diffractive multi-focal ophthalmic lens as Example 9 of the present invention, where FIG. 29A is a drawing showing the present invention profile of Example 9 together with that of Comparative Example 9, and FIG. 29B shows the intensity distribution on the optical axis of Example 9 together with that of Comparative Example 9.

FIGS. 30A-30C are drawings for explaining the characteristics of the diffractive multi-focal ophthalmic lens as Example 9 of the present invention, where FIG. 30A is the point spread function in the image plane of Comparative Example 9, FIG. 30B is the point spread function in the image plane of Example 9, and FIG. 30C is a drawing showing a plot diagram of the point spread function in the image plane of Example 9 together with that of Comparative Example 9.

FIGS. 31A and 31B are drawings for explaining the structure and characteristics of the diffractive multi-focal ophthalmic lens as Example 10 of the present invention, where FIG. 31A is a drawing showing the present invention profile of Example 10 together with that of Comparative Example 10, and FIG. 31B shows the intensity distribution on the optical axis of Example 10 together with that of Comparative Example 10.

FIGS. 32A-32C are drawings for explaining the characteristics of the diffractive multi-focal ophthalmic lens as Example 10 of the present invention, where FIG. 32A is the point spread function in the image plane of Comparative Example 10, FIG. 32B is the point spread function in the image plane of Example 10, and FIG. 32C is a drawing showing a plot diagram of the point spread function in the image plane of Example 10 together with that of Comparative Example 10.

EMBODIMENTS FOR CARRYING OUT THE INVENTION

Figure 1:
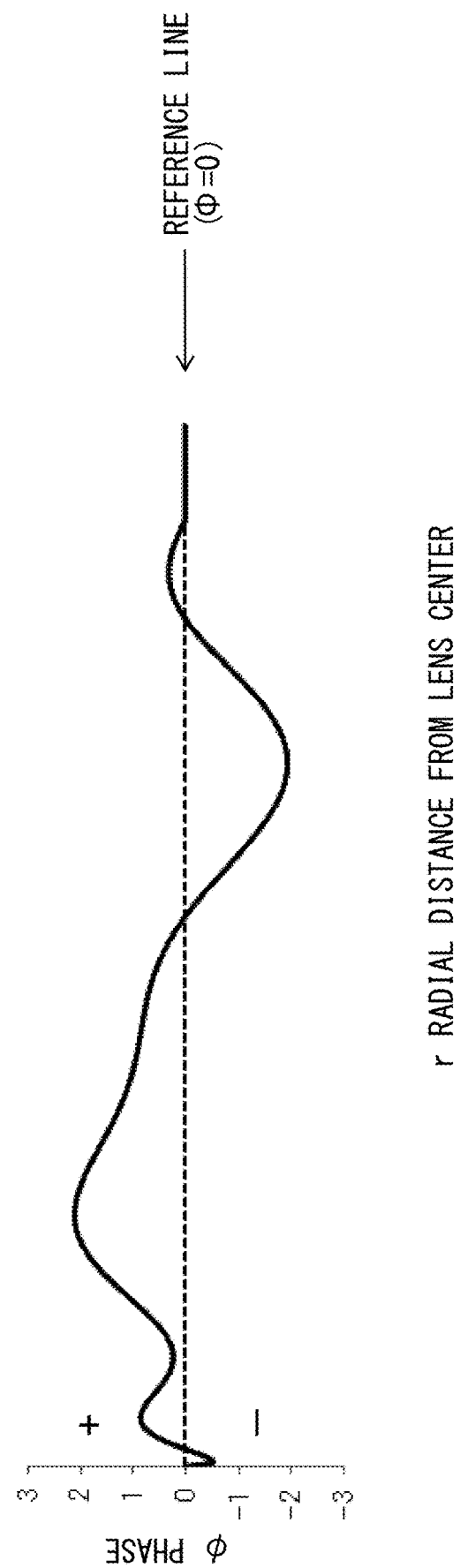
FIG. 1 is a graph of a phase function in the r–ϕ coordinate system with the phase ϕ of a phase modulation structure provided in the diffractive lens expressed as the relationship with the lens radial direction position r.
Figures 2A, 2B, 2C, 2D:
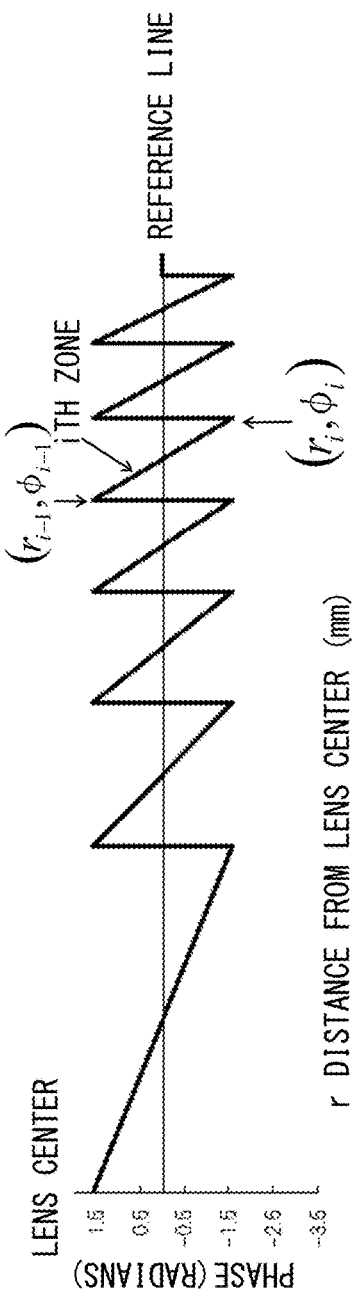
FIGS. 2A-2D are graphs each showing an example of a blaze as a mode of the phase function in the diffractive lens.
Figure 3:
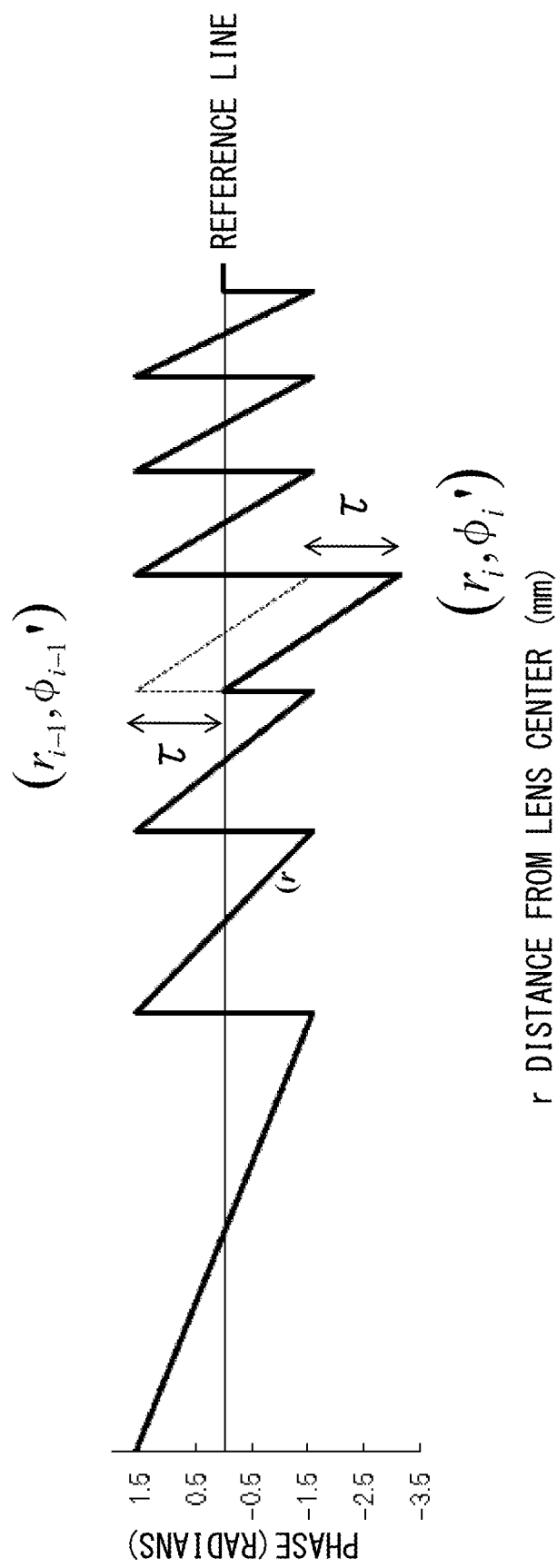
FIG. 3 is a drawing for explaining a mode of the blaze given by the phase shift τ.

Following, the present invention will be more specifically clarified by describing embodiments for carrying out the invention. First, methods and conditions, etc., for calculation simulation used by the following examples are explained.

Simulation of the Intensity Distribution on the Optical Axis

With simulation of the intensity distribution on the optical axis, for the calculation software, an item was used that can calculate amplitude distribution and intensity distribution from each zone based on a diffraction integral equation derived from a theory known in the field called the scalar diffraction theory. Using this calculation software, we calculated the intensity distribution on the optical axis. A far point light source was set up as light source for calculation, and the calculation was performed on the assumption that parallel light beams in the same phase enter into the lens. Also, in the calculation, it was assumed that the media on the object and image sides are vacuum and the lens is an ideal lens having no aberration (light beams passing through the lens form an image at the same focal point regardless of the emitting position of the light). Further, the calculation was performed based on the assumption that the wavelength equals 546 nm and the refractive power of the lens for the 0th order diffracted light (basic refractive power) equals 7 D.

Also, in the examples below, unless otherwise specified, calculation was performed with the blaze as a linear function, and expressed by the function determined by Equation 14 below.

$$\phi(r) = \frac{\phi'_i - \phi'_{i-1}}{r_i - r_{i-1}} \times r + \frac{\phi'_{i-1} \times r_i - \phi'_i \times r_{i-1}}{r_i - r_{i-1}} \quad \text{Equation 14}$$

r: Radial distance from the lens center
$r_{i-1}$: Inner diameter of the ith zone (radius)
$r_i$: Outer diameter of the ith zone (radius)
$\phi_{i-1}'$: Phase at the inner diameter position of the ith zone (radius)
$\phi_i'$: Phase at the outer diameter position of the ith zone (radius)

The intensity distribution on the optical axis was such that the distance on the optical axis from the lens position as the base point to the image plane was converted to diopters, the focal point position of the 0th order diffracted light was standardized as 0 D, and the intensity was plotted on that standardized scale. The lens aperture range for which the calculation simulation was performed, unless otherwise specified, was the region up to the zone number described in each example.

Simulation of Point Spread Function (Image, etc.) In the simulation of the point spread function, the diffraction profile of the present invention was provided as a relief structure on the front surface of each lens noted hereafter, the lens was inserted into the eye of a person, or a worn state was constructed by simulation, and the point spread function was calculated to check the image formed on the retina in that eye optical system. Simulation was performed using VirtualLab (product name) made by LightTrans GmbH, under the respective conditions noted hereafter in regards to intraocular lenses and contact lenses.

Simulation as an Intraocular Lens

The eye optical system was arranged in sequence of the cornea, aqueous humor, iris, intraocular lens, vitreous body, and retina, and the refractive index and shape were determined based on human eye data. Also, the refractive power of the intraocular lens and the pupil diameter were determined as noted below.

Intraocular lens 0th order diffracted light refractive power (diopter): 20 D

Pupil diameter: Diameter 3 mm (examples other than Example 8) or 3.15 mm (Example 8)

Simulation as a Contact Lens

The eye optical system was arranged in sequence of the contact lens, cornea, aqueous humor, iris, crystalline lens, vitreous body, and retina, and the refractive index and shape were determined based on human eye data. Also, the refractive power of the contact lens and the pupil diameter were determined as noted below.

Contact lens 0th order diffracted light refractive power (diopter): 0 D

Pupil diameter: Diameter 3.8 mm

Also, the same as with simulation of intensity distribution on the optical axis, the simulation relating to point spread function noted above was also performed with incident light wavelength of 546 nm, and the light source being a point light source at an infinite distance.

During explaining specific examples of the present invention obtained based on the method and conditions of the calculation simulation as described above based on examples, first, an outline is given of the structure and characteristics of the diffractive lens based on the present invention. As is clear from the description in the Means for Solving the Problem section described above, the diffractive structure of the diffractive multi-focal ophthalmic lens of the present invention has as its basis the structure represented by the phase function for which the inclination of a blaze of a specific zone of the subject standard profile is reversed. What is called the standard profile here is interpreted as a profile having pitches comprising concentric circle zones, with the phase function of the zone being a blaze shaped function, for which it is possible to generate at least two focal points using the diffractive structure comprising this profile.

Figure 5A:
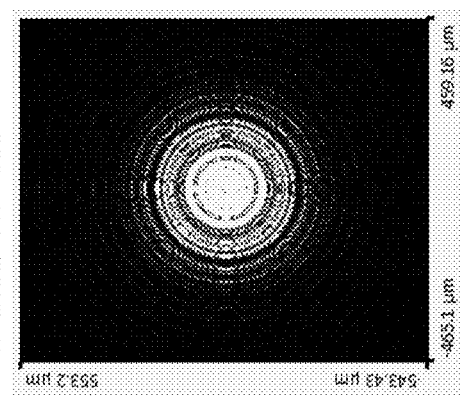
FIGS. 5A-5D are drawings for explaining the structure and characteristics of the standard profile that is the base of the diffractive multi-focal ophthalmic lens according to the present invention, where

In Table 1 and FIG. 5A, an example is shown of the standard profile which is the base of the diffractive structure of the present invention. As shown in Table 1, in the standard profile, the zone radii determined by the zone sequence (1) and the zone radii determined by the zone sequence (2) are arranged in increasing order of radius from the center toward the outer periphery within the same region, making standard profile constituent zones. Said another way, this standard profile has a concentric zone structure for which the zone sequence (1) and the zone sequence (2) are overlapped on each other. Also, the zones set using the respective zone radii are new constituent zones of the standard profile.

TABLE 1

(Basic standard profile and present invention profile for explaining the present invention)

| A | B Zone sequence (1) Addition power P = 4D | C Zone sequence (2) Addition power P = 3D | E | F | G | H | I | J |
|---|---|---|---|---|---|---|---|---|
| | | | | Standard profile | | | Present invention profile | |
| Zone No. n | Zone radius(mm) $r_n$ | Zone radius(mm) $r_n$ | Zone No. i | Zone radius(mm) $r_i$ | Phase constant h | Phase shift τ (radians) | Phase constant h | Phase shift τ (radians) |
| 1 | 0.5225 | 0.4266 | 1 | 0.4266 | 0.5 | 0 | 0.5 | 0 |
| 2 | 0.7389 | 0.7389 | 2 | 0.5225 | 0.5 | 0 | −0.5 | 0 |
| 3 | 0.9050 | 0.9539 | 3 | 0.7389 | 0.5 | 0 | 0.5 | 0 |
| 4 | 1.0450 | 1.1287 | 4 | 0.9050 | 0.5 | 0 | 0.5 | 0 |
| 5 | 1.1683 | 1.2798 | 5 | 0.9539 | 0.5 | 0 | −0.5 | 0 |
| 6 | 1.2798 | 1.4149 | 6 | 1.0450 | 0.5 | 0 | 0.5 | 0 |
| 7 | 1.3824 | | 7 | 1.1287 | 0.5 | 0 | 0.5 | 0 |
| 8 | 1.4778 | | 8 | 1.1683 | 0.5 | 0 | −0.5 | 0 |
| 9 | | | 9 | 1.2798 | 0.5 | 0 | 0.5 | 0 |
| 10 | | | 10 | 1.3824 | 0.5 | 0 | 0.5 | 0 |
| 11 | | | 11 | 1.4149 | 0.5 | 0 | −0.5 | 0 |
| 12 | | | 12 | 1.4778 | 0.5 | 0 | 0.5 | 0 |

In specific terms, the zone sequence (1) has the zone radius determined by Equation 15 below with $r_1$=0.5225 mm, P=4 diopters (hereafter, diopters is abbreviated as "D"), and design wavelength λ=546 nm. Similarly the zone sequence (2) has the zone radius determined by Equation 15 below with $r_1$=0.4266 mm, P=3 D, and design wavelength λ=546 nm. The zones determined by the zone radii of the zone sequences (1) and (2) are constituent zones of the standard profile of this example. The zone number of the standard profile is determined using symbol i (i is a natural number). A blaze shaped phase function is set for each zone of the standard profile, and here, shown is an example for which the phase constant is set to h=0.5, and the phase shift to τ=0 for each blaze. When designing the zone using Equation 15 below, unless otherwise specified, the design wavelength is λ=546 nm. This standard profile has the shape shown in FIG. 5A.

$$r_n = \sqrt{r_1^2 + \frac{2(n-1)\lambda}{P}}$$ Equation 15

$r_n$: The nth zone radius of a certain zone sequence
$r_1$: The first zone radius of the zone sequence
n: Natural number
P: Addition power based on 1st order diffracted light of the zone sequence
λ: Design wavelength FIG. 5B shows the intensity distribution on the optical axis of this standard profile. With this standard profile, at the 0 D position, the peak is generated based on 0th order diffracted light, and at the 4 D position, the peak derived from +1st order diffracted light of the zone sequence (1), and at the 3 D position, the peak derived from +1st order diffracted light of the zone sequence (2) are respectively generated. When this lens is applied as an intraocular lens, for example, the 0 D peak acts as a focal point for far vision, the 4 D peak can be used as a focal point for near vision for which objects of approximately 35 to 40 cm in front can be seen, and also, the 3 D peak can be used as a focal point for intermediate vision for which objects of approximately 50 cm in front can be seen, and this is useful as a multi-focal intraocular lens for which vision is possible of course for far vision, and also for purposes from reading to viewing a personal computer screen. In other words, this standard profile gives a profile as a diffractive lens that can generate three focal points: the 0 D position focal point based on 0th order diffracted light, the 4 D position focal point derived from the zone sequence (1), and the 3 D position focal point derived from the zone sequence (2).

However, with the diffractive lens comprising this standard profile (standard diffractive multi-focal lens), as shown in FIG. 5B, a small peak group is also generated other than at the target focal point position (indicated by the arrow in the drawing). These small peaks are based on high order diffracted light and normally are called multi-order light. When there is a high occurrence of multi-order light, it is difficult to focus the incident light on the main focal point positions that are the target, which leads to a decrease in the gain of the main peak group. Also, multi-order light can also be a cause of halo generation. Halo is an expansion of light in a ring or circle shape that occurs around a light source when viewing a far point light source at night (e.g. a far street light or car headlight) when wearing a diffractive lens as an intraocular lens or contact lens, etc. When halo occurs, there is the risk of losing visibility of other objects due to that expansion of light.

Figure 5C:
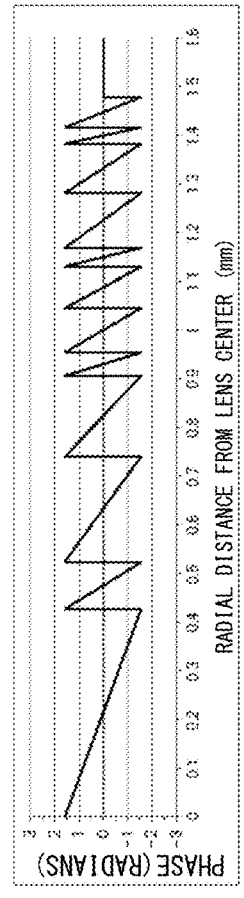
Figure 5B:
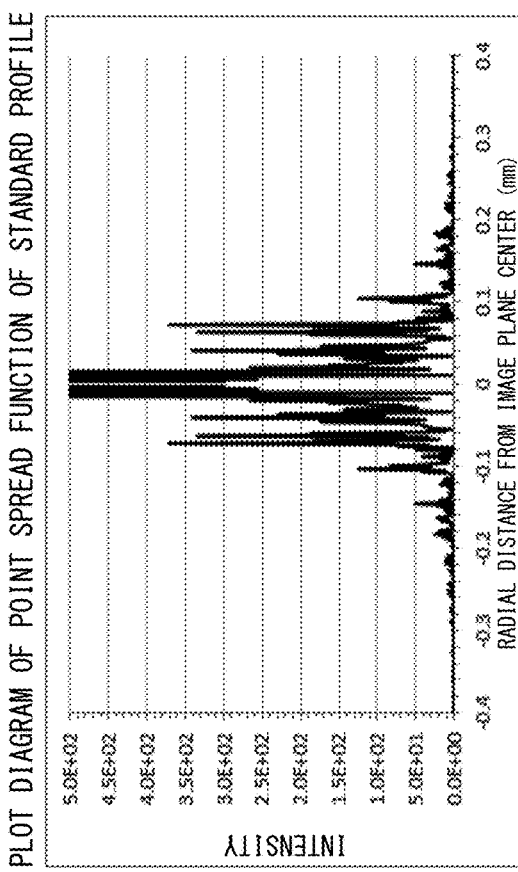
Figure 5D:
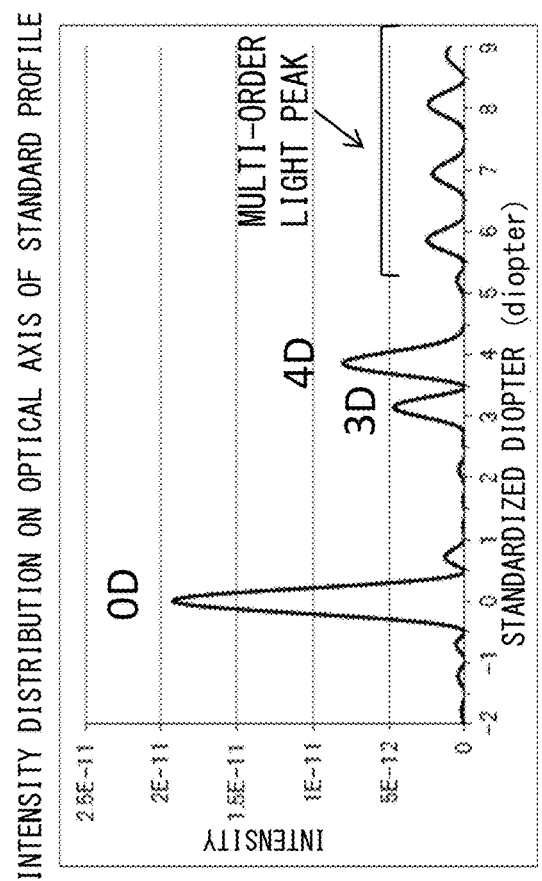

FIGS. 5C and 5D show the simulation results when viewing a far point object in a state with an item, for which the standard profile of FIG. 5A is given to the front surface of the intraocular lens as a relief form diffractive structure, inserted in the eye, and shows the point spread function calculated when assuming a state with the far focal point formed on the retina. As shown in FIG. 5C, when this standard profile is made to be a diffractive lens, we can see that the ring or circle shaped light expansion occurs around the point light source. Typically, the cause of halo is understood to be due to the multi-order light that stray and mix into the focal point image plane for far vision. The plot diagram of the point spread function shown in FIG. 5D shows the state of the stray light mixing in as noise-like peaks around the center peak. The intensity of this peak group is extremely low compared to the intensity of the main peak. However, in a dark background environment of night, even weak intensity light is likely to stand out, and furthermore, with the high sensitivity of the human eye, the light is sensed by the retina, and thus recognized as halo. In this way, multi-order light becomes a source of noise generation that causes halo. Therefore, suppressing the occurrence of multi-order light, and suppressing the occurrence of halo, are important tasks for multifocal lenses.

The present invention proposes a diffractive structure that can address the problem of the standard profile. The profile that forms the diffractive structure of the present invention is hereafter called "present invention profile." Following is an explanation of the basic structure of the present invention profile.

Following is shown an example in which the inclination of the blaze is reversed for the second, fifth, eighth, and eleventh zones of the standard profile, and the valley and peak positions of neighboring zones are linked so as not to form one valley that exists between the valley and peak. FIG. 6A shows the newly formed profile by reversing the inclination of the blaze of the zone in contrast to the standard profile (FIG. 5A). Details of the present invention profile are shown in Table 1. Reversing the inclination of the blaze means that the sign of the phase constant is reversed, and here, a negative phase constant is set. A specific zone in the standard profile serves as the adjustment zone set with the inclination of the blaze reversed.

The intensity distribution in the optical axis direction of the profile is displayed together with that of the standard profile in FIG. 6B. In FIG. 6B, the solid line shows the present invention profile, and the dashed line shows the standard profile. In examples hereafter in which the standard profile and the present invention profile are shown in the same drawing, items of the present invention profile are shown using a solid line, and items of the standard profile are shown using a dashed line. With this example, when compared with the standard profile, we can understand that while "maintaining the peak intensity of the 0 D position," "the peak of the multi-order light is reduced," and "the 3 D and 4 D peak intensity increase." In other words, the inventor newly discovered that, "by reversing the inclination of the blaze of a prescribed zone of the standard profile, light that was lost as multi-order light with the standard profile has improved gain by being effectively distributed to the target peak." Furthermore, as shown in FIG. 6C, it was also newly discovered that with the point spread function in the image plane of the 0th order focal point position in the present invention profile, the ring in the outer periphery area becomes hardly noticeable, namely, halo is reduced. The point spread function with each example described hereafter, unless otherwise specified, shows the point spread function in the image plane of the 0 D position.

The improvement effect on the optical characteristics by reversing the blaze inclination of the phase function of a specific zone (adjustment zone) is clear from the many experiment results performed by the inventor including each of the examples described later. For example, it can also be understood from the phenomenon due to the difference in zones to be reversed can also be found from Examples 1 to 10 shown hereafter, for example.

Example 1

Example 1 based on the present invention is shown hereafter. The present invention profile of Example 1 has the profile shown in the previously described Table 1 and FIG. 7A. Meanwhile, Comparative Example 1 has a phase constant of h=0.6 for each zone in the standard profile shown in Table 1 and FIG. 5A, and the standard profile as the Comparative Example 1 is shown in Table 2 and FIG. 7A by a dashed line.

TABLE 2

(Example 1 and Comparative Example 1)

| A | B Zone sequence (1) Addition power P = 4D | C Zone sequence (2) Addition power P = 3D | E | F Standard profile (Comparative Example 1) | G | H | I Present invention profile (Example 1) | J | K Zone pitch (standardized) | L Zone area (standardized) | M Half-value width (calculated) | N Half-value width (standardized) |
|---|---|---|---|---|---|---|---|---|---|---|---|---|
| Zone No. n | Zone radius(mm) $r_n$ | Zone radius(mm) $r_n$ | Zone No. i | Zone radius(mm) $r_i$ | Phase constant h | Phase shift τ (radians) | Phase constant h | Phase shift τ (radians) | $\angle r / \angle r_{max}$ | $S/S_{max}$ | $\angle D$ (diopter) | $\angle D / \angle D_{min}$ |
| 1 | 0.5225 | 0.4266 | 1 | 0.4266 | 0.6 | 0 | 0.5 | 0 | 1 | 0.67 | 5.33 | 1.51 |
| 2 | 0.7389 | 0.7389 | 2 | 0.5225 | 0.6 | 0 | −0.5 | 0 | 0.22 | 0.33 | 10.65 | 3.01 |
| 3 | 0.9050 | 0.9539 | 3 | 0.7389 | 0.6 | 0 | 0.5 | 0 | 0.51 | 1 | 3.54 | 1.00 |
| 4 | 1.0450 | 1.1287 | 4 | 0.9050 | 0.6 | 0 | 0.5 | 0 | 0.39 | 1 | 3.54 | 1.00 |
| 5 | 1.1683 | 1.2798 | 5 | 0.9539 | 0.6 | 0 | −0.5 | 0 | 0.11 | 0.33 | 10.64 | 3.01 |
| 6 | 1.2798 | 1.4149 | 6 | 1.0450 | 0.6 | 0 | 0.5 | 0 | 0.21 | 0.67 | 5.32 | 1.50 |
| 7 | 1.3824 | | 7 | 1.1287 | 0.6 | 0 | 0.5 | 0 | 0.20 | 0.67 | 5.32 | 1.50 |
| 8 | 1.4778 | | 8 | 1.1683 | 0.6 | 0 | −0.5 | 0 | 0.09 | 0.33 | 10.64 | 3.01 |
| 9 | | | 9 | 1.2798 | 0.6 | 0 | 0.5 | 0 | 0.26 | 1 | 3.54 | 1.00 |
| 10 | | | 10 | 1.3824 | 0.6 | 0 | 0.5 | 0 | 0.24 | 1 | 3.54 | 1.00 |
| 11 | | | 11 | 1.4149 | 0.6 | 0 | −0.5 | 0 | 0.08 | 0.33 | 10.64 | 3.01 |
| 12 | | | 12 | 1.4778 | 0.6 | 0 | 0.5 | 0 | 0.15 | 0.67 | 5.32 | 1.50 |

Note:
In each table hereafter, $\angle r, \angle r_{max}, \angle D$, and $\angle D_{min}$ are the same as $\Delta r, \Delta r_{max}, \Delta D$, and $\Delta D_{min}$ in the specification light intensity realized in the outer periphery region of the focal point image plane based on the Fourier transform described later. Also, as a result of detailed investigation through performing many experiments, the inventor found that it is possible to ensure or additively increase the light intensity peak at the target focal point position while suppressing the peak of multi-order light in the intensity distribution on the optical axis by reversing the blaze inclination. Accordingly, the inventor was able to identify preferable zones for suppressing halo by decreasing light intensity of the outer peripheral side in the image plane of the focal point, with advantageous modes for the design of the diffractive multi-focal ophthalmic lens.

Specifically, in a diffractive multi-focal ophthalmic lens for which a diffraction grating comprising a blaze shaped phase function is configured by a plurality of concentric zones, for which a plurality of zone sequences with the zone radius given by Equation 15 noted above are overlapped, and a plurality of focal points are set, by setting the blaze inclination in the standard profile to be reversed, specific zones for which an effect of halo suppression, etc., is found are obtained as noted in each mode in the Means for Solving the Problem section described previously. Also, the fact that it is effective to set the blaze inclination in these specific To compare the gain change and point spread function difference at the far vision focal point positions for which halo is particularly seen as a problem, the standard profile as a comparative example hereafter has a slight variation for the phase constant and the phase shift from the original standard profile so that the peak intensity for near vision or for intermediate vision is made to be the same as those of the present invention profile.

Figure 7C:
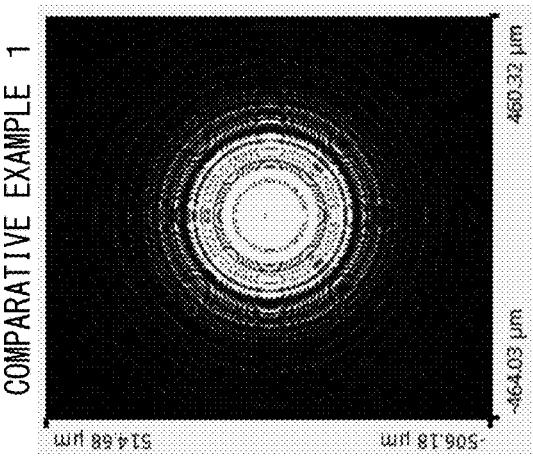
FIGS. 7A-7D are drawings for explaining the structure and characteristics of the diffractive multi-focal ophthalmic lens as Example 1 of the present invention, where
Figure 7D:
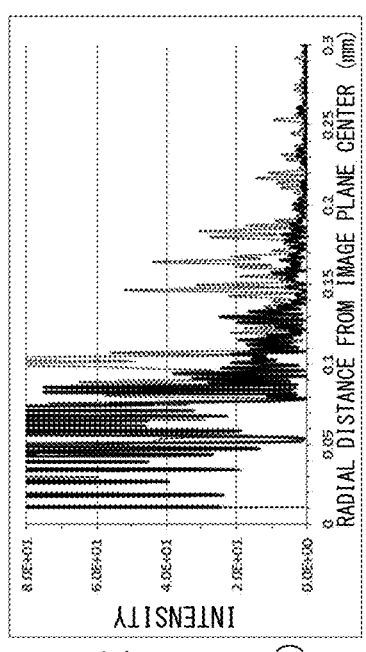
Figure 7A:
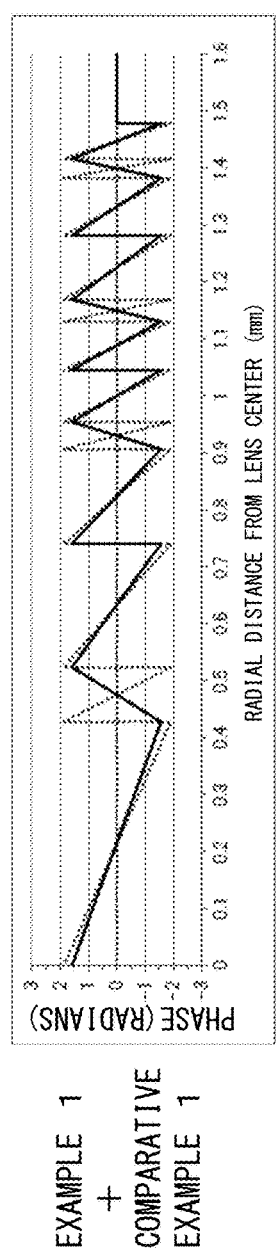
Figure 7B:
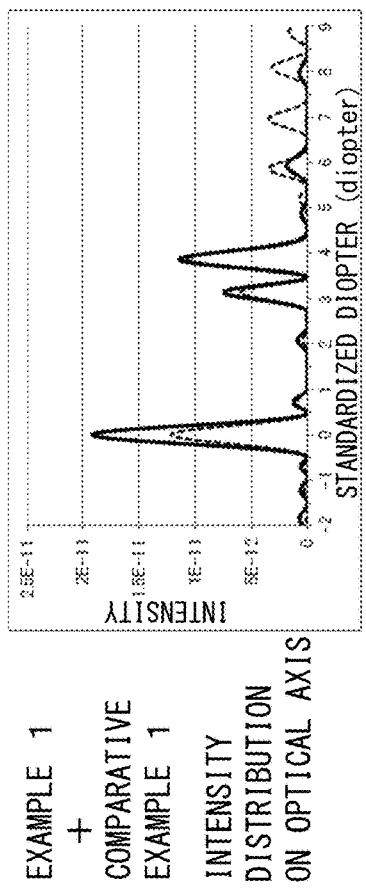

Also, Comparative Example 1 is made so that the peak intensity of the 3 D and 4 D positions between the present invention profile of Example 1 and that of Comparative Example 1 are almost the same as shown by the dashed line in FIG. 7B. Said another way, with the standard profile for which a reversed inclination is not set for each zone, loss of light occurs due to multi-order light. Therefore, in order to realize intensity of 3 D and 4 D of about the same level as the present invention profile, as with this Comparative Example 1, it is necessary to make the phase constant large, increasing the generation ratio of the +1st order diffracted light.

However, with these settings, with the profile of Comparative Example 1, there is a significant decrease in the peak intensity of 0 D. In other words, with the present invention profile of Example 1, even if the blaze step is made lower than with the profile of Comparative Example 1, simply by reversing the inclination of specific zones, it is possible to increase the 0th order diffraction intensity while maintaining the peak intensity of 3 D and 4 D.

Also, when comparing the point spread function of Example 1 and Comparative Example 1, the point spread function of Example 1 (FIG. 6C) has reduced halo expansion compared to Comparative Example 1 (FIG. 7C). From the plot diagrams of both as well (FIG. 7D), we can see that the peak group of the image plane periphery is reduced considerably with the Example 1 (solid line) compared to the Comparative Example 1 (dashed line).

Therefore, from this Example 1, we can see that with the present invention profile, while generating three focal points realized with the standard profile, generation of multi-order light is suppressed, so that the gain of the peak for far vision increases by that amount, and halo is reduced. Thus, when the diffractive structure comprising the present invention profile is used as an ophthalmic lens, such as an intraocular lens, for example, it is possible to have a multi-focal intraocular lens with good near vision, intermediate vision, and far vision, and for which halo at night is also reduced.

Example 2

Figure 8A:
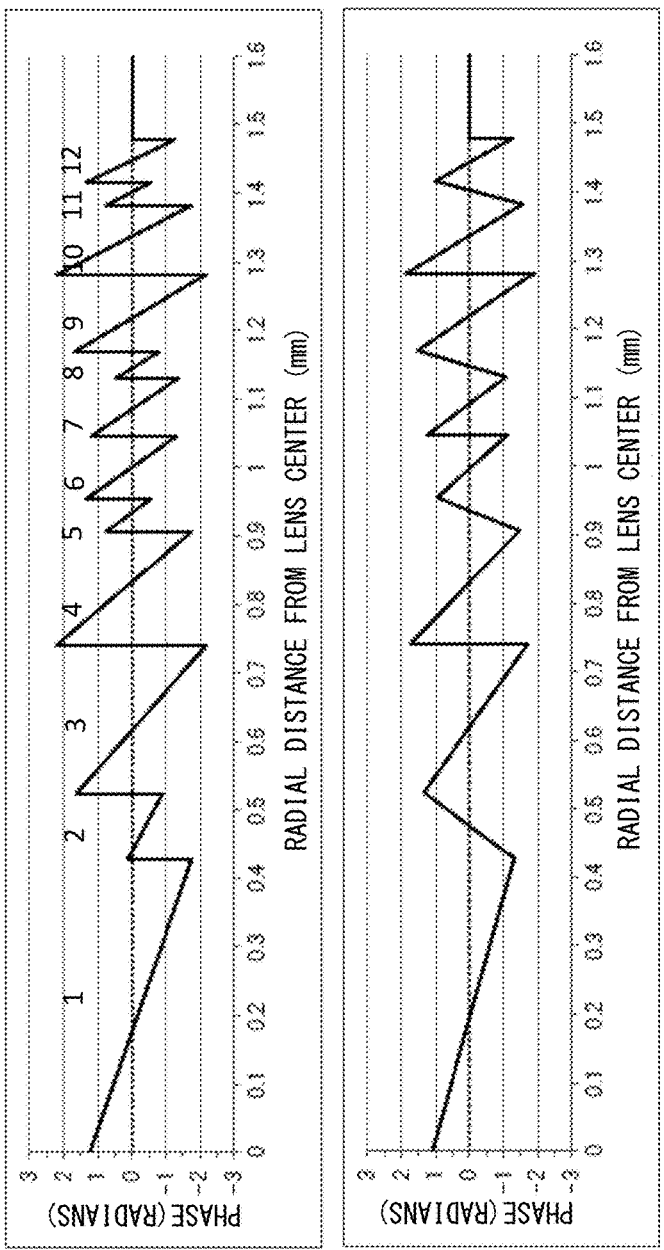
FIGS. 8A and 8B are drawings for explaining the structure and characteristics of the diffractive multi-focal ophthalmic lens as Example 2 of the present invention, where

Example 2 shows another mode related to Example 1. The radius of the constituent zones of the standard profile for Comparative Example 2 is the same as that of Comparative Example 1, but as shown in Table 3 and FIG. 8A, the phase constant and the phase shift of the blaze are set anew. The intensity distribution on the optical axis of the standard profile for Comparative Example 2 is shown by the dashed line in FIG. 8B. The standard profile of Comparative Example 2 generates peaks at the 0 D, 3 D, and 4 D positions, the same as with Comparative Example 1. With Comparative Example 2, the standard profile itself has a little generation of multi-order light, and the 0 D peak intensity for far vision is increased in comparison with Comparative Example 1. The standard profile of Comparative Example 2 can also be a multi-focal ophthalmic lens for which far vision, near vision, and intermediate vision are possible. However, with this Comparative Example 2 as well, multi-order light is generated to not an inconsiderable degree, and as shown in FIG. 9A, the same as with Comparative Example 1, a point spread function is given for which the halo expansion stands out.

TABLE 3

(Example 2 and Comparative Example 2)

| Zone No. i | Standard profile (Comparative Example 2) | | Present invention profile (Example 2) | |
|---|---|---|---|---|
| | Zone radius(mm) $r_i$ | Phase constant h | Phase shift τ (radians) | Phase constant h | Phase shift τ (radians) |
| 1 | 0.4266 | 0.4766 | −0.2406 | 0.3858 | −0.1124 |
| 2 | 0.5225 | 0.1655 | −0.3729 | −0.4244 | 0.0089 |
| 3 | 0.7389 | 0.6079 | −0.2893 | 0.4886 | −0.1929 |
| 4 | 0.9050 | 0.6317 | 0.2146 | 0.5045 | 0.1430 |
| 5 | 0.9539 | 0.2082 | 0.0893 | −0.3821 | −0.2414 |
| 6 | 1.0450 | 0.4164 | 0.0121 | 0.3318 | −0.0835 |
| 7 | 1.1287 | 0.4152 | −0.0874 | 0.3673 | 0.0763 |
| 8 | 1.1683 | 0.2071 | −0.1576 | −0.4191 | 0.2389 |
| 9 | 1.2798 | 0.6214 | −0.2471 | 0.5476 | −0.1647 |
| 10 | 1.3824 | 0.6277 | 0.2270 | 0.5518 | 0.1513 |
| 11 | 1.4149 | 0.2086 | 0.1128 | −0.4155 | −0.2770 |
| 12 | 1.4778 | 0.4168 | 0.0331 | 0.3658 | −0.1207 |

Example 2, based on the standard profile for Comparative Example 2, is set so that the valley (valley bottom point) and peak positions are slightly decreased in depth and height by the phase constant and phase shift of the entire blaze being varied, and then the valleys and peaks of neighboring zones are connected, with the inclination of the blaze of the second, fifth, eighth, and eleventh zones reversed. Details of the present invention profile for Example 2 are as shown in Table 3 and FIG. 8A noted above. The present invention profile comprises the same zone pitches as those of Example 1, but the blaze for which the inclination is reversed has a shape for which the peaks and valleys are linked at the positions different from those of Example 1. The phase constant of the adjustment zone for which the blaze inclination is reversed is a negative value.

Figure 8B:
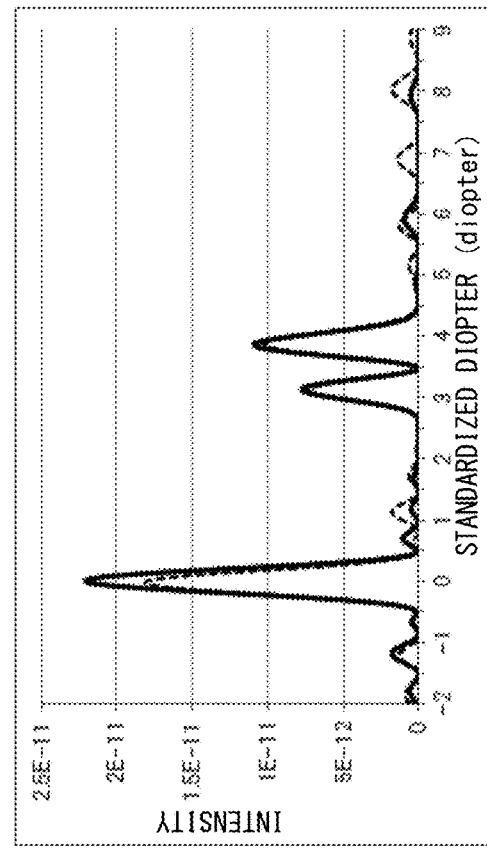

The intensity distribution on the optical axis of the present invention profile is shown by a solid line in FIG. 8B. The multi-order light is further reduced compared to the standard profile of Comparative Example 2, and we can see that this decreased amount is allocated to the increased amount of the 0 D peak for far vision. FIG. 9B shows the point spread function of Example 2. FIG. 9C shows the plot diagram (only the plus coordinate axis is displayed) together with the Comparative Example 2. We can see that compared to Comparative Example 2, Example 2 has lower noise at the image plane periphery, and halo is clearly reduced. As can be understood from this example, it is possible to reduce the multi-order light to some degree even with the standard profile itself by doing blaze adjustment. However, we can see that by reversing the sign of the inclination of a specific blaze with respect to the standard profile, the multi-order light is further decreased, which leads to an increase in gain of the main peak, as well as suppression of occurrence of halo.

Examples 2-2, 2-3, 2-4

Examples 1 and 2 described above are set such that the sign of the blaze inclination for a specific zone is reversed so as to connect the valley and peak of neighboring zones. Meanwhile, with the present invention, the connecting positions of the valley part and peak part of the zone for which the sign of the blaze inclination is reversed do not have to match completely those of the valley part and the peak part of neighboring zones. Thus, it is also possible to adopt a mode for which only the valley part and the valley part match, and the peak part and the peak part do not match. Alternatively, it is also possible to have only the peak part and the peak part match, and not to have the valley part and the valley part match. Furthermore, it is also possible to adopt a mode for which neither the valley part side nor the peak part side matches. Specific examples of this kind of partial matching are shown by example in Examples 2-2, 2-3, and 2-4 below.

The Example 2-2 shown in FIGS. 10A-10D is a mode for which the valley part and the peak part, of the second, fifth, eighth, and eleventh zones for which the sign of the blaze inclination are reversed in Example 2 described previously, do not match either the valley part or peak part of the neighboring zones, and these are connected midway in a perpendicular line dropped to the reference line from the valley part and peak part of neighboring zones. Also, Example 2-3 shown in FIGS. 11A-11D shows an example of a reversed-inclination blaze for which a match is seen for the valley part of the subject zone, but the blaze is not connected at the peak part, and Example 2-4 shown in FIGS. 12A-12D shows an example of a reversed-inclination blaze for which there is a connection at the peak part of the subject zone, but a match is not seen for the valley part.

Figure 10A:
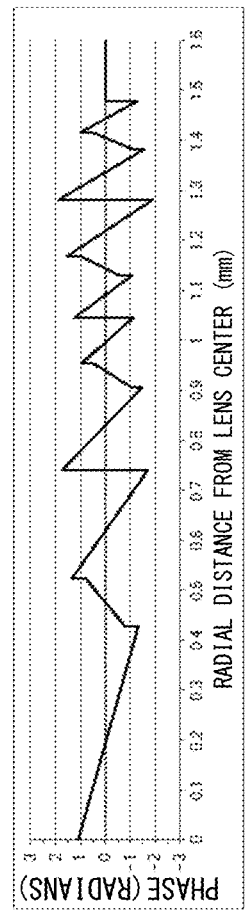
FIGS. 10A-10D are drawings for explaining the structure and characteristics of the diffractive multi-focal ophthalmic lens as Example 2-2 of the present invention, where
Figure 10C:
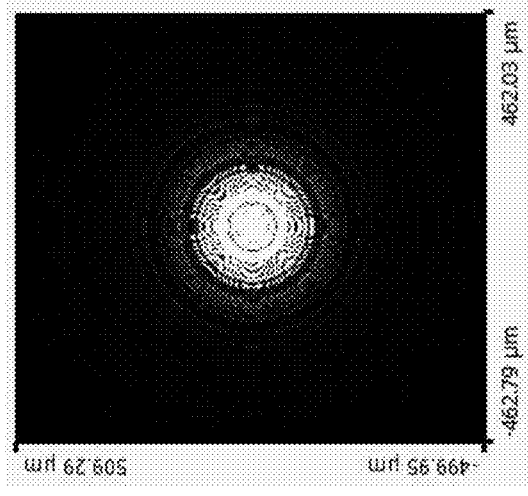
Figure 10D:
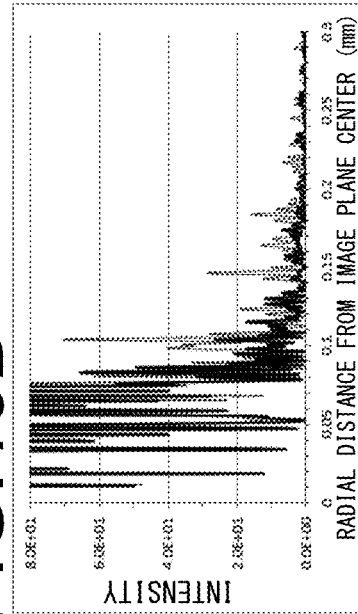
Figure 10B:
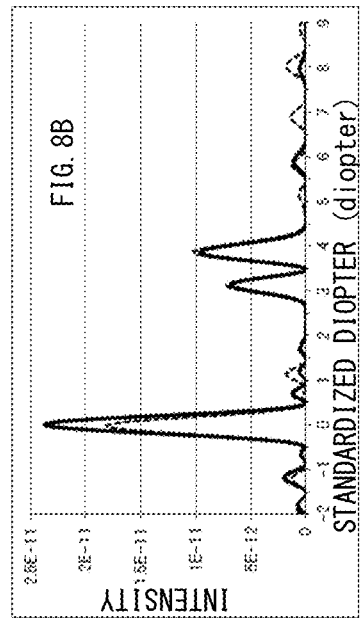
Figure 11A:
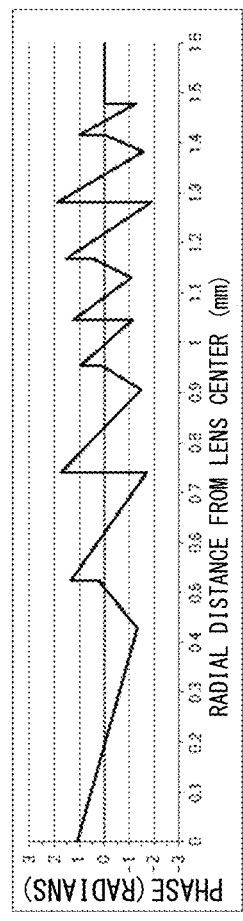
FIGS. 11A-11D are drawings for explaining the structure and characteristics of the diffractive multi-focal ophthalmic lens as Example 2-3 of the present invention, where
Figure 11C:
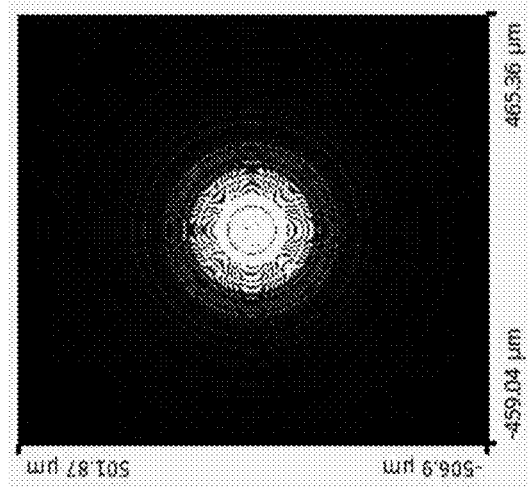
Figure 11D:
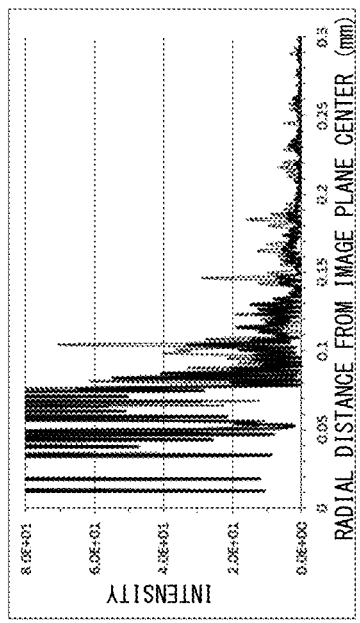
Figure 11B:
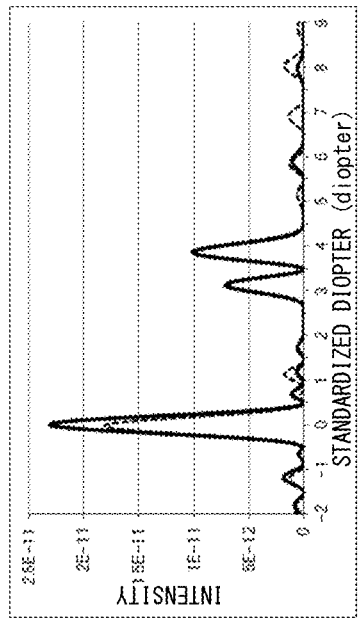
Figure 12A:
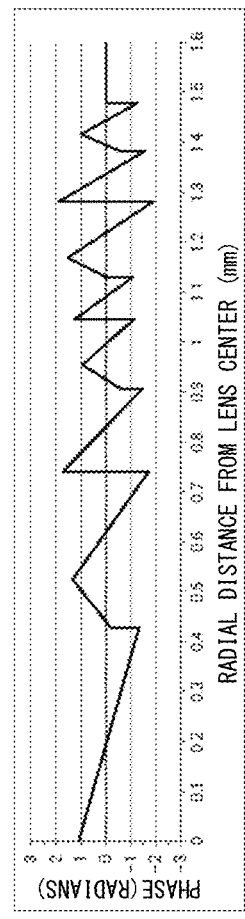
FIGS. 12A-12D are drawings for explaining the structure and characteristics of the diffractive multi-focal ophthalmic lens as Example 2-4 of the present invention, where
Figure 12C:
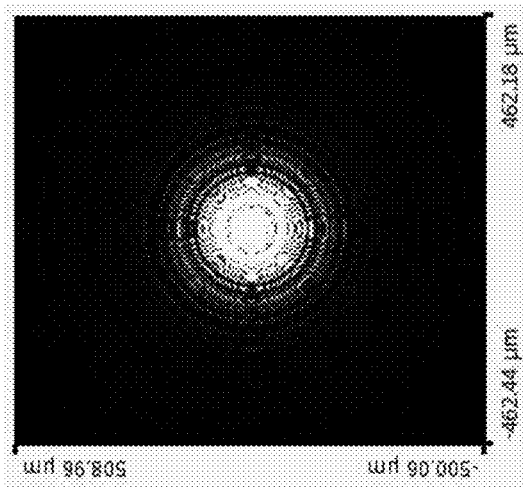
Figure 12D:
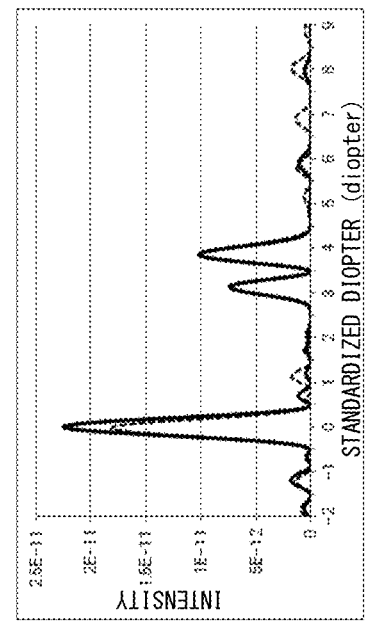
Figure 12B:
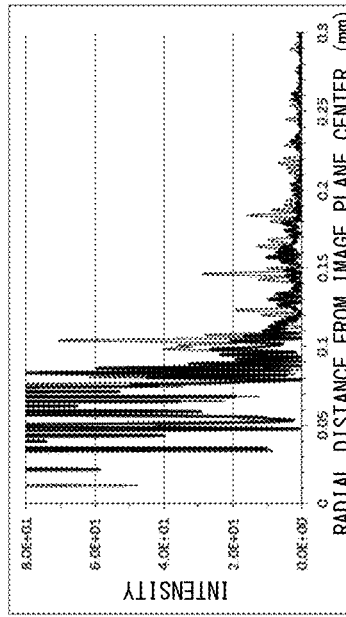

Details of the present invention profile of Examples 2-2, 2-3, and 2-4 are as shown in Table 4, Table 5, Table 6 below, and FIG. 10A, FIG. 11A, and FIG. 12A. With this group of Examples, there is no difference from Example 2 in terms of the zone radius of the configuration, and absolutely no difference in the phase constant and phase shift of the blaze of the zone other than the adjustment zone for which the inclination is reversed. These are items for which there is only a slight difference in the phase constant and phase shift of the blaze with reversed inclination, and a difference in the connecting position. The intensity distributions in the optical axis direction of the profile of this example group are shown in FIG. 10B, FIG. 11B, FIG. 12B, and the point spread functions are shown in FIG. 10C, FIG. 11C, and FIG. 12C respectively.

TABLE 4

(Example 2-2)

Present invention profile (Example 2-2)

| Zone No. i | Zone radius(mm) $r_i$ | Phase constant h | Phase shift τ (radians) |
|---|---|---|---|
| 1 | 0.4266 | 0.3858 | −0.1124 |
| 2 | 0.5225 | −0.25 | 0.0089 |
| 3 | 0.7389 | 0.4886 | −0.1929 |
| 4 | 0.9050 | 0.5045 | 0.1430 |
| 5 | 0.9539 | −0.25 | −0.2414 |
| 6 | 1.0450 | 0.3318 | −0.0835 |
| 7 | 1.1287 | 0.3673 | 0.0763 |
| 8 | 1.1683 | −0.25 | 0.2389 |
| 9 | 1.2798 | 0.5476 | −0.1647 |
| 10 | 1.3824 | 0.5518 | 0.1513 |
| 11 | 1.4149 | −0.25 | −0.2770 |
| 12 | 1.4778 | 0.3658 | −0.1207 |

TABLE 5

(Example 2-3)

Present invention profile (Example 2-3)

| Zone No. i | Zone radius(mm) $r_i$ | Phase constant h | Phase shift τ (radians) |
|---|---|---|---|
| 1 | 0.4266 | 0.3858 | −0.1124 |
| 2 | 0.5225 | −0.25 | −0.5389 |
| 3 | 0.7389 | 0.4886 | −0.1929 |
| 4 | 0.9050 | 0.5045 | 0.1430 |
| 5 | 0.9539 | −0.25 | −0.6564 |
| 6 | 1.0450 | 0.3318 | −0.0835 |
| 7 | 1.1287 | 0.3673 | 0.0763 |
| 8 | 1.1683 | −0.25 | −0.2923 |
| 9 | 1.2798 | 0.5476 | −0.1647 |
| 10 | 1.3824 | 0.5518 | 0.1513 |
| 11 | 1.4149 | −0.25 | −0.7969 |
| 12 | 1.4778 | 0.3658 | −0.1207 |

TABLE 6

(Example 2-4)

Present invention profile (Example 2-4)

| Zone No. i | Zone radius(mm) $r_i$ | Phase constant h | Phase shift τ (radians) |
|---|---|---|---|
| 1 | 0.4266 | 0.3858 | −0.1124 |
| 2 | 0.5225 | −0.25 | 0.5567 |
| 3 | 0.7389 | 0.4886 | −0.1929 |
| 4 | 0.9050 | 0.5045 | 0.1430 |
| 5 | 0.9539 | −0.25 | 0.1735 |
| 6 | 1.0450 | 0.3318 | −0.0835 |
| 7 | 1.1287 | 0.3673 | 0.0763 |
| 8 | 1.1683 | −0.25 | 0.7701 |
| 9 | 1.2798 | 0.5476 | −0.1647 |
| 10 | 1.3824 | 0.5518 | 0.1513 |
| 11 | 1.4149 | −0.25 | 0.2430 |
| 12 | 1.4778 | 0.3658 | −0.1207 |

In all of Examples 2-2, 2-3, and 2-4, the multi-order light is decreased compared to Comparative Example 2, and we can see an increase in peak intensity for far vision to improve gain, and also a decrease in halo expansion. Also, as can be understood from this group of examples, with the blaze for which the sign of the inclination is reversed in the phase function, it is sufficient as long as the inclination is reversed, and acceptable even if the structure does not have the valley part and peak part match those of the neighboring zones.

Examples 2-5, 2-6

Figure 13A:
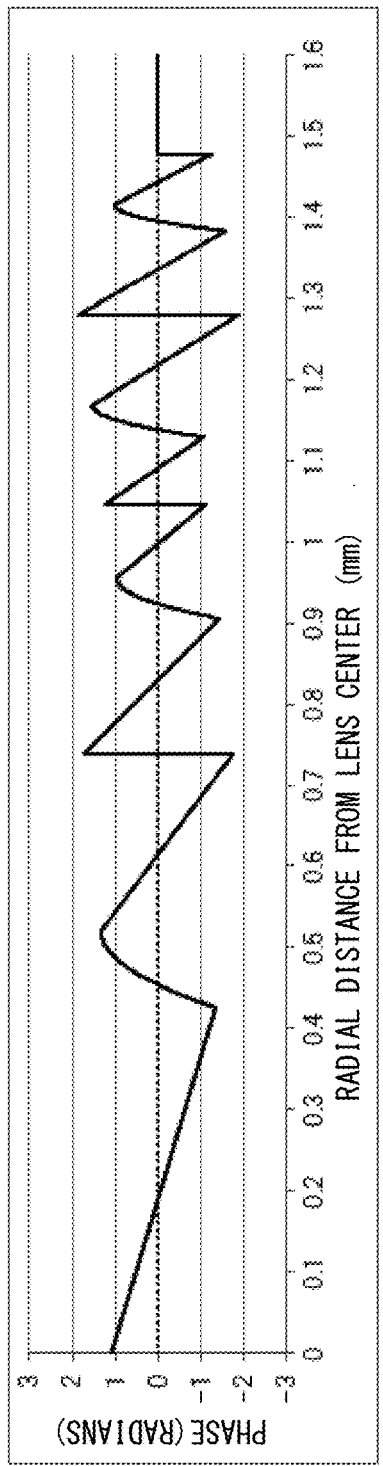
FIGS. 13A and 13B are drawings for explaining the structure and characteristics of the diffractive multi-focal ophthalmic lens as Example 2-5 of the present invention, where
Figure 13B:
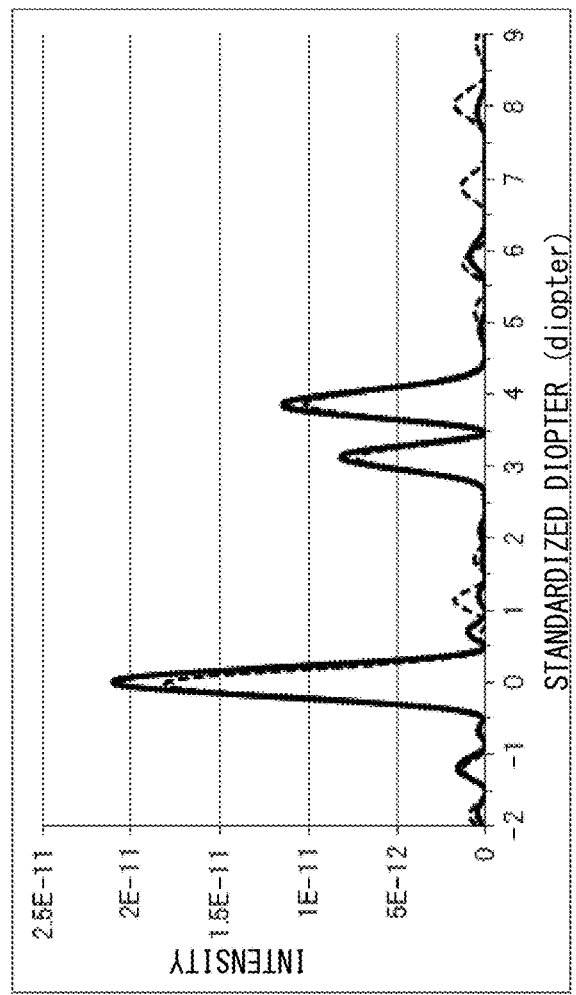
Figure 14A:
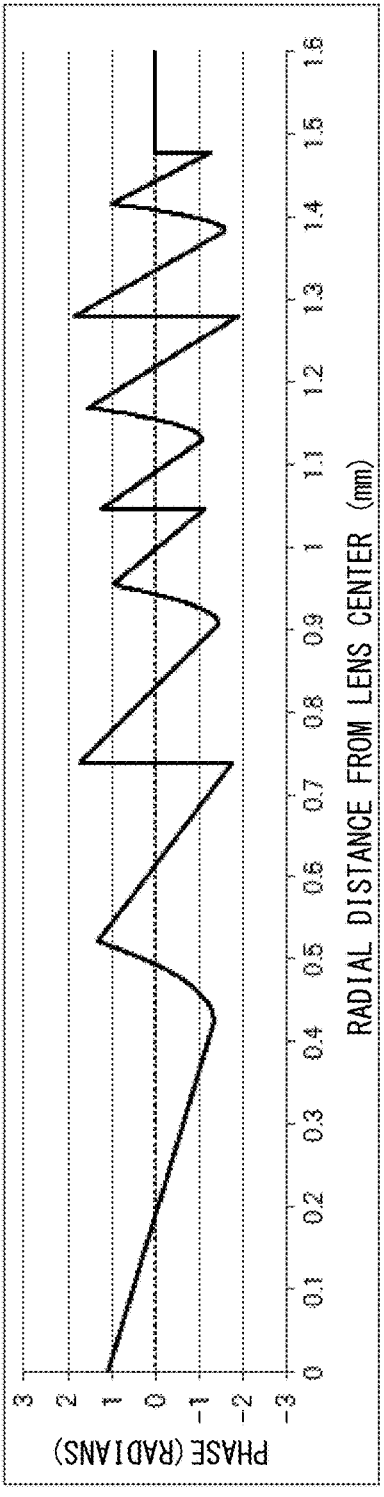
FIGS. 14A and 14B are drawings for explaining the structure and characteristics of the diffractive multi-focal ophthalmic lens as Example 2-6 of the present invention, where
Figure 14B:
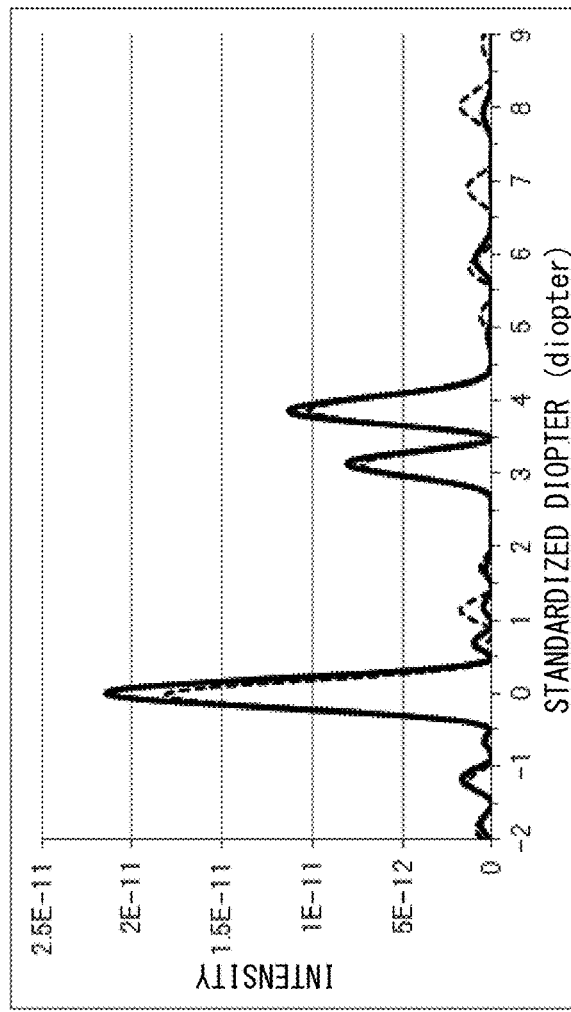

Furthermore, whereas the reversed-inclination portion of the blaze shown in the preceding examples each have a phase function that changes linearly, the blaze for which the inclination is reversed does not have to be a blaze that changes linearly between the valley part and peak part of neighboring zones. For example, with Examples 2-5 and 2-6, the blaze of a zone for which the inclination is reversed is connected by a parabolic function between the neighboring valley part and peak part. For Example 2-5, the parabola is convex upward (FIG. 13A), and for Example 2-6, the parabola is convex downward (FIG. 14A). In items connected by this function, from FIG. 13B and FIG. 14B showing the simulation results of light intensity distribution on the optical axis, we can see that there is a decrease in multi-order light and an improved gain of peak intensity for far vision.

Examples 2-7, 2-8, 2-9

Also, the blaze based on the parabolic trajectory shown by example in Examples 2-5 and 2-6 can be used for zones other than the adjustment zones for which the inclination sign is reversed. For example, as shown in FIG. 15A, Example 2-7 is an item for which the blaze of the positive phase constant is set as a parabolic trajectory that is convex downward, and the blaze of the negative phase constant is set as a parabola that is convex upward. Meanwhile, with Example 2-8, as shown in FIG. 15B, the blaze of the positive phase constant has a parabola trajectory that is convex upward, and the blaze of the negative phase constant has a parabola trajectory that is convex downward. Furthermore, with Example 2-9, as shown in FIG. 15C, each blaze is expressed as a trajectory of the Sine function.

With the present invention profile, having the sign of the blaze inclination of a specific zone (adjustment zone) be reversed is important, and the profile can be used for items with the blaze trajectory being a straight line or parabolic, as well as for items with a trajectory of a trigonometric function such as a Sine function, etc. Said another way, the standard profile that is the basis of the present invention profile is a diffraction grating having a plurality of focal points, and the specific shape of the blaze for the phase function of the standard profile is not limited. Thus, in addition to being a straight line shape, the blaze can also be formed with various curved shapes or a combined shape of a straight line and curve etc. Also, with a curved blaze for the standard profile as well, it is possible to use a straight line shape for the blaze with a reversed inclination in the present invention profile.

Study of Image Formation Characteristics in the Examples Noted Above

From the examples noted above, we can see that by using the present invention profile, the generation of multi-order light is suppressed in the diffractive multi-focal ophthalmic lens, and there is also a reduction in the peak group of the periphery of the point spread function of the focal point image plane of the 0th order diffracted light, as well as halo expansion is reduced. This kind of improvement effect of the optical characteristics can be explained as noted hereafter through the many experiments and studies, etc., done by the inventor, including the examples noted above.

In general, the image-formation characteristics of the focal point image plane of the 0th order diffracted light among the lights made incident on a lens and emitted is described by Fourier transform of the pupil function representing the lens characteristics. For the phase function configuring the pupil function as well, it is also possible to grasp the image-formation characteristics from the Fourier transform analogy. For example, an item for which a blaze shaped function is set as the phase function has a shape such as a sawtooth, for example, but generally, the Fourier transform spectrum of a sawtooth form periodic function gives distribution for which the spectrum peaks are generated over the high frequency region though the spectral intensity gradually attenuates. Here, with the image-formation optics, the spectral distribution can be interpreted as an item representing the amplitude characteristics of light in the 0th order focal point image plane. The point spread function provides a peak distribution similar to the Fourier transform spectrum for the sawtooth function in a broad region from the image plane center to the outer periphery. The peaks attenuate as they go away from the image plane center so that the intensity of peaks is reduced, but weak peaks remain at the outer periphery. Even if these peaks have a weak intensity, they can be perceived by the human eye as described previously, and are recognized as a ring or circle around the light source. In other words, they provide a halo pattern that expands.

On the other hand, an item for which the inclination of the blaze of a specific zone in the sawtooth form is reversed gives a triangular or pseudo triangular shape between neighboring zones. This shape is similar to the trigonometric function shape as the Fourier spectral component, so that the Fourier transform spectrum does not require the high frequency component, and is a structure mainly comprising a low-frequency spectrum. Specifically, this profile provides the point spread function for which the noise peaks do not expand to outer peripheral region.

Basically, any zone can be the target for which the sign of the inclination of the blaze is reversed. However, there are specific zones preferable for realizing the effects of the present invention.

First, there are zones preferable for suppressing the occurrence of noise in the image plane periphery with the point spread function. From the analogy of Fourier transform for the sawtooth function noted above, a blaze of which a zone period is short, in other words, the blaze of the region with a narrow zone pitch, can be a preferred target zone. In other words, a zone with a short period generates easily a spectrum with high frequency component. Specifically, a weak peak noise is likely to be generated up to the outer peripheral part with the point spread function. Therefore, zones for which the period is short, said another way, for which the pitch is narrow, or have a small area, can be listed first as a candidate for a preferable adjustment zone for reversing the sign of the blaze inclination.

Therefore, as one criterion for selecting the preferable zone, first, the selection criterion focusing on the zone pitch can be listed. When using the zone pitch as a selection criterion, the outcome for which the pitch of each zone is standardized with the zone that gives the maximum pitch is preferably used with the present invention. For example, when the pitch of the zone that gives the maximum pitch among the constituent zones is $\Delta r_{max}$, the outcome for which the pitch $\Delta r$ of each constituent zone is divided by $\Delta r_{max}$, namely $\Delta r/\Delta r_{max}$, can be used as the parameter for selection.

It is also possible to select other parameters. For example, it is also possible to combine with selection that focuses on zone areas. For example, when the area of the zone that gives the maximum area among the constituent zones is set as $S_{max}$, the outcome for which the area S of each constituent zone is divided by $S_{max}$, namely $S/S_{max}$, can be used as the parameter for selection.

Incidentally, with respect to $\Delta r/\Delta r_{max}$ of the zones for which the inclination of the blaze is reversed (second, fifth, eighth, and eleventh zones) in Examples 1 and 2, approximately 0.22 of the second zone is maximum and the pitches are narrow in all cases. $S/S_{max}$ of the zone is 0.33 in all cases, and the zone with the smallest zone area is selected.

Furthermore, in addition to the selection parameters specified from the analogy of the Fourier transform described above, it is also possible to use the width of the intensity distribution on the optical axis that is provided by each constituent zone of the profile as a parameter when selecting a preferable zone for which the sign of the blaze inclination is reversed.

Figure 16A:
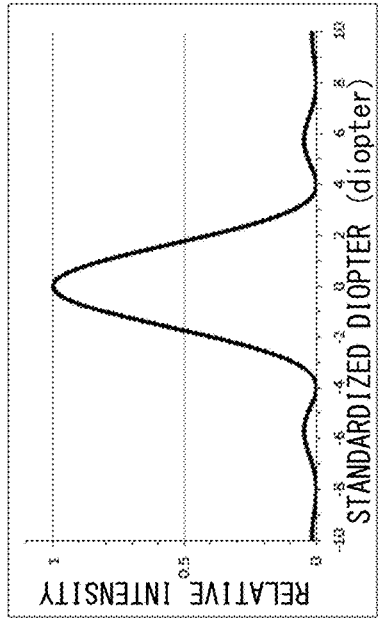
FIGS. 16A-16C are drawings for explaining the intensity distribution on the optical axis of a specific zone in Example 1 or 2 of the present invention, where
Figure 16B:
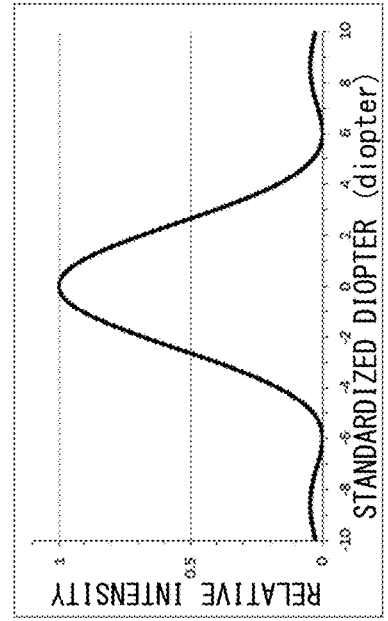
Figure 16C:
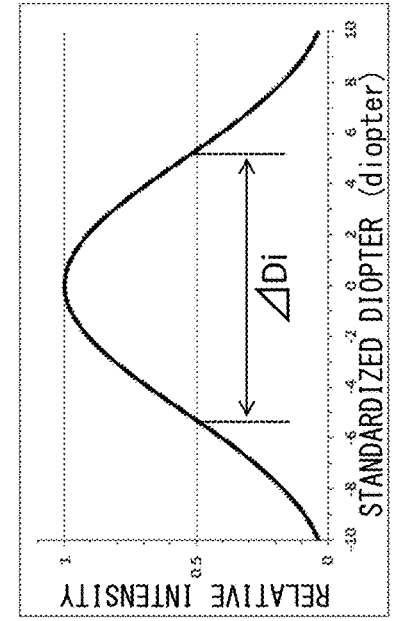

In specific terms, the intensity distribution on the optical axis of light emitted from each zone of the profiles of Example 1 or Example 2 are classified into the intensity distributions shown in FIGS. 16A, 16B, and 16C. The width of the intensity distribution in the optical axis direction of each of the third, fourth, ninth, and tenth zones is the same, being the narrowest. Next, the intensity distribution from the first, sixth, seventh, and twelfth zones is the second narrowest, and the width of the intensity distribution from the second, fifth, eight, and eleventh zones is the widest. With the present invention, it is also possible to reverse the sign of the blaze of the zone given the widest intensity distribution. This is because the light emitted from such target zone will be diffracted and reach a wide range on the optical axis, and the light energy will be distributed without waste to the main peak positions given by the standard profile. Therefore, there is no decrease in gain of the main peaks even if the sign of the blaze of that zone is reversed, and it is conceivable that the effects of the present invention can be preferably obtained.

For the width of the intensity distribution, the intensity distribution obtained by configuring the present invention profile on the ideal lens described above is used. Therefore, even if the diffractive structure of the present invention is set for a lens with an aberration or a lens that is aspherical, it is only needed to use the intensity distribution obtained by combining the diffractive structure once on the ideal lens. As a result, the width of the intensity distribution becomes a zone-specific parameter that does not depend on the base power (power given by the 0th order diffracted light) of the lens by using the optical axis in diopters unit as the coordinate axis. Therefore, it is possible to use the width of the intensity distribution displayed in diopters as the selection parameter of the present invention.

With the present invention, the half-value width (width of power for which the value of the intensity in the intensity distribution is half) is used as the width of the intensity distribution. The narrowest half-value width among the constituent zones is $\Delta D_{min}$, and the value for which the half-value width $\Delta D$ of the intensity distribution from each zone is standardized by $\Delta D_{min}$, namely $\Delta D/\Delta D_{min}$, is used as the selection criterion. Incidentally, in Example 1 or 2, $\Delta D/\Delta D_{min}$ of the second, fifth, eighth, and eleventh zones for which the inclination is reversed is approximately 3, and we can see that these zones give broad intensity distribution.

For the reasons above, it is possible to easily and effectively select a preferable zone for which the sign of the blaze inclination is reversed based on the aforementioned parameters. As a result, it is possible to obtain a diffractive multi-focal ophthalmic lens with multiple focal points that suppresses the occurrence of multi-order light so as to improve the gain of the peak intensity while reducing halo.

As other advantages of reversing the sign of the inclination of the zone blaze, in addition to the improvement in image formation and optical characteristics described above, ease of manufacturing the diffractive structure can also be cited. For example, when using the relief form diffractive structure for the standard profile of Comparative Example 2 (FIG. 8A), processing of complicatedly intricate steps is required, making it difficult to precisely and efficiently do processing of the relief.

On the other hand, with the present invention profile shown as Example 2 in the same drawing, the processing is easier to do in a profile for which the triangular shape is partially introduced as a result of connecting the valley and the peak, for example. Particularly in zones with a small area, or in zones with a narrow pitch, when reversing is determined to be preferable, the intricate structure is converted to a simple triangular structure. Thus, processing is easier, and hence there is also the effect of leading to an improvement in processing precision.

It is possible to understand the present invention from the explanation above, but to more specifically understand the technical significance of the present invention, and to make it possible to more easily carry out the present invention, other specific examples of the present invention are listed below as Examples 3 to 10.

Example 3

The standard profile of this example is set such that the zone radius determined by the zone sequence (1) and the zone radius determined by the zone sequence (2) are incorporated concentrically so as to be overlapped on the same region of the standard profile. The zone sequence (1) is set by Equation 15 noted above with $r_1$=0.57 mm, and P=4 D, and the zone sequence (2) is set by the same Equation 15 noted above with $r_1$=0.5048 mm, and P=2.67 D. The zone radii determined by the zone sequences (1) and (2) are arranged concentrically from the center toward the outer peripheral part within the same region in increasing order of radius, and thereby making constituent zones of the standard profile. For all zones, the phase constant of the standard profile is h=0.6 and $\tau$=0.

The details of this standard profile are shown as Comparative Example 3 in Table 7 and FIG. 17A. Also, the intensity distribution on the optical axis of the standard profile for Comparative Example 3 is shown in FIG. 17B (dashed line). This standard profile generates three main focal point peaks at the positions of 0 D, 2.67 D, and 4 D. Therefore, when using a diffractive lens comprising this standard profile as an ophthalmic lens, for example, an intraocular lens, this is useful as an intraocular lens having three focal points that can be used for far vision, near vision, and also intermediate vision.

TABLE 7

(Example 3)

| A | B Zone sequence (1) Addition power P = 4D | C Zone sequence (2) Addition power P = 2.67D | E | F G H Standard profile (Comparative Example 3) | | | I J Present invention profile (Example 3) | | K Zone pitch (standardized) | L Zone area (standardized) | M Half-value width (calculated value) | N Half-value width (standardized) |
|---|---|---|---|---|---|---|---|---|---|---|---|---|
| Zone No. n | Zone radius(mm) $r_n$ | Zone radius(mm) $r_n$ | Zone No. i | Zone radius(mm) $r_i$ | Phase constant h | Phase shift $\tau$ (radians) | Phase constant h | Phase shift $\tau$ (radians) | $\angle r/\angle r_{max}$ | $S/S_{max}$ | $\angle D$ (diopter) | $\angle D/\angle D_{min}$ |
| 1 | 0.57 | 0.5048 | 1 | 0.5048 | 0.6 | 0 | 0.5 | 0 | 1 | 0.93 | 3.79 | 1.07 |
| 2 | 0.7732 | 0.8150 | 2 | 0.57 | 0.6 | 0 | −0.5 | 0 | 0.13 | 0.26 | 13.86 | 3.93 |
| 3 | 0.9332 | 1.0362 | 3 | 0.7732 | 0.6 | 0 | 0.5 | 0 | 0.40 | 1 | 3.53 | 1.00 |
| 4 | 1.0695 | 1.2179 | 4 | 0.8150 | 0.6 | 0 | −0.5 | 0 | 0.08 | 0.24 | 14.55 | 4.12 |
| 5 | 1.1903 | 1.3758 | 5 | 0.9332 | 0.6 | 0 | 0.5 | 0 | 0.23 | 0.76 | 4.69 | 1.33 |
| 6 | 1.3000 | | 6 | 1.0362 | 0.6 | 0 | 0.5 | 0 | 0.20 | 0.74 | 4.75 | 1.35 |
| 7 | 1.4010 | | 7 | 1.0695 | 0.6 | 0 | −0.5 | 0 | 0.07 | 0.26 | 13.86 | 3.93 |
| 8 | 1.4953 | | 8 | 1.1903 | 0.6 | 0 | 0.5 | 0 | 0.24 | 1 | 3.53 | 1.00 |
| 9 | | | 9 | 1.2179 | 0.6 | 0 | −0.5 | 0 | 0.05 | 0.24 | 14.55 | 4.12 |

TABLE 7-continued (Example 3)

| A Zone No. n | B Zone sequence (1) Addition power P = 4D Zone radius(mm) $r_n$ | C Zone sequence (2) Addition power P = 2.67D Zone radius(mm) $r_n$ | E Zone No. i | F Standard profile (Comparative Example 3) Zone radius(mm) $r_i$ | G Phase constant h | H Phase shift τ (radians) | I Present invention profile (Example 3) Phase constant h | J Phase shift τ (radians) | K Zone pitch (standardized) $\angle r/\angle r_{max}$ | L Zone area (standardized) $S/S_{max}$ | M Half-value width (calculated value) $\angle D$ (diopter) | N Half-value width (standardized) $\angle D/\angle D_{min}$ |
|---|---|---|---|---|---|---|---|---|---|---|---|---|
| 10 | | | 10 | 1.3000 | 0.6 | 0 | 0.5 | 0 | 0.16 | 0.76 | 4.69 | 1.33 |
| 11 | | | 11 | 1.3758 | 0.6 | 0 | 0.5 | 0 | 0.15 | 0.74 | 4.75 | 1.35 |
| 12 | | | 12 | 1.4010 | 0.6 | 0 | −0.5 | 0 | 0.05 | 0.26 | 13.86 | 3.93 |
| 13 | | | 13 | 1.4953 | 0.6 | 0 | 0.5 | 0 | 0.19 | 1 | 3.53 | 1.00 |

However, with the standard profile for Comparative Example 3, generation of peaks (indicated by the arrow in the drawing) based on multi-order light is seen, and there is a significant decrease in gain of the main peak of 0 D.

On the other hand, the present invention profile for Example 3 is such that the blaze of the second, fourth, seventh, ninth, and twelfth zones is reversed when the phase constant of the standard profile is h=0.5, so as to make the phase constant negative and connect the valley and the peak of neighboring zones. Details of the present invention profile for Example 3 are shown together with Comparative Example 3 in Table 7 and FIG. 17A. Also, the intensity distribution on the optical axis of the present invention profile for Example 3 is shown together with Comparative Example 3 in FIG. 17B.

From the results shown in FIG. 17B, we can see that with the present invention profile, multi-order light peaks are eliminated while maintaining the intensity for near and intermediate vision, and there is a significant improvement in peak intensity of 0 D for far vision. Also, with the point spread function, as shown in FIGS. 18A and 18B, the generation of a ring shaped halo in a broad range over the periphery with the Comparative Example 3 is seen (FIG. 18A), but with Example 3, we can see that much of the ring is eliminated and there is a decrease in halo (FIG. 18B).

With the present invention profile, the $\Delta r/\Delta r_{max}$ of the adjustment zone for which the blaze inclination is reversed is maximum at 0.13 of the second zone, and the pitch of all the adjustment zones is narrow. Also, $S/S_{max}$ is 0.26 or less in all the adjustment zones, and the blaze inclination is reversed in the small area zones. These short period zones easily cause multi-order light in the standard profile state, and cause a decrease in gain of main peaks. Also, from the Fourier transform analogy noted above, noise is easily caused at high frequency (peripheral region) in the 0th order focal point image plane, so that halo also stands out. However, by reversing the inclination of those zones, it is possible to suppress the generation of noise and to reduce halo.

Also, $\Delta D/\Delta D_{min}$ of these adjustment zones is 3.93 or greater, and since the half-value width of the intensity distribution is large, it is also possible to improve the gain of main peaks.

Therefore, the present invention profile of this example is useful as a diffractive multi-focal ophthalmic lens that gives three focal points for far, intermediate, and near visions, while further improving vision for far vision than the standard profile as well as reducing nighttime halo.

Example 4

Figure 19A:
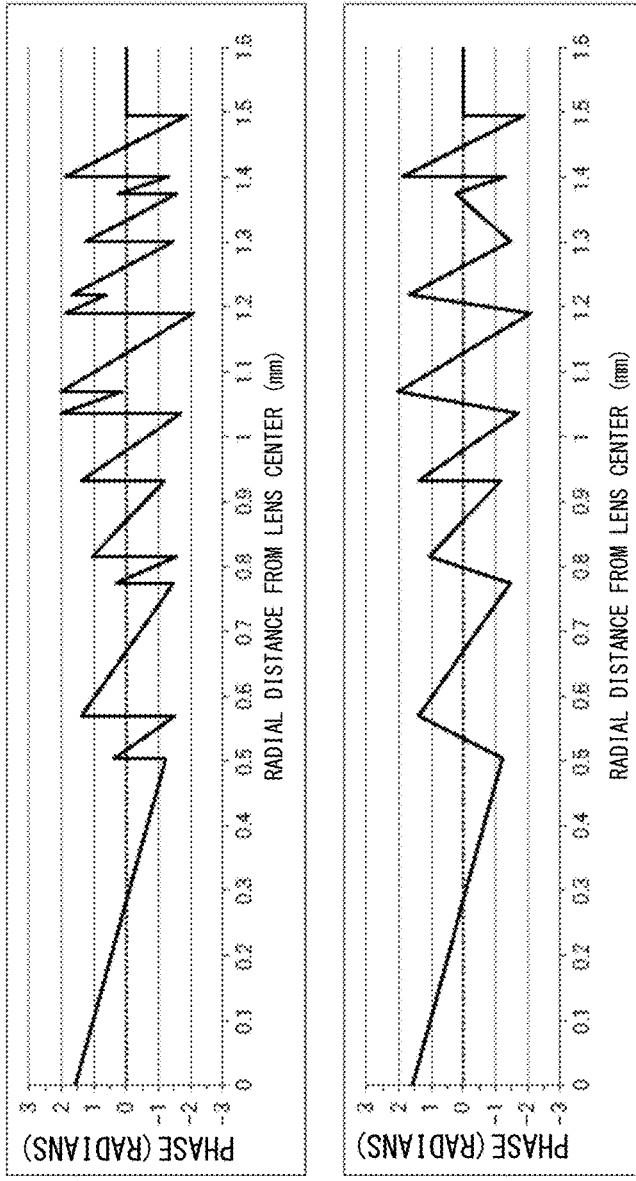
FIGS. 19A and 19B are drawings for explaining the structure and characteristics of the diffractive multi-focal ophthalmic lens as Example 4 of the present invention, where

With Example 4, the details are shown as the present invention profile together with the standard profile for Comparative Example 4 in Table 8 and FIG. 19A. As shown, Example 4 is such that with the standard profile of Example 3, the blaze of the second, fourth, seventh, ninth, and eleventh zones are reversed. Specifically, with Example 3, the second, fourth, seventh, ninth, and twelfth zones had the sign of the inclination of the blaze reversed as adjustment zones, but in this example, instead of the twelfth zone, the blaze of the eleventh zone is reversed as an adjustment zone.

TABLE 8

(Example 4)

| | Standard profile (Comparative Example 4) | | Present invention profile (Example 4) | |
|---|---|---|---|---|
| Zone No. i | Zone radius(mm) $r_i$ | Phase constant h | Phase shift τ (radians) | Phase constant h | Phase shift τ (radians) |
| 1 | 0.5048 | 0.45 | 0.1808 | 0.45 | 0.1808 |
| 2 | 0.57 | 0.3 | −0.5776 | −0.4156 | 0.0726 |
| 3 | 0.7732 | 0.45 | −0.0356 | 0.45 | −0.0356 |
| 4 | 0.8150 | 0.3 | −0.6283 | −0.3949 | −0.2088 |
| 5 | 0.9332 | 0.35 | −0.0678 | 0.35 | −0.0678 |
| 6 | 1.0362 | 0.5 | −0.1582 | 0.5 | −0.1582 |
| 7 | 1.0695 | 0.3 | 1.0996 | −0.5954 | 0.1416 |
| 8 | 1.1903 | 0.65 | −0.0297 | 0.65 | −0.0297 |
| 9 | 1.2179 | 0.2 | 1.2566 | −0.5952 | −0.2019 |
| 10 | 1.3000 | 0.5 | 0.0971 | 0.5 | 0.0971 |
| 11 | 1.3758 | 0.45 | −0.1571 | −0.2729 | −0.6163 |
| 12 | 1.4010 | 0.25 | −0.5443 | 0.25 | −0.5443 |
| 13 | 1.4953 | 0.6 | −0.0143 | 0.6 | −0.0143 |

Figure 19B:
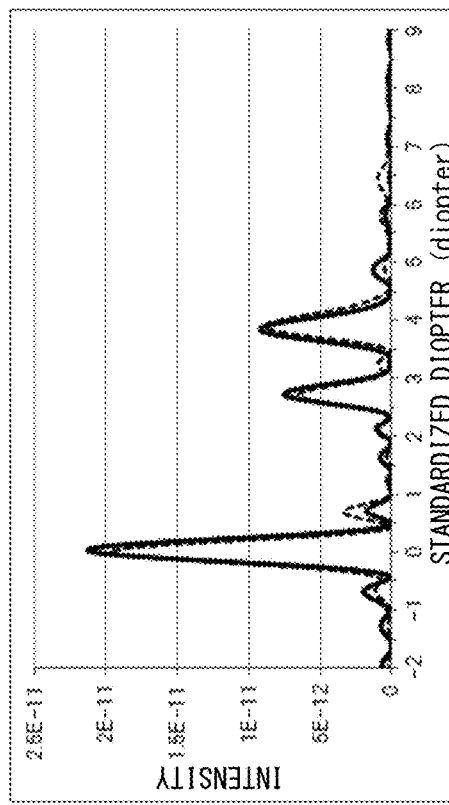

The standard profile for Comparative Example 4 has the same zone radius as that of Comparative Example 3, but as shown in FIG. 19A and Table 8, the phase constant and the phase shift of the blaze are varied. The intensity distribution on the optical axis of the standard profile is shown in FIG. 19B (dashed line), and the point spread function is shown in FIGS. 20A and 20C (dashed line). The standard profile, the same as with Comparative Example 3, generates main focal point peaks at 0 D, 2.67 D, and 4 D. The Comparative Example 4 has smaller multi-order light generation and halo expansion than those of Comparative Example 3 at the standard profile stage, but by applying the present invention profile thereto, it is possible to obtain further reduction of multi-order light and improvement in gain, as well as reduction of halo.

The present invention profile was obtained by reversing the inclination of the blaze of the second, fourth, seventh, ninth, and eleventh zones for the standard profile of this example so as to connect the valley part and the peak part of the neighboring zones (see Table 8, FIG. 19A). Also, the intensity distribution on the optical axis is shown in FIG. 19B, and the point spread function is shown in FIGS. 20B and 20C. By reversing the blaze, we can see that the peak intensity of 0 D is greater than that of the standard profile. Also, with the point spread function, there is a decrease in the ring of the outer periphery that stood out with Comparative Example 4, and we can see that there is further reduction in halo.

The zones for which the blaze is reversed in this example all have a narrow zone pitch with $\Delta r/\Delta r_{max}$ of the eleventh zone being maximum at approximately 0.15. The eleventh zone is positioned near the outer periphery part of the profile, and is positioned to the radially outer side of the radial center in the setting region of the diffraction grating (diffraction grating region) of this example. With the zone positioned at the radially outer side of the grating region in this way, the zone area S is larger by the circumference length becoming larger, and the distribution width on the optical axis also tends to become narrower. However, by using the zone pitch as an index, those zones are also selected as adjustment zones with the assumption that they may cause noise generation of high frequency on the image plane based on the aforementioned Fourier transform analogy.

the zone mainly to have halo noise reduction more than to have improvement in gain of the main peak.

Example 5

This example, with the zone sequences (1) and (2) configuring the standard profile, has the same zone pitch as Example 3 for both zone sequences (1) and (2), but is an item for which the zone sequence (2) is limited to the first to fourth regions so as to make the zone configuration of the standard profile.

The details of the standard profile of this example are shown as Comparative Example 5 in Table 9 and FIG. 21A. With this standard profile, the phase constant of the blaze of the first to tenth zones is h=0.5, and the phase constant and phase shift for the eleventh and twelfth zones are as shown in Table 9. The intensity distribution on the optical axis and the point spread function of the standard profile for Comparative Example 5 are respectively shown in FIG. 21B and FIG. 22A. With this standard profile as well, main peaks are generated at the positions of 0 D, 2.67 D, and 4 D, so that a multi-focal ophthalmic lens can be realized. With this comparative example, the standard profile itself has little loss of light due to multi-order light. However, with the point spread function, a halo pattern with an intensive ring is observed, posing the risk of deterioration in visual power for far vision at night.

TABLE 9

(Example 5)

| A | B Zone sequence (1) Addition power P = 4D | C Zone sequence (2) Addition power P = 2.67D | E | F G H Standard profile (Comparative Example 5) | | | I J Present invention profile (Example 5) | | K Zone pitch (standardized) | L Zone area (standardized) | M Half-value width (calculated value) | N Half-value width (standardized) |
|---|---|---|---|---|---|---|---|---|---|---|---|---|
| Zone No. n | Zone radius(mm) $r_n$ | Zone radius(mm) $r_n$ | Zone No. i | Zone radius(mm) $r_i$ | Phase constant h | Phase shift τ (radians) | Phase constant h | Phase shift τ (radians) | $\angle r/ \angle r_{max}$ | $S/S_{max}$ | $\angle D$ (diopter) | $\angle D/ \angle D_{min}$ |
| 1 | 0.57 | 0.5048 | 1 | 0.5048 | 0.5 | 0 | 0.5 | 0 | 1 | 0.93 | 3.79 | 1.07 |
| 2 | 0.7732 | 0.8150 | 2 | 0.57 | 0.5 | 0 | −0.5 | 0 | 0.13 | 0.26 | 13.86 | 3.93 |
| 3 | 0.9332 | 1.0362 | 3 | 0.7732 | 0.5 | 0 | 0.5 | 0 | 0.40 | 1 | 3.53 | 1.00 |
| 4 | 1.0695 | 1.2179 | 4 | 0.8150 | 0.5 | 0 | −0.5 | 0 | 0.08 | 0.24 | 14.55 | 4.12 |
| 5 | 1.1903 | | 5 | 0.9332 | 0.5 | 0 | 0.5 | 0 | 0.23 | 0.76 | 4.69 | 1.33 |
| 6 | 1.3000 | | 6 | 1.0362 | 0.5 | 0 | 0.5 | 0 | 0.20 | 0.74 | 4.75 | 1.35 |
| 7 | 1.4010 | | 7 | 1.0695 | 0.5 | 0 | −0.5 | 0 | 0.07 | 0.26 | 13.86 | 3.93 |
| 8 | 1.4953 | | 8 | 1.1903 | 0.5 | 0 | 0.5 | 0 | 0.24 | 1 | 3.53 | 1.00 |
| 9 | | | 9 | 1.2179 | 0.5 | 0 | −0.5 | 0 | 0.05 | 0.24 | 14.55 | 4.12 |
| 10 | | | 10 | 1.3000 | 0.5 | 0 | 0.5 | 0 | 0.16 | 0.76 | 4.69 | 1.33 |
| 11 | | | 11 | 1.4010 | 0.4 | −0.7854 | −0.5 | 0 | 0.20 | 1 | 3.53 | 1.00 |
| 12 | | | 12 | 1.4953 | 0.35 | 0.4712 | 0.35 | 0.4712 | 0.19 | 1 | 3.53 | 1.00 |

With Comparative Example 4, there is little generation of multi-order light at the standard profile stage, and for main peak gain as well, the loss is less than that of Comparative Example 3. Thus, with this example, because of the main focus being on reduction of halo, it is possible to add a zone such as with Example 4, which has a narrow zone pitch though its distribution width on the optical axis is narrow, within the group of zones for which the blaze is reversed. $\Delta D/\Delta D_{min}$ of such zone is approximately 1.35, and the intensity distribution on the optical axis of the light emitted from the zone is not that broad, thus its contribution to improvement in gain is tiny. However, it is possible to select The present invention profile for Example 5 is such that with the standard profile, the blaze of the second, fourth, seventh, ninth, and eleventh zones is reversed so as to connect the neighboring valley part and peak part. Details of the present invention profile are shown together with Comparative Example 5 in Table 9 and FIGS. 21A, 21B. Also, the intensity distribution on the optical axis and the point spread function are respectively shown in FIG. 21B and FIGS. 22B, 22C. The original standard profile itself has little loss of light, but with the present invention profile, the loss due to multi-order light is even less. Also, with the point spread function, the ring pattern is eliminated and the luminance is lower than that of the standard profile, and we can see that there is a significant decrease in halo.

The zones for which the blaze is reversed in this example all have a narrow pitch with $\Delta r/\Delta r_{max}$ of the eleventh zone being maximum at approximately 0.2. The eleventh zone is positioned at the outer peripheral part of the diffraction grating, and the zone area S becomes large, but this zone was selected as the target zone in the same way as the eleventh zone of Example 4 noted above. Also, $\Delta D/\Delta D_{min}$ of the eleventh zone is 1, which gives the intensity distribution of the narrowest width. Even though the contribution to improvement in gain of the main peak is very slight, the same as with Example 4, when the main purpose is halo reduction, the zone having a narrow distribution width should also be understood as an item that can be added as a part of the target zones.

Example 6

With Example 6, the details for the present invention profile are shown in Table 10 and FIG. 23A together with the standard profile for Comparative Example 6. As shown, the zone radius determined by the zone sequence (1) and the zone radius determined by the zone sequence (2) are set to be incorporated concentrically so as to be overlapped on the same region of the standard profile. The zone sequence (1) is set by Equation 15 with $r_1$=0.5225 mm and P=4 D, and the zone sequence (2) is set by Equation 15 with $r_1$=0.3695 mm and P=2.67 D. The zones determined by the zone sequences (1) and (2) are arranged from the center toward the outer peripheral part within the same region in increasing order of radius, thereby making constituent zones of the standard profile.

positions of 0 D, 2.67 D, and 4 D. The constituent zone sequences (1) and (2) of the standard profile of this example are set with the same addition power as Example 3, and generate focal points at the same positions as Example 3.

Therefore, the standard profile of this example can also be used as a multi-focal ophthalmic lens for which intermediate vision is possible in addition to far vision and near vision. However, not a few multi-order light is generated, and though the luminance is low in the point spread function shown in FIG. 24A, an expanding halo pattern is observed. Thus, it is necessary to make this halo pattern to be further inconspicuous.

Example 6 has the blaze of the second, fifth, and ninth zones reversed so as to connect the valley part and the peak part of the neighboring zones after slightly modulating the phase constant and the phase shift of the standard profile for Comparative Example 6. With this example, $\Delta r/\Delta r_{max}$ of the second zone is approximately 0.41, of the fifth zone is approximately 0.2, and of the ninth zone is approximately 0.14. The pitch of the second zone having the reversed blaze is not that narrow, but its $\Delta D/\Delta D_{min}$ is approximately 2, and comparably with the fifth and ninth zones, it has the broadest intensity distribution on the optical axis among the constituent zones. Thus, the second zone is also selected as a preferable zone for reversing the blaze. $S/S_{max}$ of the second zone is 0.5, and has the same area as the fifth and ninth zones, which is the smallest area among the constituent zones.

With the present invention profile of Example 6 having the reversed blazes in this way, we can see that the intensity distribution on the optical axis (see FIG. 23B) has reduced multi-order light, and the peak intensity of the 0 D position

TABLE 10

(Example 6)

| A | B Zone sequence (1) Addition power P = 4D | C Zone sequence (2) Addition power P = 2.67D | E | F Standard profile (Comparative Example 6) | G | H | I Present invention profile (Example 6) | J | K Zone pitch (standardized) | L Zone area (standardized) | M Half-value width (calculated value) | N Half-value width (standardized) |
|---|---|---|---|---|---|---|---|---|---|---|---|---|
| Zone No. n | Zone radius(mm) $r_n$ | Zone radius(mm) $r_n$ | Zone No. i | Zone radius(mm) $r_i$ | Phase constant h | Phase shift τ (radians) | Phase constant h | Phase shift τ (radians) | $\angle r/\angle r_{max}$ | $S/S_{max}$ | $\angle D$ (diopter) | $\angle D/\angle D_{min}$ |
| 1 | 0.5225 | 0.3695 | 1 | 0.3695 | 0.3542 | −0.3482 | 0.3308 | −0.2015 | 1 | 0.5 | 7.08 | 2.01 |
| 2 | 0.7389 | 0.7389 | 2 | 0.5225 | 0.2351 | −0.1886 | −0.3939 | −0.0033 | 0.41 | 0.5 | 7.10 | 2.01 |
| 3 | 0.9050 | 0.9775 | 3 | 0.7389 | 0.5375 | −0.4164 | 0.4964 | −0.3253 | 0.59 | 1 | 3.53 | 1.00 |
| 4 | 1.0450 | 1.1683 | 4 | 0.9050 | 0.5727 | 0.3055 | 0.5240 | 0.2387 | 0.45 | 1 | 3.53 | 1.00 |
| 5 | 1.1683 | 1.3321 | 5 | 0.9775 | 0.2785 | −0.1697 | −0.3427 | −0.3308 | 0.20 | 0.5 | 7.08 | 2.01 |
| 6 | 1.2798 | 1.4778 | 6 | 1.0450 | 0.2819 | 0.0803 | 0.2571 | −0.0619 | 0.18 | 0.5 | 7.10 | 2.01 |
| 7 | 1.3824 | | 7 | 1.1683 | 0.5568 | −0.3555 | 0.5116 | −0.2778 | 0.33 | 1 | 3.53 | 1.00 |
| 8 | 1.4778 | | 8 | 1.2798 | 0.5679 | 0.3208 | 0.5202 | 0.2506 | 0.30 | 1 | 3.53 | 1.00 |
| 9 | 1.5675 | | 9 | 1.3321 | 0.2805 | −0.1453 | −0.3419 | −0.3097 | 0.14 | 0.5 | 7.08 | 2.01 |
| 10 | | | 10 | 1.3824 | 0.2820 | 0.0981 | 0.2579 | −0.0460 | 0.14 | 0.5 | 7.10 | 2.01 |
| 11 | | | 11 | 1.4778 | 0.5596 | −0.3469 | 0.5137 | −0.2710 | 0.26 | 1 | 3.53 | 1.00 |
| 12 | | | 12 | 1.5675 | 0.5663 | 0.3257 | 0.5190 | 0.2544 | 0.24 | 1 | 3.53 | 1.00 |

Here, the addition power of the zone sequence (1) and the zone sequence (2) that form the standard profile are the same as those of Example 3, but the respective first zone radii of these are different from those of Example 3. Therefore, the zone radius of the standard profile is also different. The blaze of this standard profile is set with the phase constant and the phase shift shown in Table 10, and exhibits the intensity distribution on the optical axis shown by the dashed line in FIG. 23B. The main focal point peaks are generated at the used for far vision increases, thereby leading to improvement in gain. Also, with the point spread function of the present invention profile shown in FIGS. 24B and 24C, we can see that the noise is reduced compared with the standard profile, and there is less ring expansion. This Example 6 comprises the zone sequences of the same addition power as Example 3, though the zone radius is different. In this way, we can see from this example that it is possible to equivalently apply the present invention to the profile of a different mode that forms focal points at the same positions.

Example 7

With Example 7, the details for the present invention profile are shown together with the standard profile for Comparative Example 7 in Table 11 and FIG. 25A. As shown, the zone radius determined with the zone sequence (1) and the zone radius determined with the zone sequence (2) are set to be incorporated concentrically so as to be overlapped on the same region of the standard profile. The zone sequence (1) is set by Equation 15 with $r_1=0.5225$ mm and P=4 D, and the zone sequence (2) is set by Equation 15 with $r_1=0.58$ mm and P=2 D. The zones determined with the zone sequences (1) and (2) are arranged from the center toward the outer peripheral part within the same region in increasing order of radius, thereby making constituent zones of the standard profile.

The zones for which the inclination of the blaze is reversed all have a narrow pitch with $\Delta r/\Delta r_{max}$ of the second zone being maximum at approximately 0.11. Also, $S/S_{max}$ is approximately 0.23 for all such zones, having the smallest area among the constituent zones. Furthermore, $\Delta D/\Delta D_{min}$ is approximately 4.33, thus the zones with the broadest intensity distribution on the optical axis are selected among the constituent zones.

When the blaze of a specific zone is reversed in this way, with the intensity distribution on the optical axis shown in FIG. 25B, generation of multi-order light is suppressed, and the light of that amount is distributed to an increase in the peak intensity of 0 D and 2 D, and we can see that there is an improvement in gain of each of the peaks. Also, as shown in FIGS. 26B and 26C, the rings, which expanded to the outer peripheral part with Comparative Example 7 (FIG. 26A) for the standard profile, becomes paler and inconspicu-

TABLE 11

(Example 7)

| A Zone No. n | B Zone sequence (1) Addition power P = 4D Zone radius(mm) $r_n$ | C Zone sequence (2) Addition power P = 2D Zone radius(mm) $r_n$ | E Zone No. i | F Zone radius(mm) $r_i$ | G Standard profile (Comparative Example 7) Phase constant h | H Standard profile (Comparative Example 7) Phase shift τ (radians) | I Present invention profile (Example 7) Phase constant h | J Present invention profile (Example 7) Phase shift τ (radians) | K Zone pitch (standardized) $\angle r / \angle r_{max}$ | L Zone area (standardized) $S/S_{max}$ | M Half-value width (calculated value) $\angle D$ (diopter) | N Half-value width (standardized) $\angle D / \angle D_{min}$ |
|---|---|---|---|---|---|---|---|---|---|---|---|---|
| 1 | 0.5225 | 0.58 | 1 | 0.5225 | 0.6165 | −0.3042 | 0.4110 | −0.2028 | 1 | 1 | 3.54 | 1.00 |
| 2 | 0.7389 | 0.9394 | 2 | 0.58 | 0.1379 | 0.1532 | −0.4081 | −0.2120 | 0.11 | 0.23 | 15.33 | 4.33 |
| 3 | 0.9050 | 1.1952 | 3 | 0.7389 | 0.4631 | 0.1501 | 0.3087 | 0.1000 | 0.30 | 0.77 | 4.64 | 1.31 |
| 4 | 1.0450 | 1.4051 | 4 | 0.9050 | 0.5886 | −0.3266 | 0.5655 | −0.2722 | 0.32 | 1 | 3.54 | 1.00 |
| 5 | 1.1683 | | 5 | 0.9394 | 0.1392 | 0.2143 | −0.5656 | −0.2720 | 0.07 | 0.23 | 15.33 | 4.33 |
| 6 | 1.2798 | | 6 | 1.0450 | 0.4634 | 0.2062 | 0.4427 | 0.1140 | 0.20 | 0.77 | 4.64 | 1.31 |
| 7 | 1.3824 | | 7 | 1.1683 | 0.5947 | −0.2903 | 0.5447 | −0.2903 | 0.24 | 1 | 3.54 | 1.00 |
| 8 | 1.4778 | | 8 | 1.1952 | 0.1397 | 0.2300 | −0.5723 | −0.2035 | 0.05 | 0.23 | 15.33 | 4.33 |
| 9 | | | 9 | 1.2798 | 0.4627 | 0.2223 | 0.4248 | 0.2601 | 0.16 | 0.77 | 4.64 | 1.31 |
| 10 | | | 10 | 1.3824 | 0.5965 | −0.2780 | 0.5465 | −0.2780 | 0.20 | 1 | 3.54 | 1.00 |
| 11 | | | 11 | 1.4051 | 0.1397 | 0.2364 | −0.5722 | −0.1974 | 0.04 | 0.23 | 15.33 | 4.33 |
| 12 | | | 12 | 1.4778 | 0.4623 | 0.2300 | 0.4242 | 0.2675 | 0.14 | 0.77 | 4.64 | 1.31 |

The phase constant and the phase shift of the blaze of each zone with this standard profile are set as shown in Table 11 noted above as Comparative Example 7. The intensity distribution on the optical axis of the standard profile is shown in FIG. 25B. Here, the main focal point peaks are generated at the positions of 0 D, 2 D, and 4 D. Since the addition power of the zone sequence (2) is 2 D, a peak also appears at the 2 D position with the standard profile having this zone sequence as a constituent component. When using this profile as an intraocular lens, the 2 D peak can also be utilized as a focal point for intermediate vision, and it is possible to have a multi-focal intraocular lens for which the intermediate vision region is slightly shifted to the far side.

However, multi-order light is generated with the standard profile, and with the point spread function (FIG. 26A), pale rings are generated over the outer periphery. In light of that, Example 7 is such that with the blaze of the standard profile, after slightly modulating the phase constant and the phase shift as shown in Table 11, the blaze of the second, fifth, eighth, and eleventh zones is reversed so as to connect the valley part and the peak part of the neighboring zones. In Table 11, the phase constant of the zone having the reversed blaze is negative.

ous. Thus, the present invention profile has reduced halo, and is useful as a multi-focal intraocular lens that can be used for near, intermediate, and far visions.

Example 8

With Example 8, the details are shown in Table 12 and FIG. 27A for the present invention profile, together with Comparative Example 8 for the standard profile. A shown, the zone radius determined by the zone sequence (1) and the zone radius determined by the zone sequence (2) are set to be incorporated concentrically so as to be overlapped on the same region of the standard profile. The zone sequence (1) is set by Equation 15 with $r_1=0.5225$ mm and P=4 D, and the zone sequence (2) is set by Equation 15 with $r_1=0.6399$ mm and P=1.6 D. The zones determined by the zone sequences (1) and (2) are arranged from the center toward the outer peripheral part within the same region in increasing order of radius, thereby making constituent zones of Comparative Example 8 used as the standard profile.

TABLE 12

(Example 8)

| A | B Zone sequence (1) Addition power P = 4D | C Zone sequence (2) Addition power P = 1.6D | E | F Standard profile (Comparative Example 8) | | G | H | I Present invention profile (Example 8) | | J | K Zone pitch (stan-dard-ized) | L Zone area (stan-dard-ized) | M Half-value width (calcu-lated value) | N Half-value width (stan-dard-ized) |
|---|---|---|---|---|---|---|---|---|---|---|---|---|---|---|
| Zone No. n | Zone radius(mm) $r_n$ | Zone radius(mm) $r_n$ | Zone No. i | Zone radius(mm) $r_i$ | | Phase constant h | Phase shift τ (radians) | Phase constant h | | Phase shift τ (radians) | ∠r/∠$r_{max}$ | S/$S_{max}$ | ∠D (diopter) | ∠D/∠$D_{min}$ |
| 1 | 0.5225 | 0.6399 | 1 | 0.5225 | | 0.5715 | −0.3188 | 0.4980 | | −0.1821 | 1 | 1 | 3.53 | 1.00 |
| 2 | 0.7389 | 1.0450 | 2 | 0.6399 | | 0.2556 | −0.4037 | −0.3609 | | −0.6126 | 0.22 | 0.5 | 7.08 | 2.01 |
| 3 | 0.9050 | 1.3321 | 3 | 0.7389 | | 0.2685 | 0.1490 | −0.3682 | | 0.4213 | 0.19 | 0.5 | 7.08 | 2.01 |
| 4 | 1.0450 | 1.5675 | 4 | 0.9050 | | 0.5435 | 0.1113 | 0.4820 | | 0.0636 | 0.32 | 1 | 3.53 | 1.00 |
| 5 | 1.1683 | | 5 | 1.0450 | | 0.5210 | −0.7195 | 0.4691 | | −0.4112 | 0.27 | 1 | 3.53 | 1.00 |
| 6 | 1.2798 | | 6 | 1.1683 | | 0.5504 | 0.6272 | 0.4859 | | 0.3584 | 0.24 | 1 | 3.53 | 1.00 |
| 7 | 1.3824 | | 7 | 1.2798 | | 0.5359 | −0.2722 | 0.4777 | | −0.1556 | 0.21 | 1 | 3.53 | 1.00 |
| 8 | 1.4778 | | 8 | 1.3321 | | 0.2676 | −0.2832 | −0.3597 | | −0.5261 | 0.10 | 0.5 | 7.08 | 2.01 |
| 9 | 1.5675 | | 9 | 1.3824 | | 0.2709 | 0.2242 | −0.3611 | | 0.4820 | 0.10 | 0.5 | 7.08 | 2.01 |
| 10 | | | 10 | 1.4778 | | 0.5419 | 0.1839 | 0.4811 | | 0.1051 | 0.18 | 1 | 3.53 | 1.00 |
| 11 | | | 11 | 1.5675 | | 0.5333 | −0.6808 | 0.4762 | | −0.3890 | 0.17 | 1 | 3.53 | 1.00 |

The intensity distribution on the optical axis of the standard profile is shown by dashed lines in FIG. 27B, and the main focal point peaks are generated at the positions of 0 D, 1.6 D, and 4 D. The focal point peak of the position of 1.6 D is generated based on the addition power of the zone sequence (2). If Comparative Example 8 comprising this standard profile is used as an ophthalmic lens, for example an intraocular lens, the peak of 1.6 D is the focal point position available for viewing objects at the point of approximately 1 m in front. Thus, with the intraocular lens, this is useful as an intraocular lens having three focal points for viewing objects at the point of approximately 1 m as well, in addition to far and near objects.

However, not an inconsiderable degree of loss occurs due to multi-order light. Also, as shown in FIG. 28A which is the point spread function of Comparative Example 8, the ring-shaped halo stands out, and there is the risk of impairing visual power for far vision at night.

Here, the present invention profile of Example 8 is such that after slightly modulating the phase constant and the phase shift of the blaze of the standard profile for Comparative Example 8, the blaze of the second, third, eighth, and ninth zones are reversed so as to connect the valley part and the peak part of the neighboring zones. The phase constant of the zone having the reversed blaze is negative in Table 12. These blaze-reversed zones all have a narrow pitch with $\Delta r/\Delta r_{max}$ of the second zone being maximum at approximately 0.22. Besides, $S/S_{max}$ is 0.5 for all such zones, having the smallest area among the constituent zones. Also, $\Delta D/\Delta D_{min}$ is approximately 2, thus the items with a broad intensity distribution on the optical axis are selected among the constituent zones.

The intensity distribution in the optical axis direction of the present invention profile for Example 8 is shown in FIG. 27B, As shown, the multi-order light is reduced compared with Comparative Example 8 which is the standard profile, and the intensity of the peak of the 0 D position increases by that amount. Also, the intensity of the peak of 4 D becomes slightly higher, and we can see that there is an improvement in gain. With the point spread function of Example 8 shown in FIGS. 28B and 28C, the ring at the outer peripheral part is eliminated, and we can see that the halo expansion is suppressed compared with that of the standard profile. With this profile, the blazes of two continuous neighboring zones, namely the second and third zones, and the eighth and ninth zones, are reversed. This kind of mode for which the blazes of continuous zones are reversed can be preferably used in the present invention. Thus, the diffractive lens based on this example has reduced halo, and is useful as a multi-focal intraocular lens for which far vision, near vision, and intermediate vision are possible.

Example 9

With Example 9, the details for the present invention profile are shown in Table 13 and FIG. 29A together with the standard profile for Comparative Example 9. As shown, the zone radius determined by the zone sequence (1) and the zone radius determined by the zone sequence (2), and additionally the zone radius determined by the zone sequence (3) are set to be incorporated concentrically so as to be overlapped on the same region of the standard profile. The zone sequence (1) is set by Equation 15 with $r_1$=0.5396 and P=3.75 D, the zone sequence (2) is set by Equation 15 with $r_1$=0.4406 mm and P=2.81 D, and the zone sequence (3) is set by Equation 15 with $r_1$=0.5396 mm and P=1.88 D. The zones determined by the zone sequences (1), (2), and (3) are arranged from the center toward the outer peripheral part within the same region in increasing order of radius, thereby making constituent zones of the standard profile.

TABLE 13

(Example 9)

| A Zone No. n | B Zone sequence (1) Addition power P = 3.75D Zone radius (mm) $r_n$ | C Zone sequence (2) Addition power P = 2.81D Zone radius (mm) $r_n$ | D Zone sequence (3) Addition power P = 1.88D Zone radius (mm) $r_n$ | E Zone No. i | F Standard profile (Comparative Example 9) Zone radius (mm) $r_n$ | G Phase constant h | H Phase shift τ (radians) | I Present invention profile (Example 9) Phase constant h | J Phase shift τ (radians) | K Zone pitch (standardized) $\angle r / \angle r_{max}$ | L Zone area (standardized) $S/S_{max}$ | M Half-value width (calculated value) $\angle D$ (diopter) | N Half-value width (standardized) $\angle D/\angle D_{min}$ |
|---|---|---|---|---|---|---|---|---|---|---|---|---|---|
| 1 | 0.5396 | 0.4406 | 0.5396 | 1 | 0.4406 | 0.3404 | −0.2839 | 0.3358 | −0.1124 | 1 | 0.67 | 5.02 | 1.52 |
| 2 | 0.7632 | 0.7632 | 0.9347 | 2 | 0.5396 | 0.1057 | −0.7427 | −0.4051 | 0.1053 | 0.22 | 0.33 | 9.96 | 3.02 |
| 3 | 0.9347 | 0.9852 | 1.2066 | 3 | 0.7632 | 0.4388 | 0.0599 | 0.4259 | 0.0400 | 0.51 | 1 | 3.30 | 1.00 |
| 4 | 1.0793 | 1.1657 | 1.4277 | 4 | 0.9347 | 0.5913 | −0.2125 | 0.5413 | −0.2125 | 0.39 | 1 | 3.30 | 1.00 |
| 5 | 1.2066 | 1.3218 | | 5 | 0.9852 | 0.2051 | 0.7413 | −0.5124 | −0.3033 | 0.11 | 0.33 | 9.96 | 3.02 |
| 6 | 1.3218 | 1.4613 | | 6 | 1.0793 | 0.4010 | 0.0940 | 0.3684 | 0.1489 | 0.21 | 0.67 | 5.02 | 1.52 |
| 7 | 1.4277 | | | 7 | 1.1657 | 0.4408 | −0.7018 | 0.4048 | −0.2516 | 0.20 | 0.67 | 5.02 | 1.52 |
| 8 | 1.5263 | | | 8 | 1.2066 | 0.2228 | −0.2732 | −0.6031 | 0.3714 | 0.09 | 0.33 | 9.96 | 3.02 |
| 9 | | | | 9 | 1.3218 | 0.6754 | 0.0468 | 0.6170 | 0.3280 | 0.26 | 1 | 3.30 | 1.00 |
| 10 | | | | 10 | 1.4277 | 0.7474 | −0.1883 | 0.5476 | −0.1760 | 0.24 | 1 | 3.30 | 1.00 |
| 11 | | | | 11 | 1.4613 | 0.2513 | 0.4441 | −0.5144 | −0.2803 | 0.08 | 0.33 | 9.96 | 3.02 |
| 12 | | | | 12 | 1.5263 | 0.5039 | 0.5848 | 0.3678 | 0.1803 | 0.15 | 0.67 | 5.02 | 1.52 |

The intensity distribution on the optical axis of the standard profile for Comparative Example 9 shown in FIG. 29A is shown by a dashed line in FIG. 29B. From this, we can see that a peak is generated at the point of approximately 1.88 D in addition to the three focal point peaks of 0 D, 2.81 D, and 3.75 D. In other words, with this standard profile, four focal points can be generated. This is a multifocal lens for which 0 D is for far vision, 3.75 D is for near vision for viewing a point of approximately 38 cm in front, 2.81 D is for a first intermediate vision for viewing approximately 50 cm in front, and 1.88 D is for a second intermediate vision for viewing approximately 75 cm in front, and is useful as an ophthalmic lens having four focal points.

However, with the standard profile, not a few multi-order light is generated, and as shown in FIG. 30A, a ring-shaped halo is generated with the point spread function.

In light of that, the present invention profile of this Example 9 is such that after slightly modulating the phase constant and the phase shift of the standard profile for the Comparative Example 9, the blaze of the second, fifth, eighth, and eleventh zones is reversed so as to connect the valley part and the peak part of the neighboring zones. The phase constant of the zones having the reversed blaze is negative in Table 13. With this example, the blaze-reversed zones all have a narrow pitch with $\Delta r/\Delta r_{max}$ of the second zone being maximum at approximately 0.22. Also, $S/S_{max}$ is 0.33 for all such zones, having the smallest area among the constituent zones. Also, $\Delta D/\Delta D_{min}$ is approximately 3, thus the items with a broad intensity distribution on the optical axis are selected among the constituent zones.

The intensity distribution in the optical axis direction of the present invention profile for Example 9 is shown in FIG. 29B. As shown, the multi-order light is suppressed compared with Comparative Example 9 which is the standard profile, and we can see that the intensity of the 0 D peak increases, and there is an improvement in gain. Also, with the point spread function of Example 9 shown in FIGS. 30B and 30C, we can see that the halo expansion is smaller than that of the standard profile, and becomes inconspicuous.

As described, this Example 9 is an example using an item that becomes a four focal point lens with the standard profile. The present invention is also suitable for this multifocal lens. Also, from each of the examples described above, it is possible to understand that the present invention can also similarly be used for a profile providing focal points more than four focal points.

Example 10

With Example 10, the details for the present invention profile are shown together with the standard profile for Comparative Example 10 in Table 14 and FIG. 31A. As shown, the zone radius determined by the zone sequence (1) and the zone radius determined by the zone sequence (2) are set to be incorporated concentrically so as to be overlapped on the same region of the standard profile. The zone sequence (1) is set by Equation 15 with $r_1$=0.7389 mm and P=2 D, and the zone sequence (2) is set by Equation 15 with $r_1$=0.6033 and P=1.5 D. The zone radii determined by the zone sequences (1) and (2) are arranged from the center toward the outer peripheral part within the same region in increasing order of radius, thereby making constituent zones of the standard profile.

TABLE 14

(Example 10)

| A Zone No. n | B Zone sequence (1) Addition power P = 2D Zone radius(mm) $r_n$ | C Zone sequence (2) Addition power P = 1.5D Zone radius(mm) $r_n$ | E Zone No. i | F Standard profile (Comparative Example 10) Zone radius(mm) $r_i$ | F Standard profile (Comparative Example 10) Phase constant h | F Standard profile (Comparative Example 10) Phase shift τ (radians) | I Present invention profile (Example 10) Phase constant h | J Present invention profile (Example 10) Phase shift τ (radians) | K Zone pitch (standardized) $\angle r/\angle r_{max}$ | L Zone area (standardized) $S/S_{max}$ | M Half-value width (calculated) $\angle D$ (diopter) | N Half-value width (standardized) $\angle D/\angle D_{min}$ |
|---|---|---|---|---|---|---|---|---|---|---|---|---|
| 1 | 0.7389 | 0.6033 | 1 | 0.6033 | 0.4766 | −0.2406 | 0.3858 | −0.1124 | 1 | 0.67 | 2.67 | 1.49 |
| 2 | 1.0450 | 1.0450 | 2 | 0.7389 | 0.1655 | −0.3729 | −0.4244 | 0.0089 | 0.22 | 0.33 | 5.32 | 2.97 |
| 3 | 1.2798 | 1.3491 | 3 | 1.0450 | 0.6079 | −0.2893 | 0.4886 | −0.1929 | 0.51 | 1 | 1.79 | 1.00 |
| 4 | 1.4778 | 1.5962 | 4 | 1.2798 | 0.6317 | 0.2146 | 0.5045 | 0.1430 | 0.39 | 1 | 1.79 | 1.00 |
| 5 | 1.6523 | 1.8100 | 5 | 1.3491 | 0.2082 | 0.0893 | −0.3821 | −0.2414 | 0.11 | 0.33 | 5.32 | 2.97 |
| 6 | 1.8100 | 2.0010 | 6 | 1.4778 | 0.4164 | 0.0121 | 0.3318 | −0.0835 | 0.21 | 0.67 | 2.67 | 1.49 |
| 7 | 1.9550 | | 7 | 1.5962 | 0.4152 | −0.0874 | 0.3673 | 0.0763 | 0.20 | 0.67 | 2.67 | 1.49 |
| 8 | 2.0900 | | 8 | 1.6523 | 0.2071 | −0.1576 | −0.4191 | 0.2389 | 0.09 | 0.33 | 5.32 | 2.97 |
| 9 | | | 9 | 1.8100 | 0.6214 | −0.2471 | 0.5476 | −0.1647 | 0.26 | 1 | 1.79 | 1.00 |
| 10 | | | 10 | 1.9550 | 0.6277 | 0.2270 | 0.5518 | 0.1513 | 0.24 | 1 | 1.79 | 1.00 |
| 11 | | | 11 | 2.0010 | 0.2086 | 0.1128 | −0.4155 | −0.2770 | 0.08 | 0.33 | 5.32 | 2.97 |
| 12 | | | 12 | 2.0900 | 0.4168 | 0.0331 | 0.3658 | −0.1207 | 0.15 | 0.67 | 2.67 | 1.49 |

The intensity distribution on the optical axis of the standard profile for Comparative Example 10 shown in FIG. 31A is shown by a dashed line in FIG. 31B. The intensity distribution on the optical axis of the standard profile is such that main peaks are generated at points of 0 D, 1.5 D, and 2 D. The diffractive multi-focal ophthalmic lens comprising this standard profile is useful as a multi-focal contact lens for typical presbyopia patients.

Specifically, for patients for which an intraocular lens is used, such as cataract patients, for example, as their own crystalline lens is removed, power of accommodation is lost. Thus, it is necessary for the near vision focal point position for reading to be equivalent to 4 D as an intraocular lens by itself. However, with typical presbyopia patients for which their own power of accommodation has not decreased so much, a contact lens prescription is preferable, and with contact lenses, it is sufficient to have the equivalent of 2 D for the focal point position required for the lens by itself with the help of one's own residual power of accommodation. Therefore, with this example, by allocating 2 D for near vision, 1.5 D for intermediate vision, and 0 D for far vision, this is useful as a contact lens having three focal points for presbyopia patients with their own power of accommodation remaining. With this prescription example as well, since a focal point is set for intermediate vision, visual power is ensured broadly, not only for far vision, but also from reading distance to a distance for viewing a computer screen.

However, with this standard profile for Comparative Example 10, multi-order light is generated as shown by the dashed line in FIG. 31B, and the generation of halo in the point spread function shown in FIG. 32A is also observed.

In light of that, the present invention profile of Example 10 is such that after slightly modulating the phase constant and the phase shift of the standard profile, the blaze of the second, fifth, eighth, and eleventh zones is reversed so as to connect the valley part and the peak part of the neighboring zones. The phase constant of the zones having the reversed blaze is negative in Table 14 noted above. With this Example 10, the blaze-reversed zones all have a narrow pitch with $\Delta r/\Delta r_{max}$ of the second zone being maximum at approximately 0.22. Also, $S/S_{max}$ is 0.33 for all such zones, having the smallest area among the constituent zones. Also, $\Delta D/\Delta D_{min}$ is 2.97, thus the items with a broad intensity distribution on the optical axis are selected among the constituent zones.

As shown in FIG. 31B, we can see that with the intensity distribution on the optical axis of the present invention profile for Example 10, compared to the standard profile, the multi-order light is reduced, the 0 D peak intensity is increased, and gain is improved. Also, with the point spread function of Example 10 shown in FIGS. 32B and 32C, we can see that compared to Comparative Example 10 for the standard profile, the peripheral ring-shaped noise is reduced, and there is less halo expansion.

Therefore, the multi-focal ophthalmic lens for this Example 10 is useful as a multi-focal contact lens for which halo is suppressed.

As can be seen specifically from the description in Examples 1 to 10 and Comparative Examples 1 to 10 above, the standard profile for which the diffraction grating comprising a blaze shaped phase function is set by a plurality of concentric zones comprising a structure for which a plurality of zone sequences given by Equation 15 are overlapped can generate a plurality of focal points. However, a decrease in gain due to generation of multi-order light cannot be avoided, and also, there is the problem that halo is caused for which a ring or circle of light stands out. With the present invention profile for which the inclination of the blaze of specific zones is reversed in this standard profile, it is possible to obtain a diffractive multi-focal ophthalmic lens for which the generation of multi-order light is suppressed as well as gain of the main focal point peaks is improved, and furthermore, halo is reduced.

Also, with the present invention, when selecting the specific zones for which the inclination of the blaze is reversed, as described above, it is preferable to take into consideration the area or pitch of the zone, or the width (half-value width, etc.) of the intensity distribution on the optical axis in zone units.

Here, as the selection criterion for the zone pitch, for example it is possible to use the aforementioned $\Delta r/\Delta r_{max}$. It is desirable to select a zone for which $\Delta r/\Delta r_{max}$ is 0.5 or less, more preferable that $\Delta r/\Delta r_{max}$ be 0.45 or less, and especially preferable that $\Delta r/\Delta r_{max}$ be 0.25 or less. Especially in the region positioned to the radially outer side of the radial center in the region in which the diffraction grating is provided, or the region positioned to the radially outer side of the radial center of the lens optical part that imparts an optical effect on the eye optical system, it is preferable that a zone for which $\Delta r/\Delta r_{max}$ is 0.25 or less be selected as the zone for setting a reversed-inclination blaze.

Also, instead of selecting a specific zone using the zone pitch as the selection criterion, or in addition, it is also possible to use the zone area as the selection criterion. For example, with the second zone in Example 6, the zone pitch is not that narrow, but with respect to the area, the second zone has the smallest area among the constituent zones, thereby being selected as the target zone. In particular, with the region positioned to the radially inner side of the radial center in the region in which the diffraction grating is provided, or the region positioned to the radially inner side of the radial center of the lens optical part that imparts an optical effect on the eye optical system, it may be effective to use area as the selection criterion. When using area as the selection criterion, it is possible to use the aforementioned $S/S_{max}$, for example. When using $S/S_{max}$, it is preferable to select a zone for which $S/S_{max}$ is 0.5 or less, and more preferable that $S/S_{max}$ be 0.35 or less.

Even furthermore, instead of selecting a specific zone using the zone pitch or area as the selection criterion, or in addition, it is also possible to use the width of the intensity distribution on the optical axis due to emitted light from the zone as the selection criterion. For the width of the intensity distribution of a prescribed zone, it is possible to use as the selection criterion the width $\Delta D$ of a prescribed reference value which will be 30%, 50%, or 60%, etc., relative to the maximum intensity of the peak, for example. When using this width of the intensity distribution on the optical axis as the selection criterion, it is possible to use the aforementioned $\Delta D/\Delta D_{min}$, for example. When using $\Delta D/\Delta D_{min}$, it is preferable to select a zone for which $\Delta D/\Delta D_{min}$ is 2 or greater, and more preferable that $\Delta D/\Delta D_{min}$ be 2.5 or greater. Especially in the region positioned to the radially inner side of the radial center in the region in which the diffraction grating is provided, or in the region positioned to the radially inner side of the radial center of the lens optical part that imparts an optical effect on the eye optical system, it may be effective to use as the selection criterion the width of the intensity distribution on the optical axis due to emitted light from the zone.

With the target zones selected using these selection criteria according to the present invention, it is not necessary to reverse the inclination of the blaze for all the applicable target zones. As can be understood from the illustrations shown using the examples or from the results of investigating image-formation characteristics, by reversing the inclination of the blaze for at least one zone among the target zones, it is possible to exhibit the effects of the invention such as halo suppression, etc.

Also, though a contact lens and IOL are specifically illustrated as the aforementioned examples, the optical characteristics expressed by the diffraction grating can be understood to be basically the same as each other. Therefore, as long as the environmental condition in which the lens is used is taken into consideration, the examples specified as the contact lens or IOL can be understood without distinguishing each other. Besides, for an ICL and eyeglass lenses as well, these examples can be grasped as the examples of the present invention.

Yet furthermore, as the mode of reversing the inclination of the blaze shaped phase function in the adjustment zone according to the present invention, either a straight line or a curve can be acceptable as illustrated in FIGS. 10 to 14, etc. Moreover, the mode of the applicable blaze shaped phase function in the standard profile before reversing the blaze is not limited to a specific shape, as illustrated in FIGS. 2A-2D. The inclination angle of the applicable blaze in the standard profile can be grasped as including the angles for which the plus inclination is 0. Therefore, for example in a case of the square wave blaze shape shown in FIG. 2C as well, by setting any minus inclination angle as shown in the aforementioned examples for the applicable zones, it is possible to use the present invention.

Figure 4:
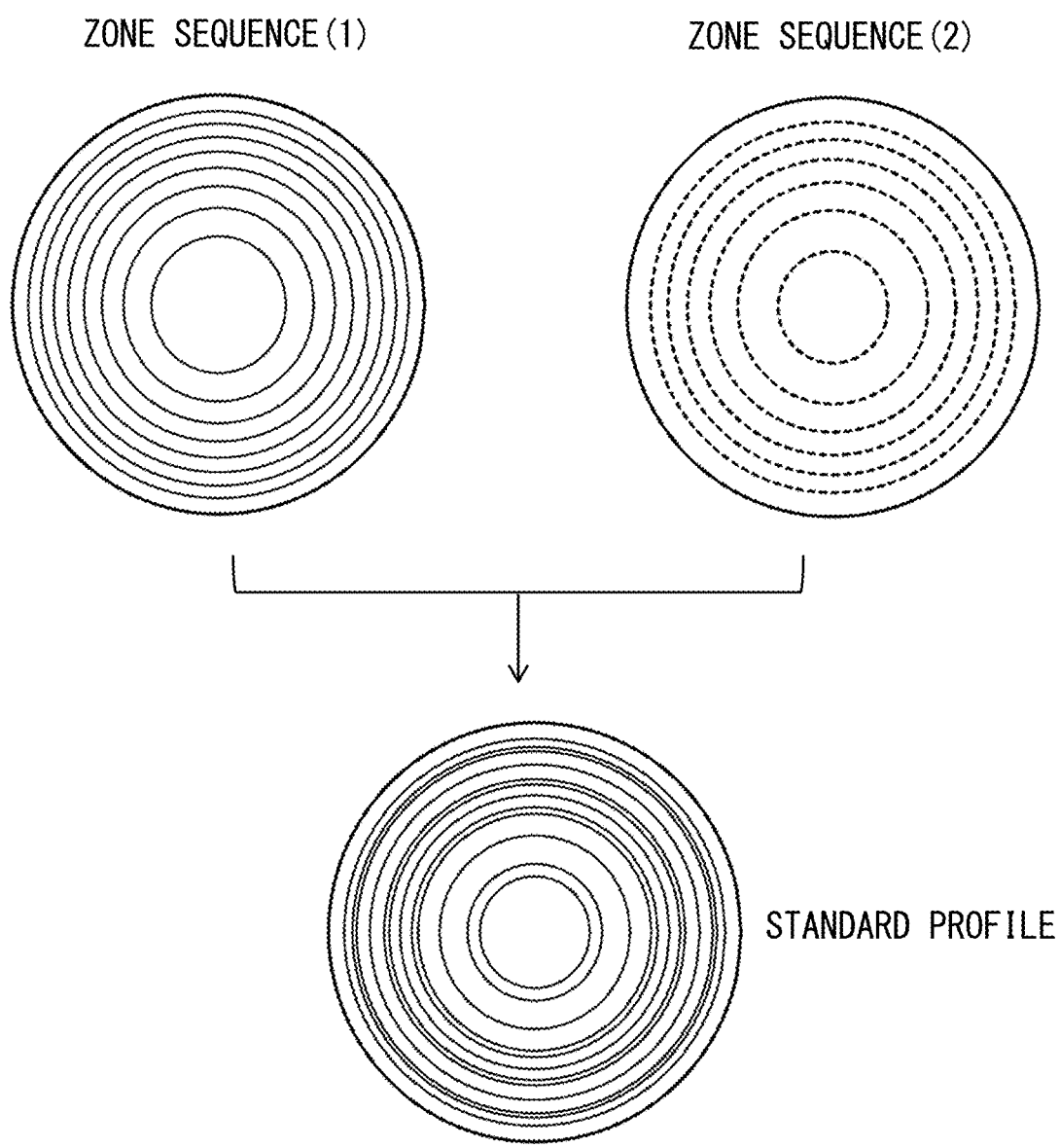
FIG. 4 is a drawing for explaining an example of a standard profile made by overlapping two zone sequences, as the blaze of a diffraction grating configured by overlapping a plurality of zone sequences.

Furthermore, with the aforementioned examples, the entire surface of the lens substantially constitutes the optical part as shown in FIG. 4. However, as with a contact lens, it is also possible to suitably provide a peripheral part that does not impart an optical effect on the eye optical system, etc. in the lens outer peripheral part. Also, in the optical part as well, a diffraction grating can be provided partially only in prescribed regions in the radial direction. For example, it is also possible to provide a refractive lens at the radially inner side of the optical part, while providing a diffraction grating at the radially outer side thereof to obtain a diffractive lens, etc.

Also, in the case of using the present invention for an ophthalmic lens for which the diffraction grating is provided partially in the radial direction, when selecting the specific zone for setting the reversed inclination using selection criteria such as the zone pitch, the zone area, or the width of the intensity distribution on the optical axis as described above, the standard profile that gives each reference value is a theoretical value. Specifically, for example, even when the diffraction grating is provided only to the radially outer side of the radially middle part of the optical part, in the Means for Solving the Problem section noted above, the "zone pitch $\Delta r_{max}$ for a maximum pitch zone having a maximum zone pitch among the plurality of concentric zones" noted in the first, fourth, and thirteenth modes of the present invention, the "zone area $S_{max}$ for a maximum area zone having a maximum zone area among the plurality of concentric zones" noted in the second, fourth, and thirteenth modes, and the "half-value width $\Delta D_{min}$ in a narrowest intensity distribution zone for which a half-value width of an intensity distribution on an optical axis of a light emitted from that zone is narrowest among the plurality of concentric zones" noted in the third, fourth, and thirteenth modes are all to be applicable to the standard profile comprising the blaze shaped phase function continuous from the optical center of the optical part to the outer peripheral edge as illustrated in FIG. 5A as the target. This makes it possible to objectively and appropriately set selection criteria.

On the other hand, when specifying a zone for setting a reversed inclination in the present invention, zones that exist within the region of which the diffraction grating is set are targeted. Specifically, the adjustment zone which is "at least one of the zones configuring the diffraction grating" noted in the first to fourth and thirteenth modes of the present invention in the Means for Solving the Problem section are zones that are set and actually exist in the lens optical part.

It is also possible to apply the present invention to at least a portion of the region of which the diffraction grating is set in the diffractive multi-focal ophthalmic lens. In Patent Document 5, noted is an ophthalmic lens comprising a blaze shaped phase function having equal pitch that is set partially in the radial direction. In a case in which the ophthalmic lens includes the diffraction grating to which the present invention can be applied in other region than the equal pitch region, the present invention can also be applied to such ophthalmic lens.

Yet furthermore, the phase function given by the present invention is realized by setting as a diffraction grating in the ophthalmic lens. Here, for the optical material of the ophthalmic lens for realizing the diffraction grating, it is possible to use various materials known from the past according to the desired ophthalmic lens such as contact lens, IOL, ICL, and eyeglass lenses. Also, the diffraction grating that gives the blaze shaped phase function set based on the present invention can be realized by adjusting and setting the light transmission speed in each site of the lens, for example. However, for practical use, it is preferable to realize this diffraction grating by providing a relief structure that reflects the optical path length correlating to the phase in the lens surface, for example. Alternatively, with a laminated structure lens comprising materials of different light transmission speeds (refractive index), it is also possible to set a relief structure for the boundary surface of the materials, thereby making the lens surface be smooth, or be a refracting surface, etc. (see Japanese Unexamined Patent Publication No. JP-A-2001-042112). The relief structure of the lens surface or inner surface can be formed, based on a known manufacturing method of a contact lens, IOL, ICL, etc., through a known technique of implementing chemical or mechanical surface processing such as etching, lathe turning on the optical material, for example.

In addition, though not listed as individual examples, the present invention can be implemented in modes for which various changes, modifications, and improvements, etc. are made based on the knowledge of those skilled in the art, and it goes without saying that such an implementation mode is included in the scope of the present invention as long as it does not stray from the spirit of the present invention.

The invention claimed is:

1. A diffractive multi-focal ophthalmic lens for which a diffraction grating comprising a blaze shaped phase function is configured by a plurality of concentric zones for which a plurality of zone sequences with a zone radius given by Equation 1 are overlapped such that a plurality of focal points are set, wherein
at least one of the zones configuring the diffraction grating, the zone having a zone pitch $\Delta r$ that satisfies $\Delta r \leq 0.5 \times \Delta r_{max}$ with respect to a zone pitch $\Delta r_{max}$ for a maximum pitch zone having a maximum zone pitch among the plurality of concentric zones, serves as an adjustment zone and,
in the adjustment zone, a blaze shaped phase function for which an inclination is reversed with respect to an inclination of the blaze shaped phase function in the maximum pitch zone is set, wherein $$r_n = \sqrt{r_1^2 + \frac{2(n-1)\lambda}{P}} \qquad \text{[Equation 1]}$$

is defined as
$r_n$: nth zone radius of a certain zone sequence
$r_1$: 1st zone radius of the zone sequence
n: Natural number
P: Addition power based on 1st order diffracted light of the zone sequence
$\lambda$: Design wavelength.

2. The diffractive multi-focal ophthalmic lens according to claim 1, wherein in a diffraction grating region in which the diffraction grating is provided, a total number of the adjustment zone is less than ½ a total number of the zones in the diffraction grating region.

3. The diffractive multi-focal ophthalmic lens according to claim 1, wherein the phase function set in the adjustment zone is a blaze shaped phase function that does not form a valley point between the adjustment zone and a neighboring zone that neighbors the adjustment zone.

4. The diffractive multi-focal ophthalmic lens according to claim 1, wherein the lens has optical characteristics in which an intensity of peak of a multi-order light caused by the diffraction grating is low with respect to that of a standard diffractive multi-focal lens having a standard profile for which the blaze shaped phase function for which the inclination is reversed in the adjustment zone is not set.

5. The diffractive multi-focal ophthalmic lens according to claim 1, wherein the diffraction grating comprising the blaze shaped phase function is set as a relief structure reflecting an optical path length correlating to a phase.

6. The diffractive multi-focal ophthalmic lens according to claim 1, wherein one of the plurality of focal points serves as a focal point for far vision, and the focal point for far vision is given by a 0th order diffracted light of the diffraction grating comprising the blaze shaped phase function.

7. A diffractive multi-focal ophthalmic lens for which a diffraction grating comprising a blaze shaped phase function is configured by a plurality of concentric zones for which a plurality of zone sequences with a zone radius given by Equation 2 are overlapped such that a plurality of focal points are set, wherein
at least one of the zones configuring the diffraction grating, the zone having a zone area S that satisfies $S \leq 0.5 \times S_{max}$ with respect to a zone area $S_{max}$ for a maximum area zone having a maximum zone area among the plurality of concentric zones, serves as an adjustment zone and,
in the adjustment zone, a blaze shaped phase function for which an inclination is reversed with respect to an inclination of the blaze shaped phase function in the maximum area zone is set, wherein $$r_n = \sqrt{r_1^2 + \frac{2(n-1)\lambda}{P}} \qquad \text{[Equation 2]}$$

is defined as
$r_n$: nth zone radius of a certain zone sequence
$r_1$: 1st zone radius of the zone sequence
n: Natural number
P: Addition power based on 1st order diffracted light of the zone sequence
$\lambda$: Design wavelength.

8. The diffractive multi-focal ophthalmic lens according to claim 7, wherein in a diffraction grating region in which the diffraction grating is provided, a total number of the adjustment zone is less than ½ a total number of the zones in the diffraction grating region.

9. The diffractive multi-focal ophthalmic lens according to claim 7, wherein the phase function set in the adjustment zone is a blaze shaped phase function that does not form a valley point between the adjustment zone and a neighboring zone that neighbors the adjustment zone.

10. The diffractive multi-focal ophthalmic lens according to claim 7, wherein the lens has optical characteristics in which an intensity of peak of a multi-order light caused by the diffraction grating is low with respect to that of a standard diffractive multi-focal lens having a standard profile for which the blaze shaped phase function for which the inclination is reversed in the adjustment zone is not set.

11. The diffractive multi-focal ophthalmic lens according to claim 7, wherein the diffraction grating comprising the blaze shaped phase function is set as a relief structure reflecting an optical path length correlating to a phase.

12. The diffractive multi-focal ophthalmic lens according to claim 7, wherein one of the plurality of focal points serves as a focal point for far vision, and the focal point for far vision is given by a 0th order diffracted light of the diffraction grating comprising the blaze shaped phase function.

13. A diffractive multi-focal ophthalmic lens for which a diffraction grating comprising a blaze shaped phase function is configured by a plurality of concentric zones for which a plurality of zone sequences with a zone radius given by Equation 3 are overlapped such that a plurality of focal points are set, wherein
at least one of the zones configuring the diffraction grating, the zone having a half-value width $\Delta D$ that satisfies $\Delta D \geq 2 \times \Delta D_{min}$ with respect to a half-value width $\Delta D_{min}$ in a narrowest intensity distribution zone for which a half-value width of an intensity distribution on an optical axis of a light emitted from that zone is narrowest among the plurality of concentric zones, serves as an adjustment zone and,
in the adjustment zone, a blaze shaped phase function for which an inclination is reversed with respect to an inclination of the blaze shaped phase function in the narrowest intensity distribution zone is set, wherein $$r_n = \sqrt{r_1^2 + \frac{2(n-1)\lambda}{P}} \quad \text{[Equation 3]}$$

is defined as
$r_n$: nth zone radius of a certain zone sequence
$r_1$: 1st zone radius of the zone sequence
n: Natural number
P: Addition power based on 1st order diffracted light of the zone sequence
$\lambda$: Design wavelength.

14. The diffractive multi-focal ophthalmic lens according to claim 13, wherein in a diffraction grating region in which the diffraction grating is provided, a total number of the adjustment zone is less than ½ a total number of the zones in the diffraction grating region.

15. The diffractive multi-focal ophthalmic lens according to claim 13, wherein the phase function set in the adjustment zone is a blaze shaped phase function that does not form a valley point between the adjustment zone and a neighboring zone that neighbors the adjustment zone.

16. The diffractive multi-focal ophthalmic lens according to claim 13, wherein the lens has optical characteristics in which an intensity of peak of a multi-order light caused by the diffraction grating is low with respect to that of a standard diffractive multi-focal lens having a standard profile for which the blaze shaped phase function for which the inclination is reversed in the adjustment zone is not set.

17. The diffractive multi-focal ophthalmic lens according to claim 13, wherein the diffraction grating comprising the blaze shaped phase function is set as a relief structure reflecting an optical path length correlating to a phase.

18. The diffractive multi-focal ophthalmic lens according to claim 13, wherein one of the plurality of focal points serves as a focal point for far vision, and the focal point for far vision is given by a 0th order diffracted light of the diffraction grating comprising the blaze shaped phase function.

19. A diffractive multi-focal ophthalmic lens for which a diffraction grating comprising a blaze shaped phase function is configured by a plurality of concentric zones for which a plurality of zone sequences with a zone radius given by Equation 4 are overlapped such that a plurality of focal points are set, wherein
at least one adjustment zone is provided, the adjustment zone being described in at least one of (A), (B), and (C) listed below:
(A) an adjustment zone defined by at least one of the zones configuring the diffraction grating, the zone having a zone pitch $\Delta r$ that satisfies $\Delta r \leq 0.5 \times \Delta r_{max}$ with respect to a zone pitch $\Delta r_{max}$ for a maximum pitch zone having a maximum zone pitch among the plurality of concentric zones, the adjustment zone being such that a blaze shaped phase function for which an inclination is reversed with respect to an inclination of the blaze shaped phase function in the maximum pitch zone is set;
(B) an adjustment zone defined by at least one of the zones configuring the diffraction grating, the zone having a zone area S that satisfies $S \leq 0.5 \times S_{max}$ with respect to a zone area $S_{max}$ for a maximum area zone having a maximum zone area among the plurality of concentric zones, the adjustment zone being such that a blaze shaped phase function for which an inclination is reversed with respect to an inclination of the blaze shaped phase function in the maximum area zone is set; and
(C) an adjustment zone defined by at least one of the zones configuring the diffraction grating, the zone having a half-value width $\Delta D$ that satisfies $\Delta D \geq 2 \times \Delta D_{min}$ with respect to a half-value width $\Delta D_{min}$ in a narrowest intensity distribution zone for which a half-value width of an intensity distribution on an optical axis of a light emitted from that zone is narrowest among the plurality of concentric zones, the adjustment zone being such that a blaze shaped phase function for which an inclination is reversed with respect to an inclination of the blaze shaped phase function in the narrowest intensity distribution zone is set, wherein $$r_n = \sqrt{r_1^2 + \frac{2(n-1)\lambda}{P}} \quad \text{[Equation 4]}$$

is defined as
$r_n$: nth zone radius of a certain zone sequence
$r_1$: 1st zone radius of the zone sequence
n: Natural number
P: Addition power based on 1st order diffracted light of the zone sequence
$\lambda$: Design wavelength.

20. The diffractive multi-focal ophthalmic lens according to claim 19, wherein in a diffraction grating region in which the diffraction grating is provided, the adjustment zone is positioned and set to a radially inner side of a radial center of the diffraction grating region, and the adjustment zone is the adjustment zone that satisfies conditions described in (B).

21. The diffractive multi-focal ophthalmic lens according to claim 19, wherein in a diffraction grating region in which the diffraction grating is provided, the adjustment zone is positioned and set to a radially outer side of a radial center of the diffraction grating region, and the adjustment zone is the adjustment zone that satisfies conditions described in (A).

22. The diffractive multi-focal ophthalmic lens according to claim 19, wherein
in a diffraction grating region in which the diffraction grating is provided, the at least one adjustment zone is set to each of a radially inner side and a radially outer side of a radial center of the diffraction grating region,
the adjustment zone set to the radially inner side is the adjustment zone that satisfies at least conditions described in (B), and
the adjustment zone set to the radially outer side is the adjustment zone that satisfies at least conditions described in (A).

23. A method for manufacturing a diffractive multi-focal ophthalmic lens comprising:
a step of setting a diffraction grating for which a plurality of focal points are set, with a blaze shaped phase function, using a plurality of concentric zones for which a plurality of zone sequences with a zone radius given by Equation 5 are overlapped;
a step of setting an adjustment zone, the adjustment zone being described in at least one of (A), (B), and (C) listed below:
(A) an adjustment zone defined by at least one of the zones configuring the diffraction grating, the zone having a zone pitch $\Delta r$ that satisfies $\Delta r \leq 0.5 \times \Delta r_{max}$ with respect to a zone pitch $\Delta r_{max}$ for a maximum pitch zone having a maximum zone pitch among the plurality of concentric zones, the adjustment zone being such that a blaze shaped phase function for which an inclination is reversed with respect to an inclination of the blaze shaped phase function in the maximum pitch zone is set;
(B) an adjustment zone defined by at least one of the zones configuring the diffraction grating, the zone having a zone area S that satisfies $S \leq 0.5 \times S_{max}$ with respect to a zone area $S_{max}$ for a maximum area zone having a maximum zone area among the plurality of concentric zones, the adjustment zone being such that a blaze shaped phase function for which an inclination is reversed with respect to an inclination of the blaze shaped phase function in the maximum area zone is set; and
(C) an adjustment zone defined by at least one of the zones configuring the diffraction grating, the zone having a half-value width $\Delta D$ that satisfies $\Delta D \geq 2 \times \Delta D_{min}$ with respect to a half-value width $\Delta D_{min}$ in a narrowest intensity distribution zone for which a half-value width of an intensity distribution on an optical axis of a light emitted from that zone is narrowest among the plurality of concentric zones, the adjustment zone being such that a blaze shaped phase function for which an inclination is reversed with respect to an inclination of the blaze shaped phase function in the narrowest intensity distribution zone is set; and
a step of forming the diffraction grating provided with the plurality of zones including the adjustment zone in an optical material, wherein $$r_n = \sqrt{r_1^2 + \frac{2(n-1)\lambda}{P}} \qquad \text{[Equation 5]}$$

is defined as
$r_n$: nth zone radius of a certain zone sequence
$r_1$: 1st zone radius of the zone sequence
n: Natural number
P: Addition power based on 1st order diffracted light of the zone sequence
$\lambda$: Design wavelength.

* * * * *